US006642024B1

(12) United States Patent
Pennica

(10) Patent No.: US 6,642,024 B1
(45) Date of Patent: Nov. 4, 2003

(54) GUANYLATE-BINDING PROTEIN

(75) Inventor: Diane Pennica, Burlingame, CA (US)

(73) Assignee: Genentech Inc., South San Francisco, CA (US)

( * ) Notice: Subject to any disclaimer, the term of this patent is extended or adjusted under 35 U.S.C. 154(b) by 54 days.

(21) Appl. No.: 09/643,657

(22) Filed: Aug. 17, 2000

Related U.S. Application Data

(63) Continuation of application No. 09/015,089, filed on Jan. 29, 1998, now abandoned.

(51) Int. Cl.[7] ......................... C12P 21/06; C07H 17/00; C07K 14/00

(52) U.S. Cl. ................ 435/69.1; 435/320.1; 435/252.3; 435/325; 536/23.1; 530/350

(58) Field of Search ...................... 536/23.1; 435/320.1, 435/252.3, 69.1, 325; 530/350

(56) References Cited

U.S. PATENT DOCUMENTS 5,871,965 A 2/1999 Bandman et al.

OTHER PUBLICATIONS

Adams et al., "Initial assessment of human gene diversity and expression patterns based upon 83 million nucleotides of cDNA sequence" *Nature* 377 (6547 Suppl):3–174 (1995).

Asundi et al., "Molecular cloning and characterization of an isoprenylated 67 kDa protein" *Biochimica et Biophysica Acta* 1217:257–265 (1994).

BLASTN with as.hu.GBP4 (Jan. 28, 1998).

BLASTP with p1.GBP–4 (Jan. 28, 1998).

Braun et al., "Identification of target genes for the Ewing's sarcoma EWS/FLI fusion protein by representational difference analysis" *Mol. Cell Biol.* 15:4623–4630 (1995).

Briken et al., "Interferon regulatory factor I is required for mouse Gbp gene activation by gamma interferon" *Mol. Cell Biol.* 15:975–982 (1995).

Cheng et al., "Affinity purification of an interferon–induced human guanylate–binding protein and its characterization" *Journal of Biological Chemistry* 260:15834–15839 (1985).

Cheng et al., "Interferon induction of fibroblast proteins with guanylate binding activity" *Journal of Biological Chemistry* 258:7746–7750 (1983).

Cheng et al., "Interferon–induced guanylate–binding proteins lack an N(T)KXD consensus motif and bind GMP in addition to GDP and GTP" *Mol. Cell Biol.* 11:4717–4725 (1991).

Cheng et al., "Nonidentical induction of the guanylate binding and the 56K protein by type I and type II interferons" *J. Interferon Res.* 6:417–427 (1986).

Darnell, Jr. et al., "Jak–STAT Pathways and Transcriptional Activation in Response to IFNs and Other Extracellular Signaling Proteins" *Science* 264(5164):1415–1421 (Jun. 3, 1994).

Decker et al., "Interactions of α–and γ–interferon in the transcriptional regulation of the gene encoding a guanylate-binding protein" *EMBO Journal* 8:2009–2014 (1989).

Dever and Merrick, "The GTP–binding domain revisited" *The quanine–nucleotide binding proteins: common structural and functional properties*, L. Bosch, B. Kraal, and A. Parmegianni, New York:Plenum Press pp. 35–48 (1995).

Dever et al., "GTP–binding domain: three consensus sequence elements with distinct spacing" *Proc. Natl. Acad. Sci. USA* 84:1814–1818 (1987).

Diatchenko et al., "Suppression subtractive hybridization: a method for generating differentially regulated or tissue–specific cDNA probes and libraries" *Proc. Natl. Acad. Sci. USA* 93:6025–6030 (1996).

Gibbs et al., "Farnesyltransferase inhibitors: Ras research yields a potential cancer therapeutic" *Cell* 77:175–178 (1994).

Gruenberg and Maxfield, "Membrane transport in the endocytic pathway" *Curr Opin Cell Biol* 7:552–563 (1995).

Hancock et al., "A polybasic domain of palmitoylation is required in addition to the CAAX motif to localized p21$^{ras}$ to the plasma membrane" *Cell* 63:133–139 (1990).

Horisberger et al., "Cloning and sequence analyses of cDNAs for interferon–and virus–induced human Mx proteins reveal that they contain putative guanine nucleotide-binding sites: functional study of the corresponding gene promoter" *Journal of Virology* 64:1171–1181 (1990).

Iolascon et al., "Frequent clonal loss of heterozygosity (LOH) in the chromosomal region Ip32 occurs in childhood T cell acute lymphoblastic leukemia (T–ALL) carrying rearrangements of the TAL1 gene" *Leukemia* 11:359–363 (1997).

Jurnak, "Structure of the GDP domain of EF–Tu and location of the amino acids homologous to ras oncogene proteins" *Science* 230:32–36 (1985).

Lew et al., "Overlapping Elements in the Guanylate–Binding Protein Gene Promoter Mediate Transcriptional Induction by Alpha and Gamma Interferons" *Molecular & Cellular Biology* 11(1):182–191 (1991).

Lewis et al., "Identification of putative c–Myc–responsive genes: characterization of rcl, a novel growth–related gene" *Mol. Cell Biol.* 17:4967–4978 (1997).

Marks et al., "Protein targeting by tyrosine–and di–leucine-based signals: evidence for distinct saturable components" *J. Cell Biol* 135:341–354 (1996).

Nagai et al., "Detection and cloning of a common region of loss of heterozygosity at chromosome 1p in breast cancer" *Cancer Research* 55:1752–1757 (1995).

(List continued on next page.)

*Primary Examiner*—Karen Cochrane Carlson
(74) *Attorney, Agent, or Firm*—Gates & Cooper LLP

(57) ABSTRACT

A member of the guanylate-binding protein family, designated GBP-4, is provided. Also provided are isolated nucleic acid encoding GBP-4, vectors and host cells containing such nucleic acid molecule, and a method for producing the GBP-4 recombinantly.

35 Claims, 9 Drawing Sheets

OTHER PUBLICATIONS

Nantais et al., "Prenylation of an interferon–γ–induced GTP-binding: the human guanylate binding protein, huGBP1" *J. Leukoc. Biol.* 60:423–431 (1996).

Neun et al., "GTPase properties of the interferon–induced human guanylate–binding protein 2" *FEBS Letters* 390:69–72 (1996).

Nicolet et al., "Promoter analysis of an interferon–inducible gene associated with macrophage activation" *J. Immunol.* 152:153–162 (1994).

Parsonnet, "Helicobacter pylori and gastric cancer" *Gastroenterol Clin. North Am.* 22:89–104 (1993).

Peddanna et al., "Genetics of gastric cancer" *Anticancer Res*, 15:2055–2064 (1995).

Schena et al., "Quantitative monitoring of gene expression patterns with a complementary DNA microarray" *Science* 270:467–470 (1995).

Schwemmle et al., "Chicken guanylate–binding protein. Conservation of GTPase activity and induction by cytokines" *Journal of Biological Chemistry* 271:10304–10308 (1996).

Schwemmle et al., "The interferon–induced 67–kDa guanylate–binding protein (hGBP1) is a GTPase that converts GTP to GMP" *Journal of Biological Chemistry* 269:11299–11305 (1994).

Shuai, "Interferon–activated signal transduction to the nucleus" *Curr Opin Cell Biol* 6:253–259 (1994).

Stemmermann et al., "The molecular biology of esophageal and gastric cancer and their precursors: oncogenes, tumor suppressor genes, and growth factors" *Hum. Pathol.* 25:968–981 (1994).

Strausberg, "tw76b04.x1 NCI_Ut3 *Homo sapiens* cDNA Image:2265583 3' similar to gb:M55542 Interferon–Induced Guanylate–Binding Protein 1 (Human);, mRNA sequence" (Accession No. AI811907.1) (May 9, 1996).

Strausberg, "ws36e12.x1 NCI_CGAP_GC6 *Homo sapiens* cDNA clone Image:2499310 3' similar to gb:M55542 Interferon–Induced Guanylate–Binding Protein 1 (Human);, mRNA sequence" (Accession No. AI989871) (Dec. 20, 1995).

Strehlow et al., "The interferon–inducible GBP1 gene: structure and mapping to human chromosome 1" *Gene* 144:295–299 (1994).

Tamura et al., "Two distinct regions of deletion on the long arm of chromosome 5 in differentiated adenocarcinomas of the stomach" *Cancer Research* 56:612–615 (1996).

Tanaka et al., "Cooperation of the tumour suppressors IRF–1 and p53 in response to DNA damage" *Nature* 382:816–818 (1996).

Taylor et al., "Identification of a novel GTPase, the inducible expressed GTPase, that accumulates in response to interferon γ" *Journal of Biological Chemistry* 271:20399–20405 (1996).

Taylor et al., "The inducibly expressed GTPase localizes to the endoplasmic reticulum, independently of GTP binding" *Journal of Biological Chemistry* 272:10639–10645 (1997).

Velculescu et al., "Serial analysis of gene expression" *Science* 270:484–487 (1995).

Vestal et al., "A New IFN–γ Induced 67 KDA Member of a Family of Guanylate Binding Proteins, Murine GBP–2" *Molecular Biology of the Cell* 7:527A (Suppl. 1996).

Vestal et al., "A New Murine IFN–γ Induced 67 KDA Member of a Family of Guanylate Binding Proteins" *Molecular Biology of the Cell* 6:288A (Suppl. 1995).

Vestal et al., "Rat p67 GBP is induced by interferon–γ and isoprenoid–modified in macrophages" *Biochem. Biophys. Res. Comm.* 224:528–534 (1996).

Willman et al., "Deletion of IRF–1, mapping to chromosome 5q31.1, in human leukemia and preleukemic myelodysplasia" *Science* 259:968–971 (1993).

Wynn et al., "Identification and characterization of a new gene family induced during macrophage activation" *J. Immunol.* 147:4384–4392 (1991).

Zhang et al., "Gene expression profiles in normal and cancer cells" *Science* 276:1268–1272 (1997).

Zhang et al., "Protein prenylation: molecular mechanisms and functional consequences" *Annu. Rev. Biochem.* 65:241–269 (1996).

```
   1  GAACCCACCA GAAGGAAGAA ACTCCAAACA CATCCGAACA TCAGAAGGAG CAAACTCGTG ACACGCCACC TTTAAGAACC GTGACACTCA ACGCTAGGGT
      CTTGGGTGGT CTTCCTTCTT TGAGGTTTGT GTAGGCTTGT AGTCTTCCTC GTTTGAGCAC TGTGCGGTGG AAATTCTTGG CACTGTGAGT TGCGATCCCA
 101  CCGCGGCTTC ATTCTTGAAG TCAGTGAGAC CAAGAACCCA CCAATTCCGG ACACGGCAAA GTAACATCCT AGAC  ATG GCT TTA GAG ATC CAC
      GGCGCCGAAG TAAGAACTTC AGTCACTCTG GTTCTTGGGT GGTTAAGGCC TGTGCCGTTT CATTGTAGGA TCTG  TAC CGA AAT CTC TAG GTG
   1                                                                                   M   A   L   E   I   H
 193  ATG TCA GAC CCC ATG TGC CTC ATC GAG AAC TTT AAT GAG CAG CTG AAG GTT AAT CAG GAA GCT TTG GAG ATC CTG TCT GCC
      TAC AGT CTG GGG TAC ACG GAG TAG CTC TTG AAA TTA CTC GTC GAC TTC CAA TTA GTC CTT CGA AAC CTC TAG GAC AGA CGG
   7  M   S   D   P   M   C   L   I   E   N   F   N   E   Q   L   K   V   N   Q   E   A   L   E   I   L   S   A
 274  ATT ACG CAA CCT GTA GTT GTG GTA GCG ATT GTG GGC CTC TAT CGC ACT GGC AAA TCC TAC CTG ATG AAC AAG CTG GCT GGG
      TAA TGC GTT GGA CAT CAA CAC CAT CGC TAA CAC CCG GAG ATA GCG TGA CCG TTT AGG ATG GAC TAC TTG TTC GAC CGA CCC
  34  I   T   Q   P   V   V   V   V   A   I   V   G   L   Y   R   T   G   K   S   Y   L   M   N   K   L   A   G
 355  AAG AAC AAG GGC TTC TCT GTT GCA TCT ACG GTG CAG TCT CAC ACC AAG GGA ATT TGG ATA TGG TGT GTG CCT CAT CCC AAC
      TTC TTG TTC CCG AAG AGA CAA CGT AGA TGC CAC GTC AGA GTG TGG TTC CCT TAA ACC TAT ACC ACA CAC GGA GTA GGG TGG
  61  K   N   K   G   F   S   V   A   S   T   V   Q   S   H   T   K   G   I   W   I   W   C   V   P   H   P   N
 436  TGG CCA AAT CAC ACA TTA GTT CTG CTT GAC ACC GAG GGC CTG GGA GAT GTA CAG AAG GCT GAC AAC AAG AAT GAT ATC CAG
      ACC GGT TTA GTG TGT AAT CAA GAC GAA CTG TGG CTC CCG GAC CCT CTA CAT CTC TTC CGA CTG TTG TTC TTA CTA TAG GTC
  88  W   P   N   H   T   L   V   L   L   D   T   E   G   L   G   D   V   E   K   A   D   N   K   N   D   I   Q
 517  ATC TTT GCA CTG GCA CTC TTA CTG AGC AGC ACC TTT GTG TAC AAT ACT GTG AAC AAA ATT GAT CAG GGT GCT ATC GAC CTA
      TAG AAA CGT GAC CGT GAG AAT GAC TCG TCG TGG AAA CAC ATG TTA TGA CAC TTG TTT TAA CTA GTC CCA CGA TAG CTG GAT
 115  I   F   A   L   A   L   L   L   S   S   T   F   V   Y   N   T   V   N   K   I   D   Q   G   A   I   D   L
 598  CTG CAC AAT GTG ACA GAA CTG ACA GAT CTG CTC AAG GCA AGA AAC TCA CCC GAC CTT GAC AGG GTT GAA GAT CCT GCT GAC
      GAC GTG TTA CAC TGT CTT GAC TGT CTA GAC GAG TTC CGT TCT TTG AGT GGG CTG GAA CTG TCC CAA CTT CTA GGA CGA CTG
 142  L   H   N   V   T   E   L   T   D   L   L   K   A   R   N   S   P   D   L   D   R   V   E   D   P   A   D
 679  TCT GCG AGC TTC TTC CCA GAC TTA GTG TGG ACT CTG AGA GAT TTC TGC TTA GGC CTG GAA ATA GAT GGG CAA CTT GTC ACA
      AGA CGC TCG AAG AAG GGT CTG AAT CAC ACC TGA GAC TCT CTA AAG ACG AAT CCG GAC CTT TAT CTA CCC GTT GAA CAG TGT
 169  S   A   S   F   F   P   D   L   V   W   T   L   R   D   F   C   L   G   L   E   I   D   G   Q   L   V   T
 760  CCA GAT GAA TAC CTG GAG AAT TCC CTA AGG CCA AAG CAA GGT AGT GAT CAA AGA GTT CAA AAT TTC AAT TTG CCC CGT CTG
      GGT CTA CTT ATG GAC CTC TTA AGG GAT TCC GGT TTC GTT CCA TCA CTA GTT TCT CAA GTT TTA AAG TTA AAC GGG GCA GAC
 196  P   D   E   Y   L   E   N   S   L   R   P   K   Q   G   S   D   Q   R   V   Q   N   P   N   L   P   R   L
 841  TGT ATA CAG AAG TTC TTT CCA AAA AAG AAA TGC TTT ATC TTT GAC TTA CCT GCT CAC CAA AAA AAG CTT GCC CAA CTT GAA
      ACA TAT GTC TTC AAG AAA GGT TTT TTC TTT ACG AAA TAG AAA CTG AAT GGA CGA GTG GTT TTT TTC GAA CGG GTT GAA CTT
 223  C   I   Q   K   F   F   P   K   K   K   C   F   I   F   D   L   P   A   H   Q   K   K   L   A   Q   L   E
 922  ACA CTG CCT GAT GAT GAG CTA GAG CCT GAA TTT GTG CAA CAA GTG ACA GAA TTC TGT TCC TAC ATC TTT AGC CAT TCT ATG
      TGT GAC GGA CTA CTA CTC GAT CTC GGA CTT AAA CAC GTT GTT CAC TGT CTT AAG ACA AGG ATG TAG AAA TCG GTA AGA TAC
 250  T   L   P   D   D   E   L   E   P   E   F   V   Q   Q   V   T   E   F   C   S   Y   I   F   S   H   S   M
1003  ACC AAG ACT CTT CCA GGT GGC ATC ATG GTC AAT GGA TCT CGT CTA AAG AAC CTG GTG CTG ACC TAT GTC AAT GCC ATC AGC
      TGG TTC TGA GAA GGT CCA CCG TAG TAC CAG TTA CCT AGA GCA GAT TTC TTG GAC CAC GAC TGG ATA CAG TTA CGG TAG TCG
 277  T   K   T   L   P   G   G   I   M   V   N   G   S   R   L   K   N   L   V   L   T   Y   V   N   A   I   S
1084  AGT GGG GAT CTG CCT TGC ATA GAG AAT GCA GTC CTG GCC TTG GCT CAG AGA GAG AAC TCA GCT GCA GTG CAA AAG GCC ATT
      TCA CCC CTA GAC GGA ACG TAT CTC TTA CGT CAG GAC CGG AAC CGA GTC TCT CTC TTG AGT CGA CGT CAC GTT TTC CGG TAA
 304  S   G   D   L   P   C   I   E   N   A   V   L   A   L   A   Q   R   E   N   S   A   A   V   Q   K   A   I
1165  GCC CAC TAT GAC CAG CAA ATG GGC CAG AAA GTG CAG CTG CCC ATG GAA ACC CTC CAG GAG CTG CTG GAC CTG CAC AGG ACC
      CGG GTG ATA CTG GTC GTT TAC CCG GTC TTT CAC GTC GAC GGG TAC CTT TGG GAG GTC CTC GAC GAC CTG GAC GTG TCC TGG
 331  A   H   Y   D   Q   Q   M   G   Q   K   V   Q   L   P   M   E   T   L   Q   E   L   L   D   L   H   R   T
1246  AGT GAG AGG GAG GCC ATT GAA GTC TTC ATG AAA AAC TCT TTC AAG GAT GTA GAC CAA AGT TTC CAG AAA GAA TTG GAG ACT
      TCA CTC TCC CTC CGG TAA CTT CAG AAG TAC TTT TTG AGA AAG TTC CTA CAT CTG GTT TCA AAG GTC TTT CTT ACC CTC TGA
 358  S   E   R   E   A   I   E   V   F   M   K   N   S   F   K   D   V   D   Q   S   F   Q   K   E   L   E   T
1327  CTA CTA GAT GCA AAA CAG AAT GAC ATT TGT AAA CGG AAC CTG GAA GCA TCC TCG GAT TAT TGC TCG GCT TTA CTT AAG GAT
      GAT GAT CTA CGT TTT GTC TTA CTG TAA ACA TTT GCC TTG GAC CTT CGT AGG AGC CTA ATA ACG AGC CGA AAT GAA TTC CTA
 385  L   L   D   A   K   Q   N   D   I   C   K   R   N   L   E   A   S   S   D   Y   C   S   A   L   L   K   D
1408  ATT TTT GGT CCT CTA GAA GAA GCA GTG AAG CAG GGA ATT TAT TCT AAG CCA GGA GGC CAT AAT CTC TTC ATT CAG AAA ACA
      TAA AAA CCA GGA GAT CTT CTT CGT CAC TTC GTC CCT TAA ATA AGA TTC GGT CCT CCG GTA TTA GAG AAG TAA GTC TTT TGT
 412  I   F   G   P   L   E   E   A   V   K   Q   G   I   Y   S   K   P   G   G   H   N   L   F   I   Q   K   T
1489  GAA GAA CTG AAG GCA AAG TAC TAT CGG GAG CCT CGG AAA GGA ATA CAG GCT GAA GAA GTT CTG CAG AAA TAT TTA AAG TCC
      CTT CTT GAC TTC CGT TTC ATG ATA GCC CTC GGA GCC TTT CCT TAT GTC CGA CTT CTT CAA GAC GTC TTT ATA AAT TTC AGG
 439  E   E   L   K   A   K   Y   Y   R   E   P   R   K   G   I   Q   A   E   E   V   L   Q   K   Y   L   K   S
1570  AAG GAG TCT GTG AGT CAT GCA ATA TTA CAG ACT GAC CAG GCT CTC ACA GAG ACG GAA AAA AAG AAG AAA GAG GCA CAA GTG
      TTC CTC AGA CAC TCA GTA CGT TAT AAT GTC TGA CTG GTC CGA GAG TGT CTC TGC CTT TTT TTC TTC TTT CTC CGT GTT CAC
 466  K   E   S   V   S   H   A   I   L   Q   T   D   Q   A   L   T   E   T   E   K   K   K   K   E   A   Q   V
1651  AAA GCA GAA GCT GAA AAG GCT GAA GCG CAA AGG TTG GCG GCG ATT CAA AGG CAG AAC GAG CAA ATG ATG CAG GAG AGG GAG
      TTT CGT CTT CGA CTT TTC CGA CTT CGC GTT TCC AAC CGC CGC TAA GTT TCC GTC TTG CTC GTT TAC TAC GTC CTC TCC CTC
 493  K   A   E   A   E   K   A   E   A   Q   R   L   A   A   I   Q   R   Q   N   E   Q   M   M   Q   E   R   E
1732  AGA CTC CAT CAG GAA CAA GTG AGA CAA ATG GAG ATA GCC AAA CAA AAT TGG CTG GCA GAG CAA CAG AAA ATG CAG GAA CAA
      TCT GAG GTA GTC CTT GTT CAC TCT GTT TAC CTC TAT CGG TTT GTT TTA ACC GAC CGT CTC GTT GTC TTT TAC GTC CTT GTT
 520  R   L   H   Q   E   Q   V   R   Q   M   E   I   A   K   Q   N   W   L   A   E   Q   Q   K   M   Q   E   Q
1813  CAG ATG CAG GTA TTC ATC AAT TGT TTC ATC TCT CCC CTG CCT GTA ACG ATG AGA GTA TGT AGC AGT GGC AAA GAG GGA GAG
      GTC TAC GTC CAT AAG TAG TTA ACA AAG TAG AGA GGG GAC GGA CAT TGC TAC TCT CAT ACA TCG TCA CCG TTT CTC CCT CTC
 547  Q   M   Q   V   F   I   N   C   F   I   S   P   L   P   V   T   M   R   V   C   S   S   G   K   E   G   E
1894  GCA GCA AGA TCT TGT GGC TCT CAG CAG GGA GTC TGG AGC CAG AAA GTC TGG GTA TGA ATCCAAGCTC CACCTCTTAG TAAGTATATG
      CGT CGT TCT AGA ACA CCG AGA GTC GTC CCT CAG ACC TCG GTC TTT CAG ACC CAT ACT TAGGTTCGAG GTGGAGAATC ATTCATATAC
 574  A   A   R   S   C   G   S   Q   Q   G   V   W   S   Q   K   V   W   V   O
1981  GTTTAGGCAA GTTATCTATC ACCTCTGTGC CTAATTTTCC TCCG
      CAAATCCGTT CAATAGATAG TGGAGACACG GATTAAAAGG AGGC
```

FIG. 1

```
GBP-1    1  MASEIHMTGPMCLIENTNGRLMANPEALKILSAITQPMVVVAIVGLYRTG
GBP-2    1  MAPEINLPGPMSLIDNTKGQLVVNPEALKILSAITQPVVVVAIVGLYRTG
GBP-4    1  MALEIHMSDPMCLIENFNEQLKVNQEALEILSAITQPVVVVAIVGLYRTG

GBP-1   51  KSYLMNKLAGKKKGFSLGSTVQSHTKGIWMWCVPHPKKPGHILVLLDTEG
GBP-2   51  KSYLMNKLAGKKNGFSLGSTVKSHTKGIWMWCVPHPKKPEHTLVLLDTEG
GBP-4   51  KSYLMNKLAGKNKGFSVASTVQSHTKGIWIWCVPHPNWPNHTLVLLDTEG
                                                      ••
GBP-1  101  LGDVEKGDNQNDSWIFALAVLLSSTFVYNSIGTINQQAMDQLYYVTELTH
GBP-2  101  LGDIEKGDNENDSWIFALAILLSSTFVYNSMGTINQQAMDQLHYVTELTD
GBP-4  101  LGDVEKADNKNDIQIFALALLLSSTFVYNTVNKIDQGAIDLLHNVTELTD
                                  ••                 ••
GBP-1  151  RIRSKSSPDENENEVEDSADFVSFFPDFVWTLRDFSLDLEADGQPLTPDE
GBP-2  151  RIKANSSPG--NNSVDDSADFVSFFPAFVWTLRDFTLELEVDGEPITADD
GBP-4  151  LLKARNSPD--LDRVEDPADSASFFPDLVWTLRDFCLGLEIDGQLVTPDE
             ••
GBP-1  201  YLTYSLKLKKGTSQKDETFNLPRLCIRKFFPKKKCFVFDRPVHRRKLAQL
GBP-2  199  YLELSLKLRKGTDKKSKSFNDPRLCIRKFFPKRKCFVFDWPAPKKYLAHL
GBP-4  199  YLENSLRPKQGSDQRVQNFNLPRLCIQKFFPKKKCFIFDLPAHQKKLAQL

GBP-1  251  EKLQDEELDPEFVQQVADFCSYIFSNSKTKTLSGGIQVNGPRLESLVLTY
GBP-2  249  EQLKEEELNPDFIEQVAEFCSYILSHSNVKTLSGGIAVNGPRLESLVLTY
GBP-4  249  ETLPDDELEPEFVQQVTEFCSYIFSHSMTKTLPGGIMVNGSRLKNLVLTY

GBP-1  301  VNAISSGDLPCMENAVLALAQIENSAAVQKAIAHYEQQMGQKVQLPTESL
GBP-2  299  VNAISSGDLPCMENAVLALAQIENSAAVEKAIAHYEQQMGQKVQLPTETL
GBP-4  299  VNAISSGDLPCIENAVLALAQRENSAAVQKAIAHYDQQMGQKVQLPMETL

GBP-1  351  QELLDLHRDSEREAIEVFIRSSFKDVDHLFQKELAAQLEKKRDDFCKQNQ
GBP-2  349  QELLDLHRDSEREAIEVFMKNSFKDVDQMFQRKLGAQLEARRDDFCKQNS
GBP-4  349  QELLDLHRTSEREAIEVFMKNSFKDVDQSFQKELETLLDAKQNDICKRNL
                ••                                 ••
GBP-1  401  EASSDRCSGLLQVIFSPLEEEVKAGIYSKPGGYRLFVQKLQDLKKKYYEE
GBP-2  399  KASSDCCMALLQDIFGPLEEDVKQGTFSKPGGYRLFTQKLQELKNKYYQV
GBP-4  399  EASSDYCSALLKDIFGPLEEAVKQGIYSKPGGHNLFIQKTEELKAKYYRE
                     ••
GBP-1  451  PRKGIQAEEILQTYLKSKESMTDAILQTDQTLTEKEKEIEVERVKAESAQ
GBP-2  449  PRKGIQAKEVLKKYLESKEDVADALLQTDQSLSEKEKAIEVERIKAESAE
GBP-3    1  -----------------------------------------ECVKAESAQ
GBP-4  449  PRKGIQAEEVLQKYLKSKESVSHAILQTDQALTETEKKKKEAQVKAEAEK

GBP-1  501  ASAKMLQEMQRKNEQMMEQKERSYQEHLKQLTEKMENDRVQLLKEQERTL
GBP-2  499  AAKKMLEEIQKKNEEMMEQKEKSYQEHVKQLTEKMERDRAQLMAEQEKTL
GBP-3   10  ASAKMVEEMQIKYQQMMEEKEKSYQEHVKQLTEKMENDRVQLLKEQERTL
GBP-4  499  AEAQRLAAIQRQNEQMMQERERLHQEQVRQMEIAKQNWLAEQQKMQEQQM

GBP-1  551  ALKLQEQEQLLKEGFQKESRIMKNEIQDLQTKMRRRKA-CTIS
GBP-2  549  ALKLQEQERLLKEGFENESKRLQKDIWDIQMRSKSLEPICNIL
GBP-3   60  ALKLQ----------------------------------****
GBP-4  549  QVFINCFISPLPVTMRVCSSGKEGEAARSCGSQQGVWSQKVWV
                ****
```

FIG. 2

| Sequence | Position | Alignment |
|---|---|---|
| mouse.purine.nuc.BP | 1 | ----------MEAPICLVENWKNQLTVNLEAIRILEQIAQPLVVVAIVGL |
| mu.GBP1 | 1 | --MASEI--HMSEPMCLIENTEAQLVINQEALRILSAITQPVVVVAIVGL |
| rat.GBP.p67 | 1 | MDMASEI--HMLQPMCLIENTEAHLVINQEALRILSAINQPVVVVAIVGL |
| pig.GBP-1.partial | 1 | --NFHGIWSTTMDPIXLVKNQNNHLTVNPKALKILGEICQPVVVVIIAGL |
| pig.GBP-1.NH2.term. | 1 | --MASKV--HMPEPQCLIENINGRLAVNPKALKILSAIKQPLVVVAIVGL |
| chicken.GBP | 1 | --MDTPV-LPMPAPLRLVTNKDGVLALNTAALAVLRSVTQPVVVVAIAGP |
| GBP-4 | 1 | --MALEI--HMSDPMCLIENFNEQLKVNQEALEILSAITQPVVVVAIVGL |
| mouse.purine.nuc.BP | 41 | YRTGKSYLMNRLAGRNHGFSLGSTVQSETKGIWMWCVPHPTKPTHTLVLL |
| mu.GBP1 | 47 | YRTGKSYLMNKLAGKRTGFSLGSTVQSHTKGIWMWCVPHPKKAGQTLVLL |
| rat.GBP.p67 | 49 | YRTGKSYLMNKLAGKRTGFSLGSTVQSHTKGIWMWCVPHPKKAGQTLVLL |
| pig.GBP-1.partial | 49 | YRTGKSYLMNRLAGQNHGFRLGSTVRSETKGIXMWCVPHPXKXDHILVLL |
| pig.GBP-1.NH2.term. | 47 | YRTGKSYLMNKLAXKNKG-------------------------------- |
| chicken.GBP | 48 | YRTGKSFLMNRLAQKRTGFPLGPTVYAETKGIWMWCLPHPRQPRVTLVLL |
| GBP-4 | 47 | YRTGKSYLMNKLAGKNKGFSVASTVQSHTKGIWIWCVPHPNWPNHTLVLL |
| mouse.purine.nuc.BP | 91 | DTEGLGDVEKGDPKNDSWIFALAVLLSSTFVYNSMSTINQQALEQLHFVT |
| mu.GBP1 | 97 | DTEGLEDVEKGDNQNDCWIFALAVLLSSTFIYNSIGTINQQAMDQLHYVT |
| rat.GBP.p67 | 99 | DTEGLEDVEKGDNQNDCWIFALAVLLSSTFVYNSMGTINQQAMDQLHYVT |
| pig.GBP-1.partial | 99 | GT------------------------------------------------ |
| chicken.GBP | 96 | DTEGLEDPNKDNDHSDAWIFILALLLSSTLVYNSVGTIDQRALS----SC |
| GBP-4 | 97 | DTEGLGDVEKADNKNDIQIFALALLLSSTFVYNTVNKIDQGAIDLLHNVT |
| mouse.purine.nuc.BP | 141 | ELTQLIRAKSSPREDKVKDSSEFVGFFPDFIWAVRDFALELKLNGRPITE |
| mu.GBP1 | 147 | ELTDLIKSKSSPDQSDVDNSANFVGFFPIFVWTLRDFSLDLEFDGESITP |
| rat.GBP.p67 | 149 | ELTDLIKSKSSPDQSGIDDSANFVGFFPTFVWALRDFSLELEVNGKLVTP |
| chicken.GBP | 144 | AGNGAVRAHPRGEKDN-NPASNFVSIFPGFVWTVRDFTLQLRDGEKTLSE |
| GBP-4 | 147 | ELTDLLKARNSPDLDRVEDPADSASFFPDLVWTLRDFCLGLEIDGQLVTP |
| mouse.purine.nuc.BP | 191 | DEYLENALKLIQGDNLKVQQSNMTRECIRYFFPVRKCFVFDRPTSDKRLL |
| mu.GBP1 | 197 | DEYLETSLALRKGTDENTKKFNMPRLCIRKFFPKRKCFIFDRPGDRKQ-L |
| rat.GBP.p67 | 199 | DEYLEHSLTLKKGADKKTKSFNEPRLCIRKFFPKRKCFIFDRPALRKQ-L |
| chicken.GBP | 193 | DEYLEDVLRLRPGAGRRQERNELRR-CLPNFFPRRKLFTMERPAADAN-L |
| GBP-4 | 197 | DEYLENSLRPKQGSDQRVQNFNLPRLCIQKFFPKKKCFIFDLPAHQKK-L |
| mouse.purine.nuc.BP | 241 | LQIENVPENQLERNFQVESEKFCSYIFTNGKTKTLRGGVIVTGNRLGTLV |
| mu.GBP1 | 246 | SKLEWIQEDQLNKEFVEQVAEFTSYIFSYSGVKTLSGGITVNGPRLKSLV |
| rat.GBP.p67 | 248 | CKLETLGEEELCSEFVEQVAEFTSYIFSYSAVKTLSGGIIVNGPRLKSLV |
| chicken.GBP | 241 | TRLEELREDELQPGFRKQVDAFCRYIWEEAPVKVLPGGHQVTGSALAYLV |
| GBP-4 | 246 | AQLETLPDDELEPEFVQQVTEFCSYIFSHSMTKTLPGGIMVNGSRLKNLV |
| mouse.purine.nuc.BP | 291 | QTYVNAINSGTVPCLENAVTTLAQRENSIAVQKAADHYSEQMAQRMRLPT |
| mu.GBP1 | 296 | QTYVSAICSGELPCMENAVLTLAQIENSAAVQKAITYYEEQMNQKIHMPT |
| rat.GBP.p67 | 298 | QTYVGAISSGSLPCMESAVLTLAQIENSAAVQKAITHYEEQMNQKIQMPT |
| chicken.GBP | 291 | EKYMAAISSGSVPCVESTLKALAQAENTAAVQMAVAEYQRGMEQGLVLPT |
| GBP-4 | 296 | LTYVNAISSGDLPCIENAVLALAQRENSAAVQKAIAHYDQQMGQKVQLPM |
| mouse.purine.nuc.BP | 341 | DTLQELLTVHAACEKEAIAVFMEHSFKDDEQEFQKKLVVTIEERKEEFIR |
| mu.GBP1 | 346 | ETLQELLDLHRTCEREAIEVFMKNSFKDVDQKFQEELGAQLEAKRDAFVK |
| rat.GBP.p67 | 348 | ETLQELLDLHRLIEREAIEIFLKNSFKDVDQKFQTELGNLLISKRDAFIK |
| chicken.GBP | 341 | ASYDALLAVHRDCEQRALALFLSRAFADHKHQYHDELVHKLEGQRGVLPA |
| GBP-4 | 346 | ETLQELLDLHRTSEREAIEVFMKNSFKDVDQSFQKELETLLDAKQNDICK |
| mouse.purine.nuc.BP | 391 | QNEAASIRHCQAELERLSESLRKSISCGAFSVPGGHSLYLEARKKIELGY |
| mu.GBP1 | 396 | KNMDMSSAHCSDLLEGLFAHLEEEVKQGTFYKPGGYYLFLQRKQELEKKY |
| rat.GBP.p67 | 398 | KNSDVSSAHCSDLIEDIFGPLEEEVKQGTFSKPGGYFLFLQMRQELEKKY |
| chicken.GBP | 391 | QQGGVGAAVPHGAAGAVEGR-GRRLQRGDYVARGGAQLFKEDVNRVLEEY |
| GBP-4 | 396 | RNLEASSDYCSALLKDFFGPLEEAVKQGIYSKPGGHNLFIQKTEELKAKY |

FIG. 3A

```
mouse.purine.nuc.BP 441 QQVLRKGLKAKEVLKSFLQSQAIMEDSILQSDKALTDGERAIAAERTKKE
mu.GBP1             446 IQTPGKGLQAEVMLRKYFESKEDLADTLLKMDQSLTEKEKQIEMERIKAE
rat.GBP.p67         448 NQAPGKGLEAEAVLKKYFESKEDIVETLLKTDQSLTEAAKEIEVERIKAE
pig.GBP-1.partial   101 ----PRG-------------------------------------------
chicken.GBP         440 KQRPDKGVRAEAVLKEFLREHEGLAQVLKATEVQLELAERQQEAAAAEAE
GBP-4               446 YREPRKGIQAEEVLQKYLKSKESVSHAILQTDQALTETEKKKKEAQVKAE

mouse.purine.nuc.BP 491 VAEKELELLRQRQKEQEQVMEAQERSFRENIAKLQEKMES---EKEMLLR
mu.GBP1             496 AAEAANRALAEMQKKHEMLMEQKEQSYQEHMKQLTEKMEQ---ERKELMA
rat.GBP.p67         498 TAEAANRELAEKQEKFELMMQQKEESYQEHVRQLTEKMKE---EQKKLIE
chicken.GBP         490 AARKATEAWREDQK----------RSMEEHKRQLEQWMKK---EKHTWEE
GBP-4               496 AEKAEAQRLAAIQRQNEQMMQEREERLHQEQVRQMEIAKQNWLAEQQKMQE

mouse.purine.nuc.BP 538 EQEKMLEHKLKVQEELLIEGFREKSDMLKNEISHLREEMERTRRKPSLFG
mu.GBP1             543 EQQRIISLKLQEQERLLKQGFQNESLQLRQEIEKIK-NMPPPRS------
rat.GBP.p67         545 EQDNIIALKLREQEKFLREGYENESKKLLREIENMK-RRQSPGK------
chicken.GBP         527 ELNRMLEHHRKEYKALLQEGFRREAAAKEKQIRELQEEMRSCN-------
GBP-4               546 QQMQVFINCFISPLPVTMRVCSSGKEGEAARSCGSQ-QGVWSQK------

mouse.purine.nuc.BP 588 QILDTIGNAFIMILPGAGKLFGVGLKFLGSLSS
mu.GBP1             586 ----------CTIL-------------------
rat.GBP.p67         588 ----------CTIL-------------------
chicken.GBP         570 ----------CTVL-------------------
GBP-4               589 ----------VWV--------------------
```

FIG. 3B

| hGBP-4 | | | | | | |
|---|---|---|---|---|---|---|
| 67 | hGBP-1 | | | | | |
| 64 | 76 | hGBP-2 | | | | |
| 60 | 68 | 71 | rGBP | | | |
| 59 | 70 | 71 | 80 | mGBP-1 | | |
| 49 | 54 | 54 | 52 | 53 | mPNBP | |
| 37 | 41 | 41 | 41 | 39 | 41 | cGBP |

FIG. 4

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
(A) LENGTH: 2024 base pairs
(B) TYPE: Nucleic Acid
(C) STRANDEDNESS: Single
(D) TOPOLOGY: Linear (xi) SEQUENCE DESCRIPTION: SEQ ID NO: 1:

```
GAACCCACCA GAAGGAAGAA ACTCCAAACA CATCCGAACA TCAGAAGGAG    50

CAAACTCGTG ACACGCCACC TTTAAGAACC GTGACACTCA ACGCTAGGGT   100

CCGCGGCTTC ATTCTTGAAG TCAGTGAGAC CAAGAACCCA CCAATTCCGG   150

ACACGGCAAA GTAACATCCT AGACATGGCT TTAGAGATCC ACATGTCAGA   200

CCCCATGTGC CTCATCGAGA ACTTTAATGA GCAGCTGAAG GTTAATCAGG   250

AAGCTTTGGA GATCCTGTCT GCCATTACGC AACCTGTAGT TGTGGTAGCG   300

ATTGTGGGCC TCTATCGCAC TGGCAAATCC TACCTGATGA ACAAGCTGGC   350

TGGGAAGAAC AAGGGCTTCT CTGTTGCATC TACGGTGCAG TCTCACACCA   400

AGGGAATTTG GATATGGTGT GTGCCTCATC CCAACTGGCC AAATCACACA   450

TTAGTTCTGC TTGACACCGA GGGCCTGGGA GATGTAGAGA AGGCTGACAA   500

CAAGAATGAT ATCCAGATCT TTGCACTGGC ACTCTTACTG AGCAGCACCT   550

TTGTGTACAA TACTGTGAAC AAAATTGATC AGGGTGCTAT CGACCTACTG   600

CACAATGTGA CAGAACTGAC AGATCTGCTC AAGGCAAGAA ACTCACCCGA   650

CCTTGACAGG GTTGAAGATC CTGCTGACTC TGCGAGCTTC TTCCCAGACT   700

TAGTGTGGAC TCTGAGAGAT TTCTGCTTAG GCCTGGAAAT AGATGGGCAA   750
```

-continued

```
CTTGTCACAC CAGATGAATA CCTGGAGAAT TCCCTAAGGC CAAAGCAAGG      800
TAGTGATCAA AGAGTTCAAA ATTTCAATTT GCCCCGTCTG TGTATACAGA      850
AGTTCTTTCC AAAAAAGAAA TGCTTTATCT TTGACTTACC TGCTCACCAA      900
AAAAAGCTTG CCCAACTTGA AACACTGCCT GATGATGAGC TAGAGCCTGA      950
ATTTGTGCAA CAAGTGACAG AATTCTGTTC CTACATCTTT AGCCATTCTA     1000
TGACCAAGAC TCTTCCAGGT GGCATCATGG TCAATGGATC TCGTCTAAAG     1050
AACCTGGTGC TGACCTATGT CAATGCCATC AGCAGTGGGG ATCTGCCTTG     1100
CATAGAGAAT GCAGTCCTGG CCTTGGCTCA GAGAGAGAAC TCAGCTGCAG     1150
TGCAAAAGGC CATTGCCCAC TATGACCAGC AAATGGGCCA GAAAGTGCAG     1200
CTGCCCATGG AAACCCTCCA GGAGCTGCTG GACCTGCACA GGACCAGTGA     1250
GAGGGAGGCC ATTGAAGTCT TCATGAAAAA CTCTTTCAAG GATGTAGACC     1300
AAAGTTTCCA GAAAGAATTG GAGACTCTAC TAGATGCAAA ACAGAATGAC     1350
ATTTGTAAAC GGAACCTGGA AGCATCCTCG GATTATTGCT CGGCTTTACT     1400
TAAGGATATT TTTGGTCCTC TAGAAGAAGC AGTGAAGCAG GGAATTTATT     1450
CTAAGCCAGG AGGCCATAAT CTCTTCATTC AGAAAACAGA AGAACTGAAG     1500
GCAAAGTACT ATCGGGAGCC TCGGAAAGGA ATACAGGCTG AAGAAGTTCT     1550
GCAGAAATAT TTAAAGTCCA AGGAGTCTGT GAGTCATGCA ATATTACAGA     1600
CTGACCAGGC TCTCACAGAG ACGGAAAAAA AGAAGAAAGA GGCACAAGTG     1650
AAAGCAGAAG CTGAAAAGGC TGAAGCGCAA AGGTTGGCGG CGATTCAAAG     1700
GCAGAACGAG CAAATGATGC AGGAGAGGGA GAGACTCCAT CAGGAACAAG     1750
TGAGACAAAT GGAGATAGCC AAACAAAATT GGCTGGCAGA GCAACAGAAA     1800
ATGCAGGAAC AACAGATGCA GGTATTCATC AATTGTTTCA TCTCTCCCCT     1850
GCCTGTAACG ATGAGAGTAT GTAGCAGTGG CAAAGAGGGA GAGGCAGCAA     1900
GATCTTGTGG CTCTCAGCAG GGAGTCTGGA GCCAGAAAGT CTGGGTATGA     1950
ATCCAAGCTC CACCTCTTAG TAAGTATATG GTTTAGGCAA GTTATCTATC     2000
ACCTCTGTGC CTAATTTTCC TCCG 2024
```

(2) INFORMATION FOR SEQ ID NO: 2:

(i) SEQUENCE CHARACTERISTICS:
(A) LENGTH: 2024 base pairs
(B) TYPE: Nucleic Acid
(C) STRANDEDNESS: Single
(D) TOPOLOGY: Linear (xi) SEQUENCE DESCRIPTION: SEQ ID NO: 2:

```
CGGAGGAAAA TTAGGCACAG AGGTGATAGA TAACTTGCCT AAACCATATA       50
CTTACTAAGA GGTGGAGCTT GGATTCATAC CCAGACTTTC TGGCTCCAGA      100
CTCCCTGCTG AGAGCCACAA GATCTTGCTG CCTCTCCCTC TTTGCCACTG      150
CTACATACTC TCATCGTTAC AGGCAGGGGA GAGATGAAAC AATTGATGAA      200
TACCTGCATC TGTTGTTCCT GCATTTTCTG TTGCTCTGCC AGCCAATTTT      250
GTTTGGCTAT CTCCATTTGT CTCACTTGTT CCTGATGGAG TCTCTCCCTC      300
TCCTGCATCA TTTGCTCGTT CTGCCTTTGA ATCGCCGCCA ACCTTTGCGC      350
TTCAGCCTTT TCAGCTTCTG CTTTCACTTG TGCCTCTTTC TTCTTTTTTT      400
```

-continued

```
CCGTCTCTGT GAGAGCCTGG TCAGTCTGTA ATATTGCATG ACTCACAGAC        450

TCCTTGGACT TTAAATATTT CTGCAGAACT TCTTCAGCCT GTATTCCTTT        500

CCGAGGCTCC CGATAGTACT TTGCCTTCAG TTCTTCTGTT TTCTGAATGA        550

AGAGATTATG GCCTCCTGGC TTAGAATAAA TTCCCTGCTT CACTGCTTCT        600

TCTAGAGGAC CAAAAATATC CTTAAGTAAA GCCGAGCAAT AATCCGAGGA        650

TGCTTCCAGG TTCCGTTTAC AAATGTCATT CTGTTTTGCA TCTAGTAGAG        700

TCTCCAATTC TTTCTGGAAA CTTTGGTCTA CATCCTTGAA AGAGTTTTTC        750

ATGAAGACTT CAATGGCCTC CCTCTCACTG GTCCTGTGCA GGTCCAGCAG        800

CTCCTGGAGG GTTTCCATGG GCAGCTGCAC TTTCTGGCCC ATTTGCTGGT        850

CATAGTGGGC AATGGCCTTT TGCACTGCAG CTGAGTTCTC TCTCTGAGCC        900

AAGGCCAGGA CTGCATTCTC TATGCAAGGC AGATCCCCAC TGCTGATGGC        950

ATTGACATAG GTCAGCACCA GGTTCTTTAG ACGAGATCCA TTGACCATGA       1000

TGCCACCTGG AAGAGTCTTG GTCATAGAAT GGCTAAAGAT GTAGGAACAG       1050

AATTCTGTCA CTTGTTGCAC AAATTCAGGC TCTAGCTCAT CATCAGGCAG       1100

TGTTTCAAGT TGGGCAAGCT TTTTTTGGTG AGCAGGTAAG TCAAAGATAA       1150

AGCATTTCTT TTTTGGAAAG AACTTCTGTA TACACAGACG GGGCAAATTG       1200

AAATTTTGAA CTCTTTGATC ACTACCTTGC TTTGGCCTTA GGGAATTCTC       1250

CAGGTATTCA TCTGGTGTGA CAAGTTGCCC ATCTATTTCC AGGCCTAAGC       1300

AGAAATCTCT CAGAGTCCAC ACTAAGTCTG GGAAGAAGCT CGCAGAGTCA       1350

GCAGGATCTT CAACCCTGTC AAGGTCGGGT GAGTTTCTTG CCTTGAGCAG       1400

ATCTGTCAGT TCTGTCACAT TGTGCAGTAG GTCGATAGCA CCCTGATCAA       1450

TTTTGTTCAC AGTATTGTAC ACAAAGGTGC TGCTCAGTAA GAGTGCCAGT       1500

GCAAAGATCT GGATATCATT CTTGTTGTCA GCCTTCTCTA CATCTCCCAG       1550

GCCCTCGGTG TCAAGCAGAA CTAATGTGTG ATTTGGCCAG TTGGGATGAG       1600

GCACACACCA TATCCAAATT CCCTTGGTGT GAGACTGCAC CGTAGATGCA       1650

ACAGAGAAGC CCTTGTTCTT CCCAGCCAGC TTGTTCATCA GGTAGGATTT       1700

GCCAGTGCGA TAGAGGCCCA CAATCGCTAC CACAACTACA GGTTGCGTAA       1750

TGGCAGACAG GATCTCCAAA GCTTCCTGAT TAACCTTCAG CTGCTCATTA       1800

AAGTTCTCGA TGAGGCACAT GGGGTCTGAC ATGTGGATCT CTAAAGCCAT       1850

GTCTAGGATG TTACTTTGCC GTGTCCGGAA TTGGTGGGTT CTTGGTCTCA       1900

CTGACTTCAA GAATGAAGCC GCGGACCCTA GCGTTGAGTG TCACGGTTCT       1950

TAAAGGTGGC GTGTCACGAG TTTGCTCCTT CTGATGTTCG GATGTGTTTG       2000

GAGTTTCTTC CTTCTGGTGG GTTC                                   2024
```

(2) INFORMATION FOR SEQ ID NO: 3:

(i) SEQUENCE CHARACTERISTICS:
(A) LENGTH: 591 amino acids
(B) TYPE: Amino Acid
(D) TOPOLOGY: Linear (xi) SEQUENCE DESCRIPTION: SEQ ID NO: 3:

```
Met Ala Leu Glu Ile His Met Ser Asp Pro Met Cys Leu Ile Glu
  1               5                  10                  15
```

```
Asn Phe Asn Glu Gln Leu Lys Val Asn Gln Glu Ala Leu Glu Ile
                20                  25                  30

Leu Ser Ala Ile Thr Gln Pro Val Val Val Val Ala Ile Val Gly
                35                  40                  45

Leu Tyr Arg Thr Gly Lys Ser Tyr Leu Met Asn Lys Leu Ala Gly
                50                  55                  60

Lys Asn Lys Gly Phe Ser Val Ala Ser Thr Val Gln Ser His Thr
                65                  70                  75

Lys Gly Ile Trp Ile Trp Cys Val Pro His Pro Asn Trp Pro Asn
                80                  85                  90

His Thr Leu Val Leu Leu Asp Thr Glu Gly Leu Gly Asp Val Glu
                95                 100                 105

Lys Ala Asp Asn Lys Asn Asp Ile Gln Ile Phe Ala Leu Ala Leu
               110                 115                 120

Leu Leu Ser Ser Thr Phe Val Tyr Asn Thr Val Asn Lys Ile Asp
               125                 130                 135

Gln Gly Ala Ile Asp Leu Leu His Asn Val Thr Glu Leu Thr Asp
               140                 145                 150

Leu Leu Lys Ala Arg Asn Ser Pro Asp Leu Asp Arg Val Glu Asp
               155                 160                 165

Pro Ala Asp Ser Ala Ser Phe Phe Pro Asp Leu Val Trp Thr Leu
               170                 175                 180

Arg Asp Phe Cys Leu Gly Leu Glu Ile Asp Gly Gln Leu Val Thr
               185                 190                 195

Pro Asp Glu Tyr Leu Glu Asn Ser Leu Arg Pro Lys Gln Gly Ser
               200                 205                 210

Asp Gln Arg Val Gln Asn Phe Asn Leu Pro Arg Leu Cys Ile Gln
               215                 220                 225

Lys Phe Phe Pro Lys Lys Lys Cys Phe Ile Phe Asp Leu Pro Ala
               230                 235                 240

His Gln Lys Lys Leu Ala Gln Leu Glu Thr Leu Pro Asp Asp Glu
               245                 250                 255

Leu Glu Pro Glu Phe Val Gln Gln Val Thr Glu Phe Cys Ser Tyr
               260                 265                 270

Ile Phe Ser His Ser Met Thr Lys Thr Leu Pro Gly Gly Ile Met
               275                 280                 285

Val Asn Gly Ser Arg Leu Lys Asn Leu Val Leu Thr Tyr Val Asn
               290                 295                 300

Ala Ile Ser Ser Gly Asp Leu Pro Cys Ile Glu Asn Ala Val Leu
               305                 310                 315

Ala Leu Ala Gln Arg Glu Asn Ser Ala Ala Val Gln Lys Ala Ile
               320                 325                 330

Ala His Tyr Asp Gln Gln Met Gly Gln Lys Val Gln Leu Pro Met
               335                 340                 345

Glu Thr Leu Gln Glu Leu Leu Asp Leu His Arg Thr Ser Glu Arg
               350                 355                 360

Glu Ala Ile Glu Val Phe Met Lys Asn Ser Phe Lys Asp Val Asp
               365                 370                 375

Gln Ser Phe Gln Lys Glu Leu Glu Thr Leu Leu Asp Ala Lys Gln
               380                 385                 390

Asn Asp Ile Cys Lys Arg Asn Leu Glu Ala Ser Ser Asp Tyr Cys
               395                 400                 405
```

-continued

```
Ser Ala Leu Leu Lys Asp Ile Phe Gly Pro Leu Glu Glu Ala Val
                410                 415                 420

Lys Gln Gly Ile Tyr Ser Lys Pro Gly Gly His Asn Leu Phe Ile
                425                 430                 435

Gln Lys Thr Glu Glu Leu Lys Ala Lys Tyr Tyr Arg Glu Pro Arg
                440                 445                 450

Lys Gly Ile Gln Ala Glu Glu Val Leu Gln Lys Tyr Leu Lys Ser
                455                 460                 465

Lys Glu Ser Val Ser His Ala Ile Leu Gln Thr Asp Gln Ala Leu
                470                 475                 480

Thr Glu Thr Glu Lys Lys Lys Lys Glu Ala Gln Val Lys Ala Glu
                485                 490                 495

Ala Glu Lys Ala Glu Ala Gln Arg Leu Ala Ala Ile Gln Arg Gln
                500                 505                 510

Asn Glu Gln Met Met Gln Glu Arg Glu Arg Leu His Gln Glu Gln
                515                 520                 525

Val Arg Gln Met Glu Ile Ala Lys Gln Asn Trp Leu Ala Glu Gln
                530                 535                 540

Gln Lys Met Gln Glu Gln Gln Met Gln Val Phe Ile Asn Cys Phe
                545                 550                 555

Ile Ser Pro Leu Pro Val Thr Met Arg Val Cys Ser Ser Gly Lys
                560                 565                 570

Glu Gly Glu Ala Ala Arg Ser Cys Gly Ser Gln Gln Gly Val Trp
                575                 580                 585

Ser Gln Lys Val Trp Val
                590 591
```

(2) INFORMATION FOR SEQ ID NO: 4:

(i) SEQUENCE CHARACTERISTICS:
(A) LENGTH: 592 amino acids
(B) TYPE: Amino Acid
(D) TOPOLOGY: Linear (xi) SEQUENCE DESCRIPTION: SEQ ID NO: 4:

```
Met Ala Ser Glu Ile His Met Thr Gly Pro Met Cys Leu Ile Glu
  1               5                  10                  15

Asn Thr Asn Gly Arg Leu Met Ala Asn Pro Glu Ala Leu Lys Ile
                 20                  25                  30

Leu Ser Ala Ile Thr Gln Pro Met Val Val Val Ala Ile Val Gly
                 35                  40                  45

Leu Tyr Arg Thr Gly Lys Ser Tyr Leu Met Asn Lys Leu Ala Gly
                 50                  55                  60

Lys Lys Lys Gly Phe Ser Leu Gly Ser Thr Val Gln Ser His Thr
                 65                  70                  75

Lys Gly Ile Trp Met Trp Cys Val Pro His Pro Lys Lys Pro Gly
                 80                  85                  90

His Ile Leu Val Leu Leu Asp Thr Glu Gly Leu Gly Asp Val Glu
                 95                 100                 105

Lys Gly Asp Asn Gln Asn Asp Ser Trp Ile Phe Ala Leu Ala Val
                110                 115                 120

Leu Leu Ser Ser Thr Phe Val Tyr Asn Ser Ile Gly Thr Ile Asn
                125                 130                 135

Gln Gln Ala Met Asp Gln Leu Tyr Tyr Val Thr Glu Leu Thr His
                140                 145                 150
```

-continued

```
Arg Ile Arg Ser Lys Ser Ser Pro Asp Glu Asn Glu Asn Glu Val
                155                 160                 165

Glu Asp Ser Ala Asp Phe Val Ser Phe Phe Pro Asp Phe Val Trp
                170                 175                 180

Thr Leu Arg Asp Phe Ser Leu Asp Leu Glu Ala Asp Gly Gln Pro
                185                 190                 195

Leu Thr Pro Asp Glu Tyr Leu Thr Tyr Ser Leu Lys Leu Lys Lys
                200                 205                 210

Gly Thr Ser Gln Lys Asp Glu Thr Phe Asn Leu Pro Arg Leu Cys
                215                 220                 225

Ile Arg Lys Phe Phe Pro Lys Lys Lys Cys Phe Val Phe Asp Arg
                230                 235                 240

Pro Val His Arg Arg Lys Leu Ala Gln Leu Glu Lys Leu Gln Asp
                245                 250                 255

Glu Glu Leu Asp Pro Glu Phe Val Gln Gln Val Ala Asp Phe Cys
                260                 265                 270

Ser Tyr Ile Phe Ser Asn Ser Lys Thr Lys Thr Leu Ser Gly Gly
                275                 280                 285

Ile Gln Val Asn Gly Pro Arg Leu Glu Ser Leu Val Leu Thr Tyr
                290                 295                 300

Val Asn Ala Ile Ser Ser Gly Asp Leu Pro Cys Met Glu Asn Ala
                305                 310                 315

Val Leu Ala Leu Ala Gln Ile Glu Asn Ser Ala Ala Val Gln Lys
                320                 325                 330

Ala Ile Ala His Tyr Glu Gln Gln Met Gly Gln Lys Val Gln Leu
                335                 340                 345

Pro Thr Glu Ser Leu Gln Glu Leu Leu Asp Leu His Arg Asp Ser
                350                 355                 360

Glu Arg Glu Ala Ile Glu Val Phe Ile Arg Ser Ser Phe Lys Asp
                365                 370                 375

Val Asp His Leu Phe Gln Lys Glu Leu Ala Ala Gln Leu Glu Lys
                380                 385                 390

Lys Arg Asp Asp Phe Cys Lys Gln Asn Gln Glu Ala Ser Ser Asp
                395                 400                 405

Arg Cys Ser Gly Leu Leu Gln Val Ile Phe Ser Pro Leu Glu Glu
                410                 415                 420

Glu Val Lys Ala Gly Ile Tyr Ser Lys Pro Gly Gly Tyr Arg Leu
                425                 430                 435

Phe Val Gln Lys Leu Gln Asp Leu Lys Lys Lys Tyr Tyr Glu Glu
                440                 445                 450

Pro Arg Lys Gly Ile Gln Ala Glu Glu Ile Leu Gln Thr Tyr Leu
                455                 460                 465

Lys Ser Lys Glu Ser Met Thr Asp Ala Ile Leu Gln Thr Asp Gln
                470                 475                 480

Thr Leu Thr Glu Lys Glu Lys Glu Ile Glu Val Glu Arg Val Lys
                485                 490                 495

Ala Glu Ser Ala Gln Ala Ser Ala Lys Met Leu Gln Glu Met Gln
                500                 505                 510

Arg Lys Asn Glu Gln Met Met Glu Gln Lys Glu Arg Ser Tyr Gln
                515                 520                 525

Glu His Leu Lys Gln Leu Thr Glu Lys Met Glu Asn Asp Arg Val
                530                 535                 540

Gln Leu Leu Lys Glu Gln Glu Arg Thr Leu Ala Leu Lys Leu Gln
```

-continued

```
                545                 550                 555

Glu Gln Glu Gln Leu Leu Lys Glu Gly Phe Gln Lys Glu Ser Arg
                560                 565                 570

Ile Met Lys Asn Glu Ile Gln Asp Leu Gln Thr Lys Met Arg Arg
                575                 580                 585

Arg Lys Ala Cys Thr Ile Ser
                590     592
```

(2) INFORMATION FOR SEQ ID NO: 5:

(i) SEQUENCE CHARACTERISTICS:
(A) LENGTH: 591 amino acids
(B) TYPE: Amino Acid
(D) TOPOLOGY: Linear (xi) SEQUENCE DESCRIPTION: SEQ ID NO: 5:

```
Met Ala Pro Glu Ile Asn Leu Pro Gly Pro Met Ser Leu Ile Asp
  1               5                  10                  15

Asn Thr Lys Gly Gln Leu Val Val Asn Pro Glu Ala Leu Lys Ile
                 20                  25                  30

Leu Ser Ala Ile Thr Gln Pro Val Val Val Val Ala Ile Val Gly
                 35                  40                  45

Leu Tyr Arg Thr Gly Lys Ser Tyr Leu Met Asn Lys Leu Ala Gly
                 50                  55                  60

Lys Lys Asn Gly Phe Ser Leu Gly Ser Thr Val Lys Ser His Thr
                 65                  70                  75

Lys Gly Ile Trp Met Trp Cys Val Pro His Pro Lys Lys Pro Glu
                 80                  85                  90

His Thr Leu Val Leu Leu Asp Thr Glu Gly Leu Gly Asp Ile Glu
                 95                 100                 105

Lys Gly Asp Asn Glu Asn Asp Ser Trp Ile Phe Ala Leu Ala Ile
                110                 115                 120

Leu Leu Ser Ser Thr Phe Val Tyr Asn Ser Met Gly Thr Ile Asn
                125                 130                 135

Gln Gln Ala Met Asp Gln Leu His Tyr Val Thr Glu Leu Thr Asp
                140                 145                 150

Arg Ile Lys Ala Asn Ser Ser Pro Gly Asn Asn Ser Val Asp Asp
                155                 160                 165

Ser Ala Asp Phe Val Ser Phe Phe Pro Ala Phe Val Trp Thr Leu
                170                 175                 180

Arg Asp Phe Thr Leu Glu Leu Glu Val Asp Gly Glu Pro Ile Thr
                185                 190                 195

Ala Asp Asp Tyr Leu Glu Leu Ser Leu Lys Leu Arg Lys Gly Thr
                200                 205                 210

Asp Lys Lys Ser Lys Ser Phe Asn Asp Pro Arg Leu Cys Ile Arg
                215                 220                 225

Lys Phe Phe Pro Lys Arg Lys Cys Phe Val Phe Asp Trp Pro Ala
                230                 235                 240

Pro Lys Lys Tyr Leu Ala His Leu Glu Gln Leu Lys Glu Glu Glu
                245                 250                 255

Leu Asn Pro Asp Phe Ile Glu Gln Val Ala Glu Phe Cys Ser Tyr
                260                 265                 270

Ile Leu Ser His Ser Asn Val Lys Thr Leu Ser Gly Gly Ile Ala
                275                 280                 285

Val Asn Gly Pro Arg Leu Glu Ser Leu Val Leu Thr Tyr Val Asn
```

-continued

```
                290                 295                 300

Ala Ile Ser Ser Gly Asp Leu Pro Cys Met Glu Asn Ala Val Leu
                305                 310                 315

Ala Leu Ala Gln Ile Glu Asn Ser Ala Ala Val Glu Lys Ala Ile
                320                 325                 330

Ala His Tyr Glu Gln Gln Met Gly Gln Lys Val Gln Leu Pro Thr
                335                 340                 345

Glu Thr Leu Gln Glu Leu Leu Asp Leu His Arg Asp Ser Glu Arg
                350                 355                 360

Glu Ala Ile Glu Val Phe Met Lys Asn Ser Phe Lys Asp Val Asp
                365                 370                 375

Gln Met Phe Gln Arg Lys Leu Gly Ala Gln Leu Glu Ala Arg Arg
                380                 385                 390

Asp Asp Phe Cys Lys Gln Asn Ser Lys Ala Ser Ser Asp Cys Cys
                395                 400                 405

Met Ala Leu Leu Gln Asp Ile Phe Gly Pro Leu Glu Glu Asp Val
                410                 415                 420

Lys Gln Gly Thr Phe Ser Lys Pro Gly Gly Tyr Arg Leu Phe Thr
                425                 430                 435

Gln Lys Leu Gln Glu Leu Lys Asn Lys Tyr Tyr Gln Val Pro Arg
                440                 445                 450

Lys Gly Ile Gln Ala Lys Glu Val Leu Lys Lys Tyr Leu Glu Ser
                455                 460                 465

Lys Glu Asp Val Ala Asp Ala Leu Leu Gln Thr Asp Gln Ser Leu
                470                 475                 480

Ser Glu Lys Glu Lys Ala Ile Glu Val Glu Arg Ile Lys Ala Glu
                485                 490                 495

Ser Ala Glu Ala Ala Lys Lys Met Leu Glu Glu Ile Gln Lys Lys
                500                 505                 510

Asn Glu Glu Met Met Glu Gln Lys Glu Lys Ser Tyr Gln Glu His
                515                 520                 525

Val Lys Gln Leu Thr Glu Lys Met Glu Arg Asp Arg Ala Gln Leu
                530                 535                 540

Met Ala Glu Gln Glu Lys Thr Leu Ala Leu Lys Leu Gln Glu Gln
                545                 550                 555

Glu Arg Leu Leu Lys Glu Gly Phe Glu Asn Glu Ser Lys Arg Leu
                560                 565                 570

Gln Lys Asp Ile Trp Asp Ile Gln Met Arg Ser Lys Ser Leu Glu
                575                 580                 585

Pro Ile Cys Asn Ile Leu
                590 591
```

(2) INFORMATION FOR SEQ ID NO: 6:

(i) SEQUENCE CHARACTERISTICS:
(A) LENGTH: 64 amino acids
(B) TYPE: Amino Acid
(D) TOPOLOGY: Linear (xi) SEQUENCE DESCRIPTION: SEQ ID NO: 6:

```
Glu Cys Val Lys Ala Glu Ser Ala Gln Ala Ser Ala Lys Met Val
  1               5                  10                  15

Glu Glu Met Gln Ile Lys Tyr Gln Gln Met Met Glu Glu Lys Glu
                 20                  25                  30

Lys Ser Tyr Gln Glu His Val Lys Gln Leu Thr Glu Lys Met Glu
```

-continued

```
              35                  40                  45

Asn Asp Arg Val Gln Leu Leu Lys Glu Gln Glu Arg Thr Leu Ala
              50                  55                  60

Leu Lys Leu Gln
          64
```

(2) INFORMATION FOR SEQ ID NO: 7:

(i) SEQUENCE CHARACTERISTICS:
(A) LENGTH: 8 amino acids
(B) TYPE: Amino Acid
(D) TOPOLOGY: Linear (xi) SEQUENCE DESCRIPTION: SEQ ID NO: 7:

```
Gly Xaa Xaa Xaa Xaa Gly Lys Ser
  1               5           8
```

(2) INFORMATION FOR SEQ ID NO: 8:

(i) SEQUENCE CHARACTERISTICS:
(A) LENGTH: 8 amino acids
(B) TYPE: Amino Acid
(D) TOPOLOGY: Linear (xi) SEQUENCE DESCRIPTION: SEQ ID NO: 8:

```
Gly Xaa Xaa Xaa Xaa Gly Lys Thr
  1               5           8
```

(2) INFORMATION FOR SEQ ID NO: 9:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO: 9:

```
Asp Xaa Xaa Gly
  1           4
```

(2) INFORMATION FOR SEQ ID NO: 10:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO: 10:

```
Asn Lys Xaa Asp
  1           4
```

(2) INFORMATION FOR SEQ ID NO: 11:

(i) SEQUENCE CHARACTERISTICS:
(A) LENGTH: 4 amino acids
(B) TYPE: Amino Acid
(D) TOPOLOGY: Linear (xi) SEQUENCE DESCRIPTION: SEQ ID NO: 11:

```
Thr Lys Xaa Asp
  1           4
```

(2) INFORMATION FOR SEQ ID NO: 12:

(i) SEQUENCE CHARACTERISTICS:
(A) LENGTH: 4 amino acids
(B) TYPE: Amino Acid

```
        (D) TOPOLOGY: Linear

   (xi) SEQUENCE DESCRIPTION: SEQ ID NO: 12:

Cys Xaa Xaa Xaa
 1          4


(2) INFORMATION FOR SEQ ID NO: 13:

    (i) SEQUENCE CHARACTERISTICS:
        (A) LENGTH: 620 amino acids
        (B) TYPE: Amino Acid
        (D) TOPOLOGY: Linear

   (xi) SEQUENCE DESCRIPTION: SEQ ID NO: 13:

Met Glu Ala Pro Ile Cys Leu Val Glu Asn Trp Lys Asn Gln Leu
 1               5                  10                  15

Thr Val Asn Leu Glu Ala Ile Arg Ile Leu Glu Gln Ile Ala Gln
                20                  25                  30

Pro Leu Val Val Val Ala Ile Val Gly Leu Tyr Arg Thr Gly Lys
                35                  40                  45

Ser Tyr Leu Met Asn Arg Leu Ala Gly Arg Asn His Gly Phe Ser
                50                  55                  60

Leu Gly Ser Thr Val Gln Ser Glu Thr Lys Gly Ile Trp Met Trp
                65                  70                  75

Cys Val Pro His Pro Thr Lys Pro Thr His Thr Leu Val Leu Leu
                80                  85                  90

Asp Thr Glu Gly Leu Gly Asp Val Glu Lys Gly Asp Pro Lys Asn
                95                 100                 105

Asp Ser Trp Ile Phe Ala Leu Ala Val Leu Leu Ser Ser Thr Phe
               110                 115                 120

Val Tyr Asn Ser Met Ser Thr Ile Asn Gln Gln Ala Leu Glu Gln
               125                 130                 135

Leu His Phe Val Thr Glu Leu Thr Gln Leu Ile Arg Ala Lys Ser
               140                 145                 150

Ser Pro Arg Glu Asp Lys Val Lys Asp Ser Ser Glu Phe Val Gly
               155                 160                 165

Phe Phe Pro Asp Phe Ile Trp Ala Val Arg Asp Phe Ala Leu Glu
               170                 175                 180

Leu Lys Leu Asn Gly Arg Pro Ile Thr Glu Asp Glu Tyr Leu Glu
               185                 190                 195

Asn Ala Leu Lys Leu Ile Gln Gly Asp Asn Leu Lys Val Gln Gln
               200                 205                 210

Ser Asn Met Thr Arg Glu Cys Ile Arg Tyr Phe Phe Pro Val Arg
               215                 220                 225

Lys Cys Phe Val Phe Asp Arg Pro Thr Ser Asp Lys Arg Leu Leu
               230                 235                 240

Leu Gln Ile Glu Asn Val Pro Glu Asn Gln Leu Glu Arg Asn Phe
               245                 250                 255

Gln Val Glu Ser Glu Lys Phe Cys Ser Tyr Ile Phe Thr Asn Gly
               260                 265                 270

Lys Thr Lys Thr Leu Arg Gly Gly Val Ile Val Thr Gly Asn Arg
               275                 280                 285

Leu Gly Thr Leu Val Gln Thr Tyr Val Asn Ala Ile Asn Ser Gly
               290                 295                 300

Thr Val Pro Cys Leu Glu Asn Ala Val Thr Thr Leu Ala Gln Arg
               305                 310                 315
```

-continued

```
Glu Asn Ser Ile Ala Val Gln Lys Ala Ala Asp His Tyr Ser Glu
                320                 325                 330

Gln Met Ala Gln Arg Met Arg Leu Pro Thr Asp Thr Leu Gln Glu
                335                 340                 345

Leu Leu Thr Val His Ala Ala Cys Glu Lys Glu Ala Ile Ala Val
                350                 355                 360

Phe Met Glu His Ser Phe Lys Asp Asp Glu Gln Glu Phe Gln Lys
                365                 370                 375

Lys Leu Val Val Thr Ile Glu Glu Arg Lys Glu Glu Phe Ile Arg
                380                 385                 390

Gln Asn Glu Ala Ala Ser Ile Arg His Cys Gln Ala Glu Leu Glu
                395                 400                 405

Arg Leu Ser Glu Ser Leu Arg Lys Ser Ile Ser Cys Gly Ala Phe
                410                 415                 420

Ser Val Pro Gly Gly His Ser Leu Tyr Leu Glu Ala Arg Lys Lys
                425                 430                 435

Ile Glu Leu Gly Tyr Gln Gln Val Leu Arg Lys Gly Val Lys Ala
                440                 445                 450

Lys Glu Val Leu Lys Ser Phe Leu Gln Ser Gln Ala Ile Met Glu
                455                 460                 465

Asp Ser Ile Leu Gln Ser Asp Lys Ala Leu Thr Asp Gly Glu Arg
                470                 475                 480

Ala Ile Ala Ala Glu Arg Thr Lys Lys Glu Val Ala Glu Lys Glu
                485                 490                 495

Leu Glu Leu Leu Arg Gln Arg Gln Lys Glu Gln Glu Gln Val Met
                500                 505                 510

Glu Ala Gln Glu Arg Ser Phe Arg Glu Asn Ile Ala Lys Leu Gln
                515                 520                 525

Glu Lys Met Glu Ser Glu Lys Glu Met Leu Leu Arg Glu Gln Glu
                530                 535                 540

Lys Met Leu Glu His Lys Leu Lys Val Gln Glu Glu Leu Leu Ile
                545                 550                 555

Glu Gly Phe Arg Glu Lys Ser Asp Met Leu Lys Asn Glu Ile Ser
                560                 565                 570

His Leu Arg Glu Glu Met Glu Arg Thr Arg Arg Lys Pro Ser Leu
                575                 580                 585

Phe Gly Gln Ile Leu Asp Thr Ile Gly Asn Ala Phe Ile Met Ile
                590                 595                 600

Leu Pro Gly Ala Gly Lys Leu Phe Gly Val Gly Leu Lys Phe Leu
                605                 610                 615

Gly Ser Leu Ser Ser
                620
```

(2) INFORMATION FOR SEQ ID NO: 14:

(i) SEQUENCE CHARACTERISTICS:
(A) LENGTH: 589 amino acids
(B) TYPE: Amino Acid
(D) TOPOLOGY: Linear (xi) SEQUENCE DESCRIPTION: SEQ ID NO: 14:

```
Met Ala Ser Glu Ile His Met Ser Glu Pro Met Cys Leu Ile Glu
  1               5                  10                  15

Asn Thr Glu Ala Gln Leu Val Ile Asn Gln Glu Ala Leu Arg Ile
                 20                  25                  30
```

-continued

```
Leu Ser Ala Ile Thr Gln Pro Val Val Val Val Ala Ile Val Gly
                35                  40                  45

Leu Tyr Arg Thr Gly Lys Ser Tyr Leu Met Asn Lys Leu Ala Gly
                50                  55                  60

Lys Arg Thr Gly Phe Ser Leu Gly Ser Thr Val Gln Ser His Thr
                65                  70                  75

Lys Gly Ile Trp Met Trp Cys Val Pro His Pro Lys Lys Ala Gly
                80                  85                  90

Gln Thr Leu Val Leu Leu Asp Thr Glu Gly Leu Glu Asp Val Glu
                95                  100                 105

Lys Gly Asp Asn Gln Asn Asp Cys Trp Ile Phe Ala Leu Ala Val
                110                 115                 120

Leu Leu Ser Ser Thr Phe Ile Tyr Asn Ser Ile Gly Thr Ile Asn
                125                 130                 135

Gln Gln Ala Met Asp Gln Leu His Tyr Val Thr Glu Leu Thr Asp
                140                 145                 150

Leu Ile Lys Ser Lys Ser Ser Pro Asp Gln Ser Asp Val Asp Asn
                155                 160                 165

Ser Ala Asn Phe Val Gly Phe Phe Pro Ile Phe Val Trp Thr Leu
                170                 175                 180

Arg Asp Phe Ser Leu Asp Leu Glu Phe Asp Gly Glu Ser Ile Thr
                185                 190                 195

Pro Asp Glu Tyr Leu Glu Thr Ser Leu Ala Leu Arg Lys Gly Thr
                200                 205                 210

Asp Glu Asn Thr Lys Lys Phe Asn Met Pro Arg Leu Cys Ile Arg
                215                 220                 225

Lys Phe Phe Pro Lys Arg Lys Cys Phe Ile Phe Asp Arg Pro Gly
                230                 235                 240

Asp Arg Lys Gln Leu Ser Lys Leu Glu Trp Ile Gln Glu Asp Gln
                245                 250                 255

Leu Asn Lys Glu Phe Val Glu Gln Val Ala Glu Phe Thr Ser Tyr
                260                 265                 270

Ile Phe Ser Tyr Ser Gly Val Lys Thr Leu Ser Gly Gly Ile Thr
                275                 280                 285

Val Asn Gly Pro Arg Leu Lys Ser Leu Val Gln Thr Tyr Val Ser
                290                 295                 300

Ala Ile Cys Ser Gly Glu Leu Pro Cys Met Glu Asn Ala Val Leu
                305                 310                 315

Thr Leu Ala Gln Ile Glu Asn Ser Ala Ala Val Gln Lys Ala Ile
                320                 325                 330

Thr Tyr Tyr Glu Glu Gln Met Asn Gln Lys Ile His Met Pro Thr
                335                 340                 345

Glu Thr Leu Gln Glu Leu Leu Asp Leu His Arg Thr Cys Glu Arg
                350                 355                 360

Glu Ala Ile Glu Val Phe Met Lys Asn Ser Phe Lys Asp Val Asp
                365                 370                 375

Gln Lys Phe Gln Glu Glu Leu Gly Ala Gln Leu Glu Ala Lys Arg
                380                 385                 390

Asp Ala Phe Val Lys Lys Asn Met Asp Met Ser Ser Ala His Cys
                395                 400                 405

Ser Asp Leu Leu Glu Gly Leu Phe Ala His Leu Glu Glu Glu Val
                410                 415                 420
```

-continued

```
Lys Gln Gly Thr Phe Tyr Lys Pro Gly Gly Tyr Tyr Leu Phe Leu
                425                 430                 435

Gln Arg Lys Gln Glu Leu Glu Lys Lys Tyr Ile Gln Thr Pro Gly
                440                 445                 450

Lys Gly Leu Gln Ala Glu Val Met Leu Arg Lys Tyr Phe Glu Ser
                455                 460                 465

Lys Glu Asp Leu Ala Asp Thr Leu Leu Lys Met Asp Gln Ser Leu
                470                 475                 480

Thr Glu Lys Glu Lys Gln Ile Glu Met Glu Arg Ile Lys Ala Glu
                485                 490                 495

Ala Ala Glu Ala Ala Asn Arg Ala Leu Ala Glu Met Gln Lys Lys
                500                 505                 510

His Glu Met Leu Met Glu Gln Lys Glu Gln Ser Tyr Gln Glu His
                515                 520                 525

Met Lys Gln Leu Thr Glu Lys Met Glu Gln Glu Arg Lys Glu Leu
                530                 535                 540

Met Ala Glu Gln Gln Arg Ile Ile Ser Leu Lys Leu Gln Glu Gln
                545                 550                 555

Glu Arg Leu Leu Lys Gln Gly Phe Gln Asn Glu Ser Leu Gln Leu
                560                 565                 570

Arg Gln Glu Ile Glu Lys Ile Lys Asn Met Pro Pro Pro Arg Ser
                575                 580                 585

Cys Thr Ile Leu
            589
```

(2) INFORMATION FOR SEQ ID NO: 15:

(i) SEQUENCE CHARACTERISTICS:
(A) LENGTH: 591 amino acids
(B) TYPE: Amino Acid
(D) TOPOLOGY: Linear (xi) SEQUENCE DESCRIPTION: SEQ ID NO: 15:

```
Met Asp Met Ala Ser Glu Ile His Met Leu Gln Pro Met Cys Leu
  1               5                  10                  15

Ile Glu Asn Thr Glu Ala His Leu Val Ile Asn Gln Glu Ala Leu
                 20                  25                  30

Arg Ile Leu Ser Ala Ile Asn Gln Pro Val Val Val Val Ala Ile
                 35                  40                  45

Val Gly Leu Tyr Arg Thr Gly Lys Ser Tyr Leu Met Asn Lys Leu
                 50                  55                  60

Ala Gly Lys Arg Thr Gly Phe Ser Leu Gly Ser Thr Val Gln Ser
                 65                  70                  75

His Thr Lys Gly Ile Trp Met Trp Cys Val Pro His Pro Lys Lys
                 80                  85                  90

Ala Gly Gln Thr Leu Val Leu Leu Asp Thr Glu Gly Leu Glu Asp
                 95                 100                 105

Val Glu Lys Gly Asp Asn Gln Asn Asp Cys Trp Ile Phe Ala Leu
                110                 115                 120

Ala Val Leu Leu Ser Ser Thr Phe Val Tyr Asn Ser Met Gly Thr
                125                 130                 135

Ile Asn Gln Gln Ala Met Asp Gln Leu His Tyr Val Thr Glu Leu
                140                 145                 150

Thr Asp Leu Ile Lys Ser Lys Ser Ser Pro Asp Gln Ser Gly Ile
                155                 160                 165
```

-continued

```
Asp Asp Ser Ala Asn Phe Val Gly Phe Phe Pro Thr Phe Val Trp
                170                 175                 180

Ala Leu Arg Asp Phe Ser Leu Glu Leu Glu Val Asn Gly Lys Leu
                185                 190                 195

Val Thr Pro Asp Glu Tyr Leu Glu His Ser Leu Thr Leu Lys Lys
                200                 205                 210

Gly Ala Asp Lys Lys Thr Lys Ser Phe Asn Glu Pro Arg Leu Cys
                215                 220                 225

Ile Arg Lys Phe Phe Pro Lys Arg Lys Cys Phe Ile Phe Asp Arg
                230                 235                 240

Pro Ala Leu Arg Lys Gln Leu Cys Lys Leu Glu Thr Leu Gly Glu
                245                 250                 255

Glu Glu Leu Cys Ser Glu Phe Val Glu Gln Val Ala Glu Phe Thr
                260                 265                 270

Ser Tyr Ile Phe Ser Tyr Ser Ala Val Lys Thr Leu Ser Gly Gly
                275                 280                 285

Ile Ile Val Asn Gly Pro Arg Leu Lys Ser Leu Val Gln Thr Tyr
                290                 295                 300

Val Gly Ala Ile Ser Ser Gly Ser Leu Pro Cys Met Glu Ser Ala
                305                 310                 315

Val Leu Thr Leu Ala Gln Ile Glu Asn Ser Ala Ala Val Gln Lys
                320                 325                 330

Ala Ile Thr His Tyr Glu Glu Gln Met Asn Gln Lys Ile Gln Met
                335                 340                 345

Pro Thr Glu Thr Leu Gln Glu Leu Leu Asp Leu His Arg Leu Ile
                350                 355                 360

Glu Arg Glu Ala Ile Glu Ile Phe Leu Lys Asn Ser Phe Lys Asp
                365                 370                 375

Val Asp Gln Lys Phe Gln Thr Glu Leu Gly Asn Leu Leu Ile Ser
                380                 385                 390

Lys Arg Asp Ala Phe Ile Lys Lys Asn Ser Asp Val Ser Ser Ala
                395                 400                 405

His Cys Ser Asp Leu Ile Glu Asp Ile Phe Gly Pro Leu Glu Glu
                410                 415                 420

Glu Val Lys Gln Gly Thr Phe Ser Lys Pro Gly Gly Tyr Phe Leu
                425                 430                 435

Phe Leu Gln Met Arg Gln Glu Leu Glu Lys Lys Tyr Asn Gln Ala
                440                 445                 450

Pro Gly Lys Gly Leu Glu Ala Glu Ala Val Leu Lys Lys Tyr Phe
                455                 460                 465

Glu Ser Lys Glu Asp Ile Val Glu Thr Leu Leu Lys Thr Asp Gln
                470                 475                 480

Ser Leu Thr Glu Ala Ala Lys Glu Ile Glu Val Glu Arg Ile Lys
                485                 490                 495

Ala Glu Thr Ala Glu Ala Ala Asn Arg Glu Leu Ala Glu Lys Gln
                500                 505                 510

Glu Lys Phe Glu Leu Met Met Gln Gln Lys Glu Glu Ser Tyr Gln
                515                 520                 525

Glu His Val Arg Gln Leu Thr Glu Lys Met Lys Glu Glu Gln Lys
                530                 535                 540

Lys Leu Ile Glu Glu Gln Asp Asn Ile Ile Ala Leu Lys Leu Arg
                545                 550                 555

Glu Gln Glu Lys Phe Leu Arg Glu Gly Tyr Glu Asn Glu Ser Lys
```

-continued

```
                560                 565                 570

Lys Leu Leu Arg Glu Ile Glu Asn Met Lys Arg Arg Gln Ser Pro
                575                 580                 585

Gly Lys Cys Thr Ile Leu
                590 591
```

(2) INFORMATION FOR SEQ ID NO: 16:

(i) SEQUENCE CHARACTERISTICS:
(A) LENGTH: 103 amino acids
(B) TYPE: Amino Acid
(D) TOPOLOGY: Linear (xi) SEQUENCE DESCRIPTION: SEQ ID NO: 16:

```
Asn Phe His Gly Ile Trp Ser Thr Thr Met Asp Pro Ile Xaa Leu
  1               5                  10                  15

Val Lys Asn Gln Asn Asn His Leu Thr Val Asn Pro Lys Ala Leu
                 20                  25                  30

Lys Ile Leu Gly Glu Ile Cys Gln Pro Val Val Val Val Thr Ile
                 35                  40                  45

Ala Gly Leu Tyr Arg Thr Gly Lys Ser Tyr Leu Met Asn Arg Leu
                 50                  55                  60

Ala Gly Gln Asn His Gly Phe Arg Leu Gly Ser Thr Val Arg Ser
                 65                  70                  75

Glu Thr Lys Gly Ile Xaa Met Trp Cys Val Pro His Pro Xaa Lys
                 80                  85                  90

Xaa Asp His Ile Leu Val Leu Leu Gly Thr Pro Arg Gly
                 95                 100         103
```

(2) INFORMATION FOR SEQ ID NO: 17:

(i) SEQUENCE CHARACTERISTICS:
(A) LENGTH: 64 amino acids
(B) TYPE: Amino Acid
(D) TOPOLOGY: Linear (xi) SEQUENCE DESCRIPTION: SEQ ID NO: 17:

```
Met Ala Ser Lys Val His Met Pro Glu Pro Gln Cys Leu Ile Glu
  1               5                  10                  15

Asn Ile Asn Gly Arg Leu Ala Val Asn Pro Lys Ala Leu Lys Leu
                 20                  25                  30

Leu Ser Ala Ile Lys Gln Pro Leu Val Val Val Ala Ile Val Gly
                 35                  40                  45

Leu Tyr Arg Thr Gly Lys Ser Tyr Leu Met Asn Lys Leu Ala Xaa
                 50                  55                  60

Lys Asn Lys Gly
             64
```

(2) INFORMATION FOR SEQ ID NO: 18:

(i) SEQUENCE CHARACTERISTICS:
(A) LENGTH: 573 amino acids
(B) TYPE: Amino Acid
(D) TOPOLOGY: Linear (xi) SEQUENCE DESCRIPTION: SEQ ID NO: 18:

```
Met Asp Thr Pro Val Leu Pro Met Pro Ala Pro Leu Arg Leu Val
  1               5                  10                  15

Thr Asn Lys Asp Gly Val Leu Ala Leu Asn Thr Ala Ala Leu Ala
                 20                  25                  30
```

-continued

```
Val Leu Arg Ser Val Thr Gln Pro Val Val Val Val Ala Ile Ala
                35                  40                  45

Gly Pro Tyr Arg Thr Gly Lys Ser Phe Leu Met Asn Arg Leu Ala
                50                  55                  60

Gln Lys Arg Thr Gly Phe Pro Leu Gly Pro Thr Val Tyr Ala Glu
                65                  70                  75

Thr Lys Gly Ile Trp Met Trp Cys Leu Pro His Pro Arg Gln Pro
                80                  85                  90

Arg Val Thr Leu Val Leu Leu Asp Thr Glu Gly Leu Glu Asp Pro
                95                 100                 105

Asn Lys Asp Asn Asp His Ser Asp Ala Trp Ile Phe Thr Leu Ala
               110                 115                 120

Leu Leu Leu Ser Ser Thr Leu Val Tyr Asn Ser Val Gly Thr Ile
               125                 130                 135

Asp Gln Arg Ala Leu Ser Ser Cys Ala Gly Asn Gly Ala Val Arg
               140                 145                 150

Ala His Pro Arg Gly Glu Lys Asp Asn Asn Pro Ala Ser Asn Phe
               155                 160                 165

Val Ser Ile Phe Pro Gly Phe Val Trp Thr Val Arg Asp Phe Thr
               170                 175                 180

Leu Gln Leu Arg Asp Gly Glu Lys Thr Leu Ser Glu Asp Glu Tyr
               185                 190                 195

Leu Glu Asp Val Leu Arg Leu Arg Pro Gly Ala Gly Arg Arg Gln
               200                 205                 210

Glu Arg Asn Glu Leu Arg Arg Cys Leu Pro Asn Phe Phe Pro Arg
               215                 220                 225

Arg Lys Leu Phe Thr Met Glu Arg Pro Ala Ala Asp Ala Asn Leu
               230                 235                 240

Thr Arg Leu Glu Glu Leu Arg Glu Asp Glu Leu Gln Pro Gly Phe
               245                 250                 255

Arg Lys Gln Val Asp Ala Phe Cys Arg Tyr Ile Trp Glu Glu Ala
               260                 265                 270

Pro Val Lys Val Leu Pro Gly Gly His Gln Val Thr Gly Ser Ala
               275                 280                 285

Leu Ala Tyr Leu Val Glu Lys Tyr Met Ala Ala Ile Ser Ser Gly
               290                 295                 300

Ser Val Pro Cys Val Glu Ser Thr Leu Lys Ala Leu Ala Gln Ala
               305                 310                 315

Glu Asn Thr Ala Ala Val Gln Val Ala Val Ala Glu Tyr Gln Arg
               320                 325                 330

Gly Met Glu Gln Gly Leu Val Leu Pro Thr Ala Ser Tyr Asp Ala
               335                 340                 345

Leu Leu Ala Val His Arg Asp Cys Glu Gln Arg Ala Leu Ala Leu
               350                 355                 360

Phe Leu Ser Arg Ala Phe Ala Asp His Lys His Gln Tyr His Asp
               365                 370                 375

Glu Leu Val His Lys Leu Glu Gly Gln Arg Gly Val Leu Pro Ala
               380                 385                 390

Gln Gln Gly Gly Val Gly Ala Ala Val Pro His Gly Ala Ala Gly
               395                 400                 405

Ala Val Glu Gly Arg Gly Arg Arg Leu Gln Arg Gly Asp Tyr Val
               410                 415                 420
```

-continued

```
Ala Arg Gly Gly Ala Gln Leu Phe Lys Glu Asp Val Asn Arg Val
                425                 430                 435

Leu Glu Glu Tyr Lys Gln Arg Pro Asp Lys Gly Val Arg Ala Glu
                440                 445                 450

Ala Val Leu Lys Glu Phe Leu Arg Glu His Glu Gly Leu Ala Gln
                455                 460                 465

Val Leu Lys Ala Thr Glu Val Gln Leu Glu Leu Ala Glu Arg Gln
                470                 475                 480

Gln Glu Ala Ala Ala Ala Glu Ala Glu Ala Ala Arg Lys Ala Thr
                485                 490                 495

Glu Ala Trp Arg Glu Asp Gln Lys Arg Ser Met Glu Glu His Lys
                500                 505                 510

Arg Gln Leu Glu Gln Trp Met Lys Lys Glu Lys His Thr Trp Glu
                515                 520                 525

Glu Glu Leu Asn Arg Met Leu Glu His His Arg Lys Glu Tyr Lys
                530                 535                 540

Ala Leu Leu Gln Glu Gly Phe Arg Arg Glu Ala Ala Ala Lys Glu
                545                 550                 555

Lys Gln Ile Arg Glu Leu Gln Glu Glu Met Arg Ser Cys Asn Cys
                560                 565                 570

Thr Val Leu
        573
```

(2) INFORMATION FOR SEQ ID NO: 19:

(i) SEQUENCE CHARACTERISTICS:
(A) LENGTH: 14 base pairs
(B) TYPE: Nucleic Acid
(C) STRANDEDNESS: Single
(D) TOPOLOGY: Linear (xi) SEQUENCE DESCRIPTION: SEQ ID NO: 19:

TTTTGTACAA GCTT 14

(2) INFORMATION FOR SEQ ID NO: 20:

(i) SEQUENCE CHARACTERISTICS:
(A) LENGTH: 44 base pairs
(B) TYPE: Nucleic Acid
(C) STRANDEDNESS: Single
(D) TOPOLOGY: Linear (xi) SEQUENCE DESCRIPTION: SEQ ID NO: 20:

CTAATACGAC TCACTATAGG GCTCGAGCGG CCGCCCGGGC AGGT 44

(2) INFORMATION FOR SEQ ID NO: 21:

(i) SEQUENCE CHARACTERISTICS:
(A) LENGTH: 43 amino acids
(B) TYPE: Amino Acid
(D) TOPOLOGY: Linear (xi) SEQUENCE DESCRIPTION: SEQ ID NO: 21:

```
Thr Gly Thr Ala Gly Cys Gly Thr Gly Ala Ala Gly Ala Cys Gly
  1               5                  10                  15

Ala Cys Ala Gly Ala Ala Ala Gly Gly Gly Cys Gly Thr Gly Gly
                 20                  25                  30

Thr Gly Cys Gly Gly Ala Gly Gly Gly Cys Gly Gly Thr
                 35                  40          43
```

(2) INFORMATION FOR SEQ ID NO: 22:

(i) SEQUENCE CHARACTERISTICS:
(A) LENGTH: 10 base pairs
(B) TYPE: Nucleic Acid
(C) STRANDEDNESS: Single
(D) TOPOLOGY: Linear (xi) SEQUENCE DESCRIPTION: SEQ ID NO: 22:

ACCTGCCCGG 10

(2) INFORMATION FOR SEQ ID NO: 23:

(i) SEQUENCE CHARACTERISTICS:
(A) LENGTH: 11 base pairs
(B) TYPE: Nucleic Acid
(C) STRANDEDNESS: Single
(D) TOPOLOGY: Linear (xi) SEQUENCE DESCRIPTION: SEQ ID NO: 23:

ACCGCCCTCC G 11

(2) INFORMATION FOR SEQ ID NO: 24:

(i) SEQUENCE CHARACTERISTICS:
(A) LENGTH: 22 base pairs
(B) TYPE: Nucleic Acid
(C) STRANDEDNESS: Single
(D) TOPOLOGY: Linear (xi) SEQUENCE DESCRIPTION: SEQ ID NO: 24:

CTAATACGAC TCACTATAGG GC 22

(2) INFORMATION FOR SEQ ID NO: 25:

(i) SEQUENCE CHARACTERISTICS:
(A) LENGTH: 21 amino acids
(B) TYPE: Amino Acid
(D) TOPOLOGY: Linear (xi) SEQUENCE DESCRIPTION: SEQ ID NO: 25:

```
Thr Gly Thr Ala Gly Cys Gly Thr Gly Ala Ala Gly Ala Cys Gly
  1               5                  10                  15

Ala Cys Ala Gly Ala Ala
                 20  21
```

(2) INFORMATION FOR SEQ ID NO: 26:

(i) SEQUENCE CHARACTERISTICS:
(A) LENGTH: 22 base pairs
(B) TYPE: Nucleic Acid
(C) STRANDEDNESS: Single
(D) TOPOLOGY: Linear (xi) SEQUENCE DESCRIPTION: SEQ ID NO: 26:

TCGAGGGGCC GCCCGGGCAG GT 22

(2) INFORMATION FOR SEQ ID NO: 27:

(i) SEQUENCE CHARACTERISTICS:
(A) LENGTH: 22 base pairs
(B) TYPE: Nucleic Acid
(C) STRANDEDNESS: Single
(D) TOPOLOGY: Linear (xi) SEQUENCE DESCRIPTION: SEQ ID NO: 27:

AGGGCGTGGT GCGGAGGGCG GT 22

(2) INFORMATION FOR SEQ ID NO: 28:

(i) SEQUENCE CHARACTERISTICS:
(A) LENGTH: 20 base pairs
(B) TYPE: Nucleic Acid
(C) STRANDEDNESS: Single
(D) TOPOLOGY: Linear (xi) SEQUENCE DESCRIPTION: SEQ ID NO: 28:

ACCACAGTCC ATGCCATCAC 20

(2) INFORMATION FOR SEQ ID NO: 29:

(i) SEQUENCE CHARACTERISTICS:
(A) LENGTH: 20 base pairs
(B) TYPE: Nucleic Acid
(C) STRANDEDNESS: Single
(D) TOPOLOGY: Linear (xi) SEQUENCE DESCRIPTION: SEQ ID NO: 29:

TCCACCACCC TGTTGCTGTA 20

(2) INFORMATION FOR SEQ ID NO: 30:

(i) SEQUENCE CHARACTERISTICS:
(A) LENGTH: 163 base pairs
(B) TYPE: Nucleic Acid
(C) STRANDEDNESS: Single
(D) TOPOLOGY: Linear (xi) SEQUENCE DESCRIPTION: SEQ ID NO: 30:

TGTAATACGA CTCACTATAG GGCGAATTGG GCCCGACGTC GCATGCTCCC 50

GGCCGCCATG GCCGCGGGAT TATCACTAGT GCGGCCGCCT GCAGGTCGAC 100

CATATGGGAG AGCTCCCAAC GCGTTGGATG CATAGCTTGA GTATTCTATA 150

GTGTCACCTA AAT 163

(2) INFORMATION FOR SEQ ID NO: 31:

(i) SEQUENCE CHARACTERISTICS:
(A) LENGTH: 163 base pairs
(B) TYPE: Nucleic Acid
(C) STRANDEDNESS: Single
(D) TOPOLOGY: Linear (xi) SEQUENCE DESCRIPTION: SEQ ID NO: 31:

ATTTAGGTGA CACTATAGAA TACTCAAGCT ATGCATCCAA CGCGTTGGGA 50

GCTCTCCCAT ATGGTCGACC TGCAGGCGGC CGCACTAGTG ATTATCCCGC 100

GGCCATGGCG GCCGGGAGCA TGCGACGTCG GGCCCAATTC GCCCTATAGT 150

GAGTCGTATT ACA 163

(2) INFORMATION FOR SEQ ID NO: 32:

(i) SEQUENCE CHARACTERISTICS:
(A) LENGTH: 1776 base pairs
(B) TYPE: Nucleic Acid
(C) STRANDEDNESS: Single
(D) TOPOLOGY: Linear (xi) SEQUENCE DESCRIPTION: SEQ ID NO: 32:

ATGGCTTTAG AGATCCACAT GTCAGACCCC ATGTGCCTCA TCGAGAACTT 50

TAATGAGCAG CTGAAGGTTA ATCAGGAAGC TTTGGAGATC CTGTCTGCCA 100

-continued

```
TTACGCAACC TGTAGTTGTG GTAGCGATTG TGGGCCTCTA TCGCACTGGC        150

AAATCCTACC TGATGAACAA GCTGGCTGGG AAGAACAAGG GCTTCTCTGT        200

TGCATCTACG GTGCAGTCTC ACACCAAGGG AATTTGGATA TGGTGTGTGC        250

CTCATCCCAA CTGGCCAAAT CACACATTAG TTCTGCTTGA CACCGAGGGC        300

CTGGGAGATG TAGAGAAGGC TGACAACAAG AATGATATCC AGATCTTTGC        350

ACTGGCACTC TTACTGAGCA GCACCTTTGT GTACAATACT GTGAACAAAA        400

TTGATCAGGG TGCTATCGAC CTACTGCACA ATGTGACAGA ACTGACAGAT        450

CTGCTCAAGG CAAGAAACTC ACCCGACCTT GACAGGGTTG AAGATCCTGC        500

TGACTCTGCG AGCTTCTTCC CAGACTTAGT GTGGACTCTG AGAGATTTCT        550

GCTTAGGCCT GGAAATAGAT GGGCAACTTG TCACACCAGA TGAATACCTG        600

GAGAATTCCC TAAGGCCAAA GCAAGGTAGT GATCAAAGAG TTCAAAATTT        650

CAATTTGCCC CGTCTGTGTA TACAGAAGTT CTTTCCAAAA AAGAAATGCT        700

TTATCTTTGA CTTACCTGCT CACCAAAAAA AGCTTGCCCA ACTTGAAACA        750

CTGCCTGATG ATGAGCTAGA GCCTGAATTT GTGCAACAAG TGACAGAATT        800

CTGTTCCTAC ATCTTTAGCC ATTCTATGAC CAAGACTCTT CCAGGTGGCA        850

TCATGGTCAA TGGATCTCGT CTAAAGAACC TGGTGCTGAC CTATGTCAAT        900

GCCATCAGCA GTGGGGATCT GCCTTGCATA GAGAATGCAG TCCTGGCCTT        950

GGCTCAGAGA GAGAACTCAG CTGCAGTGCA AAAGGCCATT GCCCACTATG       1000

ACCAGCAAAT GGGCCAGAAA GTGCAGCTGC CCATGGAAAC CCTCCAGGAG       1050

CTGCTGGACC TGCACAGGAC CAGTGAGAGG GAGGCCATTG AAGTCTTCAT       1100

GAAAAACTCT TTCAAGGATG TAGACCAAAG TTTCCAGAAA GAATTGGAGA       1150

CTCTACTAGA TGCAAAACAG AATGACATTT GTAAACGGAA CCTGGAAGCA       1200

TCCTCGGATT ATTGCTCGGC TTTACTTAAG GATATTTTTG GTCCTCTAGA       1250

AGAAGCAGTG AAGCAGGGAA TTTATTCTAA GCCAGGAGGC CATAATCTCT       1300

TCATTCAGAA AACAGAAGAA CTGAAGGCAA AGTACTATCG GGAGCCTCGG       1350

AAAGGAATAC AGGCTGAAGA AGTTCTGCAG AAATATTTAA AGTCCAAGGA       1400

GTCTGTGAGT CATGCAATAT TACAGACTGA CCAGGCTCTC ACAGAGACGG       1450

AAAAAAAGAA GAAAGAGGCA CAAGTGAAAG CAGAAGCTGA AAAGGCTGAA       1500

GCGCAAAGGT TGGCGGCGAT TCAAAGGCAG AACGAGCAAA TGATGCAGGA       1550

GAGGGAGAGA CTCCATCAGG AACAAGTGAG ACAAATGGAG ATAGCCAAAC       1600

AAAATTGGCT GGCAGAGCAA CAGAAAATGC AGGAACAACA GATGCAGGTA       1650

TTCATCAATT GTTTCATCTC TCCCCTGCCT GTAACGATGA GAGTATGTAG       1700

CAGTGGCAAA GAGGGAGAGG CAGCAAGATC TTGTGGCTCT CAGCAGGGAG       1750

TCTGGAGCCA GAAAGTCTGG GTATGA                                 1776
```

(2) INFORMATION FOR SEQ ID NO: 33:

(i) SEQUENCE CHARACTERISTICS:
(A) LENGTH: 7 amino acids
(B) TYPE: Amino Acid
(D) TOPOLOGY: Linear (xi) SEQUENCE DESCRIPTION: SEQ ID NO: 33:

```
Arg Gly Ser His His His His
  1               5       7


(2) INFORMATION FOR SEQ ID NO: 34:

     (i) SEQUENCE CHARACTERISTICS:
          (A) LENGTH: 23 amino acids
          (B) TYPE: Amino Acid
          (D) TOPOLOGY: Linear

    (xi) SEQUENCE DESCRIPTION: SEQ ID NO: 34:

 Gly Thr Gly Gly Cys Cys Cys Ala Thr Gly Cys Thr Cys Thr Gly
   1               5                  10                  15

 Gly Cys Ala Gly Ala Gly Gly Gly
                  20          23


(2) INFORMATION FOR SEQ ID NO: 35:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 35:

 Gly Cys Ala Cys Cys Ala Cys Cys Cys Ala Cys Ala Ala Gly Gly
   1               5                  10                  15

 Ala Ala Gly Cys Cys Ala Thr Cys Cys
                  20              24


(2) INFORMATION FOR SEQ ID NO: 36:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 36:

 Cys Cys Gly Gly Ala Cys Ala Cys Gly Gly Cys Ala Ala Ala Gly
   1               5                  10                  15

 Thr Ala Ala Cys Ala Thr Cys Cys Thr
                  20              24


(2) INFORMATION FOR SEQ ID NO: 37:

     (i) SEQUENCE CHARACTERISTICS:
          (A) LENGTH: 23 amino acids
          (B) TYPE: Amino Acid
          (D) TOPOLOGY: Linear

    (xi) SEQUENCE DESCRIPTION: SEQ ID NO: 37:

 Gly Thr Ala Cys Ala Ala Thr Ala Cys Thr Gly Thr Gly Ala Ala
   1               5                  10                  15

 Cys Ala Ala Ala Ala Thr Thr Gly
                  20          23


(2) INFORMATION FOR SEQ ID NO: 38:

     (i) SEQUENCE CHARACTERISTICS:
          (A) LENGTH: 22 amino acids
          (B) TYPE: Amino Acid
          (D) TOPOLOGY: Linear

    (xi) SEQUENCE DESCRIPTION: SEQ ID NO: 38:

 Gly Gly Gly Thr Gly Cys Thr Ala Thr Cys Gly Ala Cys Cys Thr
   1               5                  10                  15
```

```
Ala Cys Thr Gly Cys Ala Cys
                20      22


(2) INFORMATION FOR SEQ ID NO: 39:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 39:

Gly Ala Gly Thr Cys Ala Gly Cys Ala Gly Gly Ala Thr Cys Thr
  1               5                  10                  15

Thr Cys Ala Ala Cys Cys Cys Thr Gly
                20              24


(2) INFORMATION FOR SEQ ID NO: 40:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 40:

Gly Thr Gly Cys Ala Gly Cys Thr Gly Cys Cys Cys Ala Thr Gly
  1               5                  10                  15

Gly Ala Ala Ala Cys Cys Cys Thr Cys
                20              24


(2) INFORMATION FOR SEQ ID NO: 41:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 41:

Cys Thr Gly Cys Thr Gly Ala Gly Ala Gly Cys Cys Ala Cys Ala
  1               5                  10                  15

Ala Gly Ala Thr Cys Thr Thr Gly Cys
                20              24


(2) INFORMATION FOR SEQ ID NO: 42:

     (i) SEQUENCE CHARACTERISTICS:
          (A) LENGTH: 24 amino acids
          (B) TYPE: Amino Acid
          (D) TOPOLOGY: Linear

    (xi) SEQUENCE DESCRIPTION: SEQ ID NO: 42:

Cys Cys Cys Ala Gly Ala Cys Thr Thr Thr Cys Thr Gly Gly Cys
  1               5                  10                  15

Thr Cys Cys Ala Gly Ala Cys Thr Cys
                20              24


(2) INFORMATION FOR SEQ ID NO: 43:

     (i) SEQUENCE CHARACTERISTICS:
          (A) LENGTH: 12 amino acids
          (B) TYPE: Amino Acid
          (D) TOPOLOGY: Linear
```

-continued

```
    (xi) SEQUENCE DESCRIPTION: SEQ ID NO: 43:

 Met Arg Glu Ser His His His His His His Gly Ser
   1               5                  10      12
```

GUANYLATE-BINDING PROTEIN

This is a continuation application claiming priority to application Ser. No. 09/015,089, filed Jan. 29, 1998, now abandoned, the entire disclosure of which is hereby incorporated by reference.

BACKGROUND OF THE INVENTION

This invention was made with government support under grant R29DK48748 awarded by the National Institutes of Health. The government has certain rights in the invention.

1. Field of the Invention

This invention relates to a member of the guanylate-binding protein family designated as GBP-4 and the cloning and expression of nucleic acid encoding this protein. The invention further relates to methods of production of the isolated molecule and its uses.

2. Description of Related Disclosures

One approach to understanding the molecular basis of cancer is to identify differences in gene expression between cancer cells and normal cells. Strategies based on assumptions that steady-state mRNA levels will differ between normal and malignant cells have been used to clone differentially expressed genes. Zhang et al., *Science*, 276: 1268–1272 (1997). The recent development and successful application of such strategies include the use of representational difference analysis (Braun et al., *Mol Cell Biol* 15: 4623–4630 (1995); Lewis et al., *Mol Cell Biol* 17: 4967–4978 (1997)), serial analysis of gene expression (Velculescu et al., *Science*, 270: 484–487 (1995)), and quantitative hybridization analysis of arrayed cDNA's. Schena et al., *Science*, 270: 467–470 (1995).

Cancer of the stomach is a leading cause of cancer deaths worldwide. Parsonnet, *Gastroenterol Clin North Am*, 22: 89–104 (1993); Peddanna et al., *Anticancer Res*, 15: 2055–64 (1995). The development of intestinal-type gastric cancer is characterized by successive histopathologic changes progressing from normal mucosa to gastritis to metaplasia and eventually to dysplasia. Stemmermann et al., *Hum Pathol*, 25: 968–981 (1994).

Cells treated with interferons respond to this stimulus by producing a set of proteins believed to serve as intracellular mediators of the various effects of these cytokines. Interferon-induced GBP's are members of the G protein superfamily and form a distinct subgroup based on their large size (65–67 kDa), potent induction of interferon-γ, and relaxed nucleotide binding. specificity. Nantais et al., *J Leukoc Biol*, 60: 423–431 (1996). Two other subgroups of GTP binding proteins which are induced by interferon include the Mx proteins, which are involved in the antiviral response (Horisberger et al., *J Virol*, 64:1171–81 (1990)), and the inducibly expressed GTPases (IGTP's) which are endoplasmic reticulum GTPases that may be involved in protein processing or trafficking. Taylor et al., *J. Biol Chem*, 271: 20399–20405 (1996); Taylor et al., *J Biol Chem*, 272: 10639–10645 (1997). Interferon-induced GBP's are GTPases which hydrolyze GTP to GDP and at least one GBP, and can bind to agarose-immobilized guanine nucleotides. Cheng et al., *J.Biol. Chem.*, 258: 7746–7750 (1983). GBPs bind to GMP and GTP with similar affinity. Cheng et al., *Mol Cell Biol*, 11: 4717–4725 (1991); Schwemmle et al., *J Biol Chem*, 271: 10304–10308 (1996); Schwemmle and Staeheli, *Curr Opin Cell Biol*, 6: 253–259 (1994). cDNAs for chicken, rat, mouse and human GBPs have been isolated. Asundi et al., *Biochim Biophys Acta*, 1217:257–265 (1994); Cheng et al., (1991), supra; Schwemmle et al., *J Biol Chem*, 271: 10304–10308 (1996); Wynn et al., *J Immunol*, 147: 4384–4392 (1991). Purification of a GBP is described in Cheng et al., *J. Biol. Chem.*, 260: 15834–15839 (1985). It was later found that two distinct interferon-alpha and -gamma-inducible genes code for two human GBPs, designated hGBP1 and hGBP2. Cheng et al., (1991), supra. Subsequently, human GBP3 was identified and partially characterized. Strehlow et al., *Gene*, 144: 295–299 (1994). GBP-3 was shown to have a structure related to GBP-1 and a high degree of sequence homology to both GBP-1 and GBP-2.

Schwemmle and Staeheli, *J. Biol. Chem.*, 269: 11299–11305 (1994) showed that hGBP1, the human 67-kDa guanylate-binding protein, is a GTPase that converts GTP to GMP. Since GTP analogs with a cleavage-resistant bond between the beta- and gamma-phosphates could not be hydrolyzed by hGBP1, and pyrophosphate was no reaction product, hGBP1 seemed to degrade GTP by two consecutive cleavages of single phosphate groups. They further showed that it can be isoprenylated in vitro.

Interferon-induced GBPs have been isolated from other species such as rat (Asundi et al., *Biochim. Biophys. Acta*, 1217: 257–265 (1994); Vestal et al., *Biochem. Biophys. Res. Commun.*, 224: 528–534 (1996)), murine (Vestal et al., *Molecular Bioloay of the Cell*, 7 (SUPPL.): 527A (1996) presented at the Annual Meeting of the 6th International Congress on Cell Biology and the 36th American Society for Cell Biology, San Francisco, Calif., USA, Dec. 7–11, 1996; Vestal et al., *Molecular Biology of the Cell*, 6 (SUPPL.): 288A (1995) presented at the Thirty-fifth Annual Meeting of the American Society for Cell Biology, Washington, D.C., USA, Dec. 9–13, 1995), and chicken. Schwemmle et al., *J. Biol. Chem.*, 271: 10304–10308 (1996). Sequence analysis revealed that human and mouse GBPs contain only the first two elements of the typical GTP-binding consensus motif and that they contain the same sequence motif at their C termini as p21ras. Cheng et al., (1991), supra. The predicted protein sequences of these interferon-induced GBPs lack one of the three sequence motifs typically found in GTP/GDP binding proteins. The GBPs also contain carboxyl terminal residues which are substrates for post-translational modification by protein-prenyl transferases. Nantais et al., *J Leukoc Biol*, 60: 423–431 (1996). Members of the Ras superfamily of GTPases are prenylated and the prenyl modification of these proteins is required for their biological function and cellular localization. Zhang and Casey, *Annu Rev Biochem*, 65: 241–269 (1996).

GTPases serve many different cellular functions. For example, they play key roles in such basic processes as signal transduction, vesicle transport, and translation. Most GTPases contain a tripartite GTP-binding consensus motif. Dever et al., *Proc. Natl. Acad. Sci. USA*, 84: 1814–1818 (1987). These sequences form part of the GTP binding pocket. The typical GTPases can assume two distinct conformations, a GTP-bound (active) and a GDP-bound (inactive) conformation. Hence, they can potentially function as molecular switches. Some GTPases, like p21ras and heterotrimeric G proteins, have a sequence motif at their C-termini that functions as an isoprenylation signal and thus ensures the proper anchoring of these proteins in cell membranes.

SUMMARY OF THE INVENTION

The histopathologic observation by Stemmermann et al., supra, that gastric cancer progresses from normal through to dysplasia prompted investigation into the molecular events which govern this progression from gastritis to malignancy. The study of tumor pathogenesis herein was begun by isolating RNA from normal stomach and from a gastric adenocarcinoma and applying a suppression subtractive hybridization (SSH) technique discussed below. One of the differentially expressed clones identified, and then isolated and characterized, is a new member of the interferon-induced guanylate-binding protein (GBP) gene family, GBP-4.

Accordingly, this invention provides isolated nucleic acid comprising DNA having at least about 600 nucleotides and at least about a 95% sequence identity to (a) a DNA molecule encoding a human GBP-4 polypeptide comprising the sequence of amino acids 1–5591 of FIG. 1 (SEQ ID NO:3), or (b) the complement of the DNA molecule of (a). Preferably, the nucleic acid has at least one GBP-4 biological activity. Also preferred is that the nucleic acid comprise DNA having at least about a 99% sequence identity to (a) a DNA molecule encoding a human GBP-4 polypeptide comprising the sequence of amino acids 1 to 591 of FIG. 1 (SEQ ID NO:3), or (b) the complement of the DNA molecule of (a). More preferably, the nucleic acid comprises DNA encoding a human GBP-4 polypeptide having amino acid residues 1 to 591 of FIG. 1 (SEQ ID NO:3), or the complement of the encoding DNA.

In another aspect, the invention provides isolated nucleic acid comprising DNA having at least about 600 nucleotides and at least about a 95% sequence identity to (a) a DNA molecule encoding the same full-length polypeptide encoded by the human GBP-4 polypeptide cDNA in ATCC Deposit No. 209,456 (pRK5-based plasmid pRK5.hu.GBP4-histag.71), or (b) the complement of the DNA molecule of (a).

In further embodiments of the invention, a vector is provided comprising the nucleic acid, as well as a host cell comprising the vector, especially a host cell that is a human cell, CHO cell, or *E. coli*. In a further aspect, the invention provides a process for producing a GBP-4 polypeptide comprising culturing the host cell under conditions suitable for expression of the GBP-4 polypeptide and recovering the GBP-4 polypeptide from the cell culture.

Also provided is isolated GBP-4 polypeptide encoded by the nucleic acid, preferably human GBP-4.

Further provided is a chimeric molecule comprising a GBP-4 polypeptide fused to a heterologous amino acid sequence. In preferred embodiments, the heterologous amino acid sequence is an epitope tag sequence or an Fc region of an immunoglobulin.

In yet a further embodiment, the invention provides an antibody which specifically binds to a GBP-4 polypeptide, preferably a monoclonal antibody.

In a still further aspect, the invention supplies isolated nucleic acid having at least about 600 nucleotides and produced by hybridizing a test DNA molecule under stringent conditions with (a) a DNA molecule encoding a human GBP-4 polypeptide comprising the sequence of amino acids 1 to 591 of FIG. 1 (SEQ ID NO:3), or (b) the complement of the DNA molecule of (a), and, if the test DNA molecule has at least about a 95% sequence identity to (a) or (b), isolating the test DNA molecule.

Additionally, the invention provides a polypeptide produced by (i) hybridizing a test DNA molecule under stringent conditions with (a) a DNA molecule encoding a human GBP-4 polypeptide comprising the sequence of amino acids 1 to 591 of FIG. 1 (SEQ ID NO:3), or (b) the complement of the DNA molecule of (a), and if the test DNA molecule has at least about a 95% sequence identity to (a) or (b), (ii) culturing a host cell comprising the test DNA molecule under conditions suitable for expression of the polypeptide, and (iii) recovering the polypeptide from the cell culture.

In other embodiments, the invention provides a composition comprising the polypeptide and a carrier therefor, as well as a composition comprising an antagonist to the polypeptide and a carrier therefor. Preferably, the composition further comprises GTP.

In still further embodiments, the invention provides a method of determining the presence in a test sample of a molecule that binds to a guanylate binding protein comprising contacting the test sample with the polypeptide and determining if binding has occurred. In a preferred embodiment, the molecule that binds to the protein is a guanine nucleotide.

In a still further embodiment, the invention supplies a method of determining the presence in a test sample of a guanylate-binding protein-4 comprising contacting the test sample with an immobilized guanine nucleotide and determining if binding has occurred.

Additionally, the invention provides a method for purifying molecules that bind to a guanylate-binding protein comprising contacting a sample containing the molecules to be purified with the polypeptide immobilized on a support under conditions whereby the molecules to be purified are selectively adsorbed onto the immobilized protein, washing the immobilized support to remove non-adsorbed material, and separating the molecules to be purified from the immobilized protein to which they are adsorbed. Preferably, the molecules to be purified are guanine nucleotides.

Also provided is a method of amplifying a nucleic acid test sample comprising priming a nucleic acid polymerase chain reaction with the nucleic acid disclosed above.

Further provided is a method of determining the presence of nucleic acid encoding guanylate-binding protein-4 in a test sample comprising contacting the nucleic acid disclosed above with the test sample and determining whether hybridization has occurred.

The cDNA clone encoding GBP-4 was isolated from a gastric adenocarcinoma by SSH, a technique described below. The predicted amino acid sequence of GBP-4 is homologous with that of a family of mammalian and chicken interferon-inducible GTP binding proteins. GBP-4 shares 60% overall sequence homology with the proteins encoded by cDNA's for human GBP-1 and GBP-2. Cheng et al., (1991), supra. The molecule shares many characteristics with other family members such as chromosomal localization and interferon inducibility. The GBP-4 gene was localized to human chromosome 1p31–1p32, closely linked to the interferon-induced GBP genes, GBP-1 and GBP-2.

Immunoelectron microscopy indicated that GBP-4 was associated with the membranes of endolysosomes. GBP-4 was expressed in many normal tissues examined, with highest levels in peripheral blood leukocytes, lymph node, and the spleen. Like GBP-1 and GBP-2, GBP-4 expression was induced in human cell lines by IFN-γ. Unlike GBP-1 and GBP-2, however, which were both expressed in normal stomach and in stomach tumor tissue, GBP-4 expression was found only in the gastric adenocarcinoma. In situ hybridization performed on gastric tumor tissue demonstrated that GBP-4 mRNA was associated with malignant epithelial cells. The differential expression of GBP-4 and its biological characteristics suggests a role for guanylate binding proteins in tumorigenesis, as well as in inflammatory and immune responses.

BRIEF DESCRIPTION OF THE DRAWINGS

FIG. 1 depicts the nucleotide sequence (top sequence is SEQ ID NO: 1; complementary sequence is SEQ ID NO: 2) and deduced amino acid sequence (SEQ ID NO: 3) of human GBP-4. In this sequence the underlined amino acids are the potential tripartite GTP binding consensus motifs. Potential protein kinase C phosphorylation sites are at positions 49–51, 179–181, 203–205, 358–360, 370–372, 483–485, 562–564, 568–570, and 586–588. Potential casein kinase II phosphorylation sites are at positions 179–182, 195–198, 250–253, 303–306, 347–350, 358–361, 370–373, 384–387, 481–484, and 568–571. Potential N-myristoylation sites are at positions 45–50, 283–288, and 579–584. A potential ATP/GTP-binding site motif A (P-loop) is at positions 45–52.

FIG. 2 is an alignment of the encoded amino acid sequence of human GBP-4 (SEQ ID NO:3) with the sequences of human GBP-1 (SEQ ID NO:4), human GBP-2 (SEQ ID NO:5), and the available published sequence for human GBP-3 (SEQ ID NO:6). The shaded residues correspond to the highly conserved GTP-binding consensus motifs I (GXXXXGKS/T)) (SEQ ID NOS:7 and 8), II (DXXG) (SEQ ID NO:9), and III (N/T)KXD) (SEQ ID NOS:10 and 11). The stars indicate the potential CXXX (SEQ ID NO:12) motifs. The dots indicate the seven di-leucine pairs that could act as potential trans-Golgi network sorting signals.

FIGS. 3A and 3B show an alignment of the amino acid sequences of human GBP-4 (SEQ ID NO:3), mouse purine nucleotide binding protein (SEQ ID NO:13), murine GBP-1 (SEQ ID NO:14), rat GBP (SEQ ID NO:15), a partial sequence of pig GBP-1 (SEQ ID NO:16), the N-terminal sequence of pig GBP-1 (SEQ ID NO:17), and chicken GBP (SEQ ID NO:18).

FIG. 4 shows the percent amino acid identity of the mature form of the GBP family members; (h) human, (r) rat (m) mouse, (c) chicken, and PNBP (purine nucleotide binding protein).

DESCRIPTION OF THE PREFERRED EMBODIMENTS

1. Definitions

Figure 5:
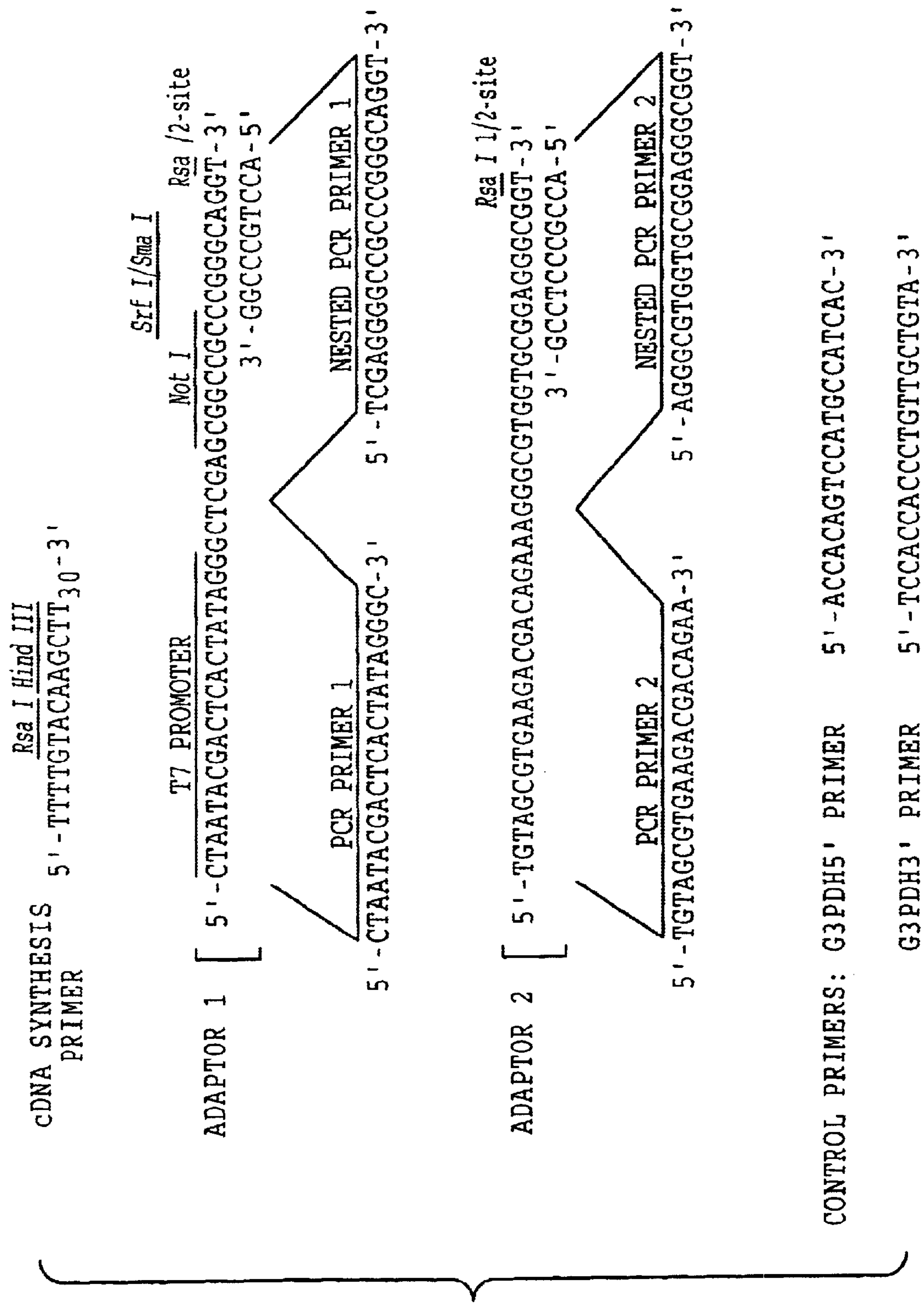
FIG. 5 shows the sequences of the PCR-Select® cDNA synthesis primer (SEQ ID NO:19), adaptors 1 and 2 (SEQ ID NOS:20 and 21, respectively) and complementary sequences for the adaptors (SEQ ID NOS:22 and 23, respectively), PCR primer 1 (SEQ ID NO:24), PCR primer 2 (SEQ ID NO:25), nested PCR primer 1 (SEQ ID NO:26), nested PCR primer 2 (SEQ ID NO:27), control primer G3PDH 5' primer (SEQ ID NO:28), and control primer G3PDH 3' primer (SEQ ID NO:29) used for suppression subtractive hybridization for identifying GBP-4 clones. When the adaptors are ligated to RsaI-digested cDNA, the RsaI site is restored.

In accordance with the present invention, "guanylate-binding protein-4," "GBP4," or "GBP-4" is defined herein to be a native-sequence human GBP-4 protein and variants described herein which are members of the family of interferon-induced GBPs of which GBP-1, GBP-2, and GBP-3 are members.

The terms "GBP-4 polypeptide", "GBP-4 homologue", and grammatical variants thereof, as used herein, encompass native-sequence GBP-4 protein and variants (which are further defined herein). The GBP-4 polypeptide may be isolated from a variety of sources, such as from human tissue types or from another source, or prepared by recombinant or synthetic methods, or by any combination of these and similar techniques.

A "native-sequence GBP-4 polypeptide" comprises a polypeptide having the same amino acid sequence as a GBP-4 polypeptide derived from nature. Such native-sequence GBP-4 polypeptides can be isolated from nature or can be produced by recombinant or synthetic means. The term "native-sequence GBP-4 polypeptide" specifically encompasses naturally occurring truncated forms of a polypeptide disclosed herein, naturally occurring variant forms (e.g., alternatively spliced forms), and naturally occurring allelic variants of a GBP-4 polypeptide. In one embodiment of the invention, the native-sequence GBP-4 polypeptide is a full-length native-sequence human GBP-4 polypeptide comprising amino acids 1 to 591 of FIG. 1 (SEQ ID NO:3), with or without the N-terminal methionine.

The term "GBP-4 variant" means an active GBP-4 polypeptide as defined below having at least about 80%, preferably at least about 85%, more preferably at least about 90%, most preferably at least about 95% amino acid sequence identity with human GBP-4 having the deduced amino acid sequence shown in FIG. 1 (SEQ ID NO:3). Such variants include, for instance, GBP-4 polypeptides wherein one or more amino acid residues are added, or deleted, at the N- or C-terminus of the full-length amino acid sequence of FIG. 1 (SEQ ID NO:3), including variants from other species, but excludes a native-sequence GBP-4 polypeptide.

"Percent (%) amino acid sequence identity" with respect to the GBP-4 sequences identified herein is defined as the percentage of amino acid residues in a candidate sequence that are identical with the amino acid residues in a GBP-4 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Percent (%) nucleic acid sequence identity" with respect to the coding region of the GBP-4 sequences identified herein is defined as the percentage of nucleotides in a candidate sequence that are identical with the nucleotides in the coding region of the GBP-4, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared.

"Stringent conditions" are those that (1) employ low ionic strength and high temperature for washing, for example, 0.015 M sodium chloride/0.0015 M sodium citrate/0.1% sodium dodecyl sulfate at 50° C.; (2) employ during hybridization a denaturing agent, such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS; or (4) employ a buffer of 10% dextran sulfate, 2×SSC (sodium chloride/sodium citrate) and 50% formamide at 55° C., followed by a high-stringency wash consisting of 0.1×SSC containing EDTA at 55° C.

"Moderately stringent conditions" are described in Sambrook et al., *Molecular Cloning: A Laboratory Manual* (New York: Cold Spring Harbor Laboratory Press, 1989), and include the use of a washing solution and hybridization conditions (e.g., temperature, ionic strength, and % SDS) less stringent than described above. An example of moderately stringent conditions is a condition such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc., as necessary to accommodate factors such as probe length and the like.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the GBP-4 natural environment will not be present. Ordinarily, however, isolated polypeptide will be prepared by at least one purification step.

An "isolated" nucleic acid encoding a GBP-4 polypeptide or an "isolated" polypeptide-encoding nucleic acid molecule is a nucleic acid molecule that is identified and separated from at least one contaminant nucleic acid molecule with which it is ordinarily associated in the natural source of the respective nucleic acid. An isolated GBP-4-encoding nucleic acid molecule is other than in the form or setting in which it is found in nature. An isolated GBP-4-encoding nucleic acid molecule therefore is distinguished from the GBP-4-encoding nucleic acid molecule as it exists in natural cells. However, an isolated GBP-4-encoding nucleic acid molecule includes a nucleic acid molecule contained in cells that ordinarily express GBP-4-encoding DNA, where, for example, the nucleic acid molecule is in a chromosomal location different from that of natural cells. The most preferred nucleic acid molecule encoding GBP-4 has the translated nucleotide sequence of FIG. 1 (nucleotides 175–1950 of FIG. 1; SEQ ID NO:32).

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers single anti-GBP-4 polypeptide monoclonal antibodies (including agonist, antagonist, and neutralizing antibodi.es:) and anti-GBP-4 polypeptide antibody compositions with polyepitopic specificity. The term "monoclonal antibody" as used herein refers to an antibody obtained from a population of substantially homogeneous antibodies, i.e., the individual antibodies comprising the population are identical except for possible naturally occurring mutations that may be present in minor amounts.

"Active GBP-4" or "biological activity of GBP-4" or "GBP-4 biological activity", for purposes herein, describes form(s) of a GBP-4 polypeptide which retain the biologic and/or immunologic activities of a native or naturally occurring (native-sequence) GBP-4 polypeptide. Preferred "activities" for a GBP-4 polypeptide include the ability to inhibit the proliferation of cancer cells, as well as to counteract immunological or structural disorders.

An "antagonist" of a GBP-4 polypeptide is a molecule that inhibits an activity of a GBP-4 polypeptide. Preferred antagonists are those which interfere with an undesirable biological activity of GBP-4 such as, for example, in any cases where GBP-4 might act to stimulate cancer cells and the antagonist would inhibit the growth of cancer cells. In some cases, the antagonist may be useful to inhibit binding of GBP-4 to a guanine nucleotide. Such molecules include antibodies and small molecules that have such inhibitory capability, as well as GBP-4 variants or portions thereof that bind to GBP-4. For example, using the human sequence shown in FIG. 1, variants of native GBP-4 are made that act as antagonists, as by using binding studies to determine the binding site(s) of GBP-4 to a guanine nucleotide and eliminating one or more of them by standard techniques (deletion or radical substitution) so that the molecule acts as an antagonist.

Antagonist activity can be determined by several means, including standard assays for induction of cell death such as that described herein, e.g., $^{3}$H-thymidine proliferation assays, or other mitogenic assays, such as an assay measuring the capability of the candidate antagonist of inducing EGF-potentiated anchorage independent growth of target cell lines (Volckaert et al., *Gene*, 15:215–223 (1981)) and/or growth inhibition of neoplastic cell lines. Roberts et al., *Proc. Natl. Acad. Sci. USA*, 82:119–123 (1985). Anchorage-independent growth refers to the ability of GBP-4 polypeptide-treated, or TGF-β-treated and EGF-treated non-neoplastic target cells to form colonies in soft agar, a characteristic ascribed to transformation of the cells. In this assay, the candidate is incubated together with an equimolar amount of a GBP-4 polypeptide otherwise detectable in the EGF-potentiated anchorage-independent target cell growth assay, and the culture observed for failure to induce anchorage-independent growth.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, sheep, pigs, cows, etc. Preferably, the mammal is human.

A "disorder" is any condition that would benefit from treatment with the GBP-4 polypeptides or GBP-4 antagonists herein. This includes chronic and acute disorders, as well as those pathological conditions which predispose the mammal to the disorder in question. Non-limiting examples of disorders to be treated herein include benign and malignant tumors; leukemias and lymphoid malignancies; GTPase activity, guanine nucleotide binding, any carrier or ligand binding activity, or any disorder having a structural role. A principal known effect or function of the GBP-4 herein is binding to at least one guanine nucleotide. For example, the GBP-4 binds to GTP and GMP. A "GBP-4-related disorder" is one caused at least by the action of GBP-4, and may include cancer.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, esophageal cancer, testicular cancer, and various types of head and neck cancer. The preferred cancers for treatment herein are gastric, colon, lung, and melanoma.

The term "cytotoxic agent" as used herein refers to a substance that inhibits or prevents the function of cells and/or causes destruction of cells. The term is intended to include radioactive isotopes (e.g., $^{131}I$, $^{125}I$, $^{90}Y$, and $^{186}Re$), chemotherapeutic agents, and toxins such as enzymatically active toxins of bacterial, fungal, plant, or animal origin, or fragments. thereof.

A "chemotherapeutic agent" is a chemical compound useful in the treatment of cancer. Examples of chemotherapeutic agents include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin, Dactinomycin, Mitomycins, Esperamicins (see U.S. Pat. No. 4,675,187), Melphalan, and other related nitrogen mustards. Also included in this definition are hormonal agents that act to regulate or inhibit hormone action on tumors, such as tamoxifen and onapristone.

A "growth-inhibitory agent" when used herein refers to a compound or composition which inhibits growth of a cell, such as an ErbB2-overexpressing cancer cell, either in vitro or in vivo. Thus, the growth-inhibitory agent is one which significantly reduces the percentage of malignant cells in S phase. Examples of growth-inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, daunorubicin, etoposide, and bleomycin. Those agents that arrest G1 also spill over into phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The 4D5 antibody (and functional equivalents thereof) can also be employed for this purpose if the cancer involves ErbB2-overexpressing cancer cells. See, e.g., WO 92/22653.

"Molecules that bind to a guanylate-binding protein" are those organic molecules and polypeptides that will bind to a GBP such as GBP-1, -2 -3, or -4 under the same conditions under which guanine nucleotides such as GTP and GMP bind to GBP-4. Preferred such molecules are guanine nucleotides.

"Northern analysis" or "Northern blot" is a method used to identify RNA sequences that hybridize to a known probe such as an oligonucleotide, DNA fragment, cDNA or fragment thereof, or RNA fragment. The probe is labeled with a radioisotope such as $^{32}p$, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

The technique of "polymerase chain reaction," or "PCR," as used herein generally refers to a procedure wherein minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant.*

*Biol*., 51: 263 (1987); Erlich, ed., *PCR Technology*, (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

II. Compositions and Methods of the Invention

A. Full-length GBP-4 Polypeptide

The present invention provides newly identified and isolated nucleotide sequences encoding a polypeptide referred to in the present application as a GBP-4 polypeptide. In particular, cDNAs have been identified and isolated encoding novel human GBP-4 polypeptide, as disclosed in further detail in the Examples below.

Using BLAST and FastA sequence alignment computer programs, it was found that the coding sequence of human GBP-4 disclosed herein shows significant homology to DNA sequences disclosed in the GenBank database, including those published by Adams et al., *Nature*, 377: 3–174 (1995).

Further, using BLAST and FastA sequence alignment computer programs, it was found that various portions of the coding sequence of human GBP-4 show significant homology to GBP-2 and GBP-1. Accordingly, it is presently believed that the GBP-4 polypeptides disclosed in the present application are newly identified members of the GBP family and possess activity relating to development of normal and cancerous cells and tissue. More specifically, GBP-4 may be involved in gastric cancers, lung cancer, melanoma, and colon cancer.

B. GBP-4 Variants

In addition to the full-length native-sequence GBP-4 polypeptides described herein, it is contemplated that variants of these sequences can be prepared. GBP-4 variants can be prepared by introducing appropriate nucleotide changes into the GBP-4-encoding DNA, or by synthesis of the desired variant GBP-4 polypeptides. Those skilled in the art will appreciate that amino acid changes may alter post-translational processes of the GBP-4 polypeptide, such as changing the number or position of glycosylation sites or altering the membrane anchoring characteristics.

Variations in the native full-length GBP-4 sequences, or in various domains of the GBP-4 polypeptides described herein, can be made, for example, using any of the techniques and guidelines for conservative and non-conservative mutations set forth, for instance, in U.S. Pat. No. 5,364,934. Variations may be a substitution, deletion, or insertion of one or more codons encoding the GBP-4 polypeptide that results in a change in the amino acid sequence as compared with the native-sequence GBP-4 polypeptide, provided the variant excludes known GBP's such as GBP-1, -2, and -3. Optionally the variation is by substitution of at least one amino acid with any other amino acid in any portion of the GBP-4 polypeptide. Guidance in determining which amino acid residue may be inserted, substituted, or deleted without adversely affecting the desired activity may be found by comparing the sequence of the GBP-4 polypeptide with that of homologous known GBP protein molecules, and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to about 5 amino acids. The variation allowed may be determined by systematically making insertions, deletions, or substitutions of amino acids in the sequence and testing the resulting variants for activity in in vitro assays for gene upregulation or downregulation and in transgenic or knockout animals.

The variations can be made on the DNA using methods known in the art such as oligonucleotide-mediated (site-directed) mutagenesis (Carter et al., *Nucl. Acids Res*., 13:4331 (1986); Zoller et al., *Nucl. Acids Res*., 10:6487 (1987)), alanine scanning, PCR mutagenesis, cassette mutagenesis (Wells et al., *Gene*, 34:315 (1985)4, restriction selection mutagenesis (Wells et al., *Philos. Trans. R. Soc. London SerA*, 317:415 (1986)), or other known techniques.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions. T. E. Creighton, *Proteins: Structure and Molecular Properties* (W. H. Freeman & Co., San Francisco, 1983); Chothia, *J. Mol. Biol*., 150:1 (1976). If alanine substitution does not yield adequate amounts of variant, an isoteric amino acid can be used.

Further deletional variants of the full-length GBP-4 polypeptide include variants from which the initiating methionine has been deleted.

Exemplary variants based on the amino acid sequence in FIG. 1 (SEQ ID NO:3) include those variants with the most homology among GBP-4, GBP-3, GBP-2, and GBP-1, as well as among murine GBP-1 and rat GBP. Referring to FIGS. 2 and 3A–3B, preferred variants are those which have conservative substitutions in the regions of amino acids 1–2, 4–7, 9–20, 22–159, 163–201, 203–213, 217–376, 378–382, 384–397, 399–469, 472–478, 480–485, 492–495, 511–520, 523–528, and/or 544–545. Referring to FIGS. 2 and 3A–3B, additional preferred variants are those which have exemplary substitutions and/or deletions within the regions of amino acids 3, 8–9, 21, 160–162, 202, 214–216, 377, 383, 398, 470–471, 479, 486–491, 496–510, 521–522, 529–543, and/or 546–590.

Also preferred variants are those with deletions of amino acids 8 and 9, and/or with deletions of amino acids 17–20, and/or with substitutions at amino acids 130–133 as follows: T130S,V131M,N132G,K133T; T130S,V131M,N132N, T133K; T130S,V131I,N132G,K133T; and/or T130S,V131I, N132N,K133K, or other permutations thereof, and/or with deletions of amino acids 139–141 or substitutions at these residues as follows: I139M,L141Q; I139L,L141Q; I139M, D140E,L141Q; and/or I139L,D140E,L141Q, and/or with deletions of amino acids 153–157 or substitutions at these residues as follows: L153I,N157S; L153I,K154R,R156N, N157S; L153I,R154R,A155S,R156K,N157S; and/or L153I, K154R,R156K,N157S, or other permutations thereof, and/or with deletions of amino acids 160–163, and/or with deletions of amino acids 205–208, or substitutions at these residues as follows: R205K,P206L,K207R,Q208K; and/or R205K,P206L,Q208K, or other permutations thereof, and/or with deletions of amino acids 209–215, or substitutions/deletions at these residues as follows: S209T,D210S,R212K, V213Δ,Q214Δ,N215Δ; and/or S209T,Q211K,R212K, V213Δ,Q214Δ,N215Δ, or other permutations thereof, and/or with deletions of amino acids 292–293, or substitutions at these residues as follows: K292E,N293S; and/or N293S, and/or with substitutions/deletions at amino acids 383–385 as follows: E383A,T384A,L385Q, and/or with substitutions at amino acids 387–392 as follows: D387E,Q390R,N391D; D387E,A388K,Q391R,N391D; D387E,K389R,Q390R, N391D; D387E,A388E,K389R,Q390K,N391E; and/or D387I,A388S,Q390R,N391D, or other permutations thereof, and/or with deletions of amino acids 431–432, or substitutions at these residues as follows: H431Y,N432R; H431Y,N432S; and/or H431Y,N432F, and/or with substitutions at amino acids 438–439 as follows: T438L,E439Q; T438R,E439Q; T438K,E439Q; and/or T438R,E439K, or other permutations thereof, and/or with deletions of amino acids 447–448 or substitutions at these residues as follows: R447Q,E448V; R447E; R447Q,E448R; R447Q,E448A; and/or R447Q,E448T, or other permutations thereof, and/or with deletions of amino acids 470–471 or substitutions at these residues as follows: S470T,H471D; S470A,H471D; S470E,H471D; and/or S470V,H471E, or other permutations thereof, and/or with deletions of amino acids 486–491 or substitutions/deletions at these residues as follows: K486E, K487I,K488E,E489V,A490E,Q491R; K486A,K487I, K488E,E489V,A490E,Q491R; K486A,K487I,K488E, E489V,A490E,Q491R; K486A,K487I,K488E,E489M, A490E,Q491R; K486A,K487I,K488A,E489A,A490E, Q491R; K486Q,K487I,K488E,E489V,A490E,Q491R; K486Q,K487I,K488E,E489M,A490E,Q491R; K486E, K487I,K488E,E489M,A490E,Q491R; K486E,K487I, K488A,E489A,A490E,Q491R; K486A,K487I,K488E, E489M,A490E,Q491R; K486A,K487I,K488A,E489A, A490E,Q491R; and/or K486Q,K487I,K488A,E489A, A490E,Q491R, or other permutations thereof, and/or with deletions of amino acids 496–498 or substitutions at these residues as follows: A496S,E497A,K498Q; A496S,E497A, K498E; E497A,K498E; A496T,E497A,K498E; A496V, E497A,K498E, or other permutations thereof, and/or with substitutions of amino acids 502–507 as follows: Q502K, R503M,A505E,A506E,I507M; Q502K,R503M,A505Q, A506E,I507M; Q502K,R503M,A505E,A506E; and/or Q502K,R503M,L504V,A505E,A506E,I507M, or other permutations thereof, and/or with deletions of amino acids 509–511 or substitutions at these residues as follows: Q51OK; F509K,Q510K; R509I,Q510K,N511Y; F509K, Q510K,N511H; and/or F509K,Q510E,N511Q, or other permutations thereof, and/or with deletions of amino acids 516–518 or substitutions at these residues as follows: Q516E,E517Q,R518K; Q516E,R518K; E517Q,R518K; and/or Q516E,E517A,R518Q, or other permutations thereof, and/or with deletions of amino acids 520–522 or substitutions at these residues as follows: R520K,L521S, H522Y; L521S,H522Y; R520E,L521S,H522Y; R520Q, L521S,H522Y; and/or L521S,H522F, or other permutations thereof, and/or with substitutions/deletions at amino acids 525–543 as follows: Q525H,V526V(L),R527K,M529L, E530T,I531E,A532K,K533M,Q534E, N535R(N),W536D, L537R,A538V,E539Q,Q540L,Q541L(M),K542A(K), M543E;

and/or Q525H,V526M,R527R,Q528K,M529L,E530T, I531E,A532K,K533M,Q534E(K), N53SE(K),W536Δ, L537Δ,A538Δ,Q540R(K),Q541K,K542M,M543L; or other permutations thereof, and/or with substitutions/deletions at amino acids 546–566 as follows: Q546E,M548E,Q549K, V550M,F551L,I552E,N553H,C554K,F555L,I556K,S557E, P558Q,L559E,P560K,V561L,T562L,M563K,R564E, V565G,C566F; Q546E,M548E,Q549R,V550I,F551I,I552S, N553L,C554K,F555R,I556R,S557V, P558Q,L559E, P560R,V561F,T562L,M563R,R564Q,V565G,C566Y; Q546R,Q547T,M548L,Q549A,V550L,F551K,I552L, N553Q,C554E,F555Q, I556E,S557R(Q),P558L,L559L, P560K,V561E,T562G,M563F,R564Q,V565K,C5 66E; Q546K,M548T,Q549L,V550M,F551L,I552E,N553H, C554K,F555L,I556K,S557E, P558Q,L559E,P560K, V561L,T562L,M563K,R564E,V565G,C566F; Q546E, M548E,Q549K,V550M,F551L,I552E,N553H,C554K, F555L,I556K,S557E, P558Q,L559E,P560K,V561L,T562L, M563K,R564E,V565N,C566F; and/or Q546E,M548E, Q549K,V550M,F551L,I552E,N553H,C554K,F555L, I556K,S557E, P558Q,L559E,P560K,V561L,T562L, M563K,R564A,V565A,C566F, or other permutations thereof, and/or with deletions of amino acids 567–571, and/or with substitutions of amino acids 572–577 as follows: E572L,A573L,A574R,R575E,S576I,C577E; E572K, A573R,A574Q,R575E,S576I,C577E; E572D,A573I, A574W,R575D,S576I,C577Q; E572D,A573I,A574Q, R575D,S576I,C577Q; E572E,A573I,A574Q,R575D, S576L,C577Q; E572E,A573I,A574W,R575E,S576I, C577E; E572E,A573I,A574Q,R575E,S576I,C577E; E572D,A573I,A574W,R575E,S576I,C577E; E572D, A573I,A574Q,R575E,S576I,C577E; E572E,A573I, A574W,R575D,S576I,C577Q; E572E,A573I,A574Q, R575D,S576I,C577Q; E572L,A573L,A574Q,R575E, S576I,C577E; E572K,A573R,A574R,R575E,S576I,C577E; and/or E572E,A573I,A574Q,R575D,S576I,C577Q, or other permutations thereof, and/or with deletions of amino acids 578–586, and/or with deletions of amino acids 587–590 or substitutions/deletions at these residues as follows: K587, CV588T,W589I,V590S; K587C,V588N,W589I,V590L; K587C,V588T,W589I,V590L; K587C,V588N,W589I, V590S; V588C,W589T,V590V; V588C,W589T,V590V, Δ591L; V588C,W589T,V590I; V588C,W589T,V590I, Δ591L; V588I,W589M,V590I; V588I,W589M,V590I, Δ591L; K587R,V588I,W589M,V590I; and/or K587R, V588I,W589M,V590I,Δ591L, a deletion from C554 to the end of the molecule, C554E,F555Q,I556E as the carboxy terminus, a deletion from 446 to the end of the molecule, a deletion from 496 to the end of the molecule, a deletion from 548 to the end of the molecule, and/or Q547L with a deletion of the rest of the molecule, or other permutations thereof.

C. Modifications of the GBP-4 Protein

Covalent modifications of the GBP-4 polypeptides are included within the scope of this invention. One type of covalent modification includes reacting targeted amino acid residues of a GBP-4 polypeptide with an organic derivatizing agent that is capable of reacting with selected side chains or the N- or C-terminal residues. Derivatization with bifunctional agents is useful, for instance, for crosslinking GBP-4 to a water-insoluble support matrix or surface for use in the method for purifying anti-GBP-4 antibodies, and vice-versa. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidyl-propionate), bifunctional maleimides such as bis-N-maleimido-1,8-octane, and agents such as methyl-3-((p-azidophenyl)dithio)pro-pioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (Creighton, supra, pp. 79–86), acetylation of the N-terminal amine, and amidation of any C-terminal carboxyl group.

Another type of covalent modification of the GBP-4 polypeptide included within the scope of this invention comprises altering the native glycosylation pattern of the polypeptide. "Altering the native glycosylation pattern" is intended for purposes herein to mean deleting one or more carbohydrate moieties found in the native sequence (either by deleting the underlying glycosylation site or by removing the glycosylation moieties by chemical and/or enzymatic means) and/or adding one or more glycosylation sites that are not present in the native sequence. In addition, the phrase includes qualitative changes in the glycosylation of the native proteins, involving a change in the nature and proportion of the various sugar residues present. The native human GBP-4 has potential glycosylation sites at positions 90–93, 144–147, and 287–290.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the GBP-4 is conveniently accomplished by altering the amino acid sequence such that it contains one or more of the above-described tripeptide sequences (for N-linked glycosylation sites). The alteration may also be made by the addition of, or substitution by, one or more serine or threonine residues to the native GBP-4 sequence (for O-linked glycosylation sites). For ease, the GBP-4 amino acid sequence is preferably altered through changes at the DNA level, particularly by mutating the DNA encoding the GBP-4 at preselected bases such that codons are generated that will translate into the desired amino acids. The DNA mutation(s) may be made using methods described above.

Another means of increasing the number of carbohydrate moieties on the GBP-4 is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl. groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep, 11, 1987, and in Aplin and Wriston, *CRC Crit. Rev. Biochem.*, pp. 259–306 (1981).

Removal of carbohydrate moieties-present on the GBP-4 may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., *Arch. Biochem. Biophys.*, 259: 52 (1987) and by Edge et al., *Anal. Biochem.*, 118: 131 (1981). Enzymatic cleavage of carbohydrate moieties from polypeptides can be achieved by the use of a variety of endo- and exo-glycosidases as described by Thotakura et al., *Meth. Enzymol.*, 1: 350 (1987).

Glycosylation at potential glycosylation sites may be prevented by the use of the compound tunicamycin as described by Duskin et al., *J. Biol. Chem.*, 257: 3105 (1982). Tunicamycin blocks the formation of protein-N-glycoside linkages.

Another type of covalent modification of GBP-4 comprises linking the GBP-4 to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

It will be appreciated that some screening of the recovered GBP-4 variant will be needed to select the preferred variant for binding to a guanine nucleotide and having the immunological and/or biological activity defined above. One can screen for stability in recombinant cell culture or in plasma (e.g., against proteolytic cleavage), high affinity to a guanine nucleotide, oxidative stability, ability to be secreted in elevated yields, and the like. For example, a change in the immunological character of the GBP-4 polypeptide, such as affinity for a given antibody, is measured by a competitive-type immunoassay. Other potential modifications of polypeptide properties such as redox or thermal stability, hydrophobicity, or susceptibility to proteolytic degradation are assayed by methods well known in the art.

The GBP-4 polypeptide of the present invention may also be modified in a way to form a chimeric molecule comprising GBP-4, or a fragment thereof, fused to a heterologous polypeptide or amino acid sequence. In one embodiment, such a chimeric molecule comprises a fusion of the GBP-4 polypeptide with a tag polypeptide which provides an epitope to which an anti-tag antibody can selectively bind. The epitope tag is generally placed at the amino- or carboxyl-terminus of a native or variant GBP-4 molecule. The presence of such epitope-tagged forms can be detected using an antibody against the tag polypeptide. Also, provision of the epitope tag enables the GBP-4 polypeptides to be readily purified by affinity purification using an anti-tag antibody or another type of affinity matrix that binds to the epitope tag. In an alternative embodiment, the chimeric molecule may comprise a fusion of the GBP-4 polypeptides, or fragments thereof, with an immunoglobulin or a particular region of an immunoglobulin. For a bivalent form of the chimeric molecule, such a fusion could be to the Fc region of an Ig, such as an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., *Mol. Cell. Biol.*, 8:2159–2165 (1988)); the c-myc tag and the 8F9, 3C7, 6E10, G4, B7, and 9E10 antibodies thereto (Evan et al., *Molecular and Cellular Biology*, 5:3610–3616 (1985)); and the Herpes Simplex virus glycoprotein D (gD) tag and its antibody. Paborsky et al., *Protein Engineering*, 3(6):547–553 (1990). Other tag polypeptides include the Flag-peptide (Hopp et al., *BioTechnology*, 6:1204–1210 (1988)); the KT3 epitope peptide (Martin et al., *Science*, 255:192–194 (1992)); an α-tubulin epitope peptide (Skinner et al., *J. Biol. Chem.*, 266:15163–15166 (1991)); and the T7 gene 10 protein peptide tag. Lutz-Freyermuth et al., *Proc. Natl. Acad. Sci. USA*, 87:6393–6397 (1990).

D. Preparation of GBP-4

The description below relates primarily to production of GBP-4 polypeptides by culturing cells transformed or transfected with a vector containing at least human GBP-4 DNA (SEQ ID NO:1). It is, of course, contemplated that alternative methods, which are well known in the art, may be employed to prepare GBP-4 polypeptides. For instance, the GBP-4 sequence, or portions thereof, may be produced by direct peptide synthesis using solid-phase techniques. See, e.g., Stewart et al., *Solid-Phase Peptide Synthesis* (W. H. Freeman Co.: San Francisco, Calif., 1969); Merrifield, *J. Am. Chem. Soc*., 85:2149–2154 (1963). In vitro protein synthesis. may be performed using manual techniques or by automation. Automated synthesis may be accomplished, for instance, using an Applied Biosystems peptide synthesizer (Foster City, Calif.) in accordance with manufacturer's instructions. Various portions of GBP-4 polypeptides may be chemically synthesized separately and combined using chemical or enzymatic methods to produce a full-length GBP-4 polypeptide.

1. Isolation of DNA Encoding GBP-4

DNA encoding a GBP-4 polypeptide may be obtained from a cDNA library prepared from tissue believed to possess the GBP-4 mRNA and to express it at a detectable level. Accordingly, human GBP-4-encoding DNA can be conveniently obtained from a cDNA library prepared from human tissue or cell lines., such as cell lines made from tumors. More preferably, cell line cDNA libraries from human stomach tumors are screened with oligonucleotide probes. The GBP-4-encoding gene may also be obtained from a genomic library or by oligonucleotide synthesis.

A still alternative method of cloning GBP-4 is suppressive subtractive hybridization, which is a method for generating differentially regulated or tissue-specific cDNA probes and libraries. This is described, for example, in Diatchenko et al., *Proc. Natl. Acad. Sci USA*, 93: 6025–6030 (1996). The procedure is based primarily on a technique called suppression PCR and combines normalization and subtraction in a single procedure. The normalization step equalizes the abundance of cDNAs within the target population and the subtraction step excludes the common sequences between the target and driver populations.

Libraries can be screened with probes (such as antibodies to a GBP-4 polypeptide or oligonucleotides of at least about 20–80 bases) designed to identify the gene of interest or the protein encoded by it. Screening the cDNA or genomic library with the selected probe may be conducted using standard procedures, such as described in Sambrook et al., supra. An alternative means to isolate the gene encoding GBP-4 is to use PCR methodology. Sambrook et al., supra; Dieffenbach et al., *PCR Primer: A Laboratory Manual* (New York: Cold Spring Harbor Laboratory Press, 1995).

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation, or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequences disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for GBP-4 polypeptide production and cultured in conventional nutrient media modified as appropriate for inducing promoters, selecting transformants, or amplifying the genes encoding the desired sequences. The culture conditions, such as media, temperature, pH, and the like, can be selected by the skilled artisan without undue experimentation. In general, principles, protocols, and practical techniques for maximizing the productivity of cell cultures can be found in *Mammalian Cell Biotechnoloay: a Practical Approach*, M. Butler, ed. (IRL Press, 1991) and Sambrook et al., supra.

Methods of transfection are known to the ordinarily skilled artisan, for example, $CaPO_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact*., 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene or polyornithine, may also be used. For various techniques for transforming mammalian cells, see Keown et al., *Methods in Enzymology*, 1:527–537 (1990) and Mansour et al., *Nature*, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella, as well as Bacilli such as *B. subtilis* and *B. licheniformis* (e.g., *B. licheniformis* 41P disclosed in DD 266,710 published Apr. 12, 1989), Pseudomonas such as *P. aeruginosa*, and Streptomyces. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635). These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for GBP-4-encoding vectors. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature*, 290: 140 (1981); EP 139,383 published May 2, 1985); Kluyveromyces hosts (U.S. Pat. No. 4,943,529; Fleer et al., *Bio/Technology*, 9: 968–975 (1991)) such as, e.g., *K. lactis* (MW98-8C, CBS683, CBS4574; Louvencourt et al., *J. Bacteriol.*, 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8: 135 (1990)), *K . thermotolerans*, and *K. marxianus; yarrowia* (EP 402,226); *Pichia pastoris* (EP 183,070; Sreekrishna et al., *J. Basic Microbiol.*, 28: 265–278 (1988)); Candida; *Trichoderma reesia* (EP 244,234); *Neurospora crassa* (Case et al., *Proc. Natl. Acad. Sci. USA*, 76: 5259–5263 (1979)); Schwanniomyces such as *Schwanniomyces occidentalis* (EP 394,538 published Oct. 31, 1990); and filamentous fungi such as, e.g., Neurospora, Penicillium, Tolypocladium (WO 91/00357 published Jan. 10, 1991), and Aspergillus hosts such as *A. nidulans* (Ballance et al., *Biochem. Biophys. Res. Commun.*, 112: 284–289 (1983); Tilburn et al., *Gene*, 26: 205–221 (1983); Yelton et al., *Proc. Natl. Acad. Sci. USA*, 81: 1470–1474 (1984)) and *A. niger*. Kelly and Hynes, *EMBO J.*, 4: 475–479 (1985). Methylotropic yeasts are suitable herein and include, but are not limited to, yeast capable of growth on methanol selected from the genera consisting of Hansenula, Candida, Kloeckera, Pichia, Saccharomyces, Torulopsis, and Rhodotorula. A list of specific species that are exemplary of this class of yeasts may be found in C. Anthony, *The Biochemistry of Methylotrophs*, 269 (1982).

Suitable host cells for the expression of glycosylated GBP-4 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding the desired GBP-4 polypeptide may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, an origin of replication, one or more marker genes, an enhancer element, a promoter, and a transcription termination sequence. Construction of suitable vectors containing one or more of these components employs standard ligation techniques which are known to the skilled artisan.

The desired GBP-4 polypeptide may be produced recombinantly not only directly, but also as a fusion polypeptide with a heterologous polypeptide, which may be another polypeptide having a specific cleavage site at the N-terminus of the full-length protein or polypeptide.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2$\mu$ plasmid origin is suitable for yeast, and various viral origins (SV40, polyoma, adenovirus, VSV, or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the GBP-4-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7. Stinchcomb et al., *Nature*, 282:39 (1979); Kingsman et al., *Gene*, 7:141 (1979); Tschemper et al., *Gene*, 10:157 (1980). The trp1 gene provides a selection marker for a mutant strain of yeast lacking the ability to grow in tryptophan, for example, ATCC No. 44076 or PEP4-1. Jones, *Genetics*, 85:12 (1977).

Expression and cloning vectors usually contain a promoter operably linked to the GBP-4-encoding nucleic acid sequence to direct mRNA synthesis. Promoters recognized by a variety of potential host cells are well known. Promoters suitable for use with prokaryotic hosts include the β-lactamase and lactose promoter systems (Chang et al., *Nature*, 275:615 (1978); Goeddel et al., *Nature*, 281:544 (1979)), alkaline phosphatase, a tryptophan (trp) promoter system (Goeddel, *Nucleic Acids Res.*, 8:4057 (1980); EP 36,776), and hybrid promoters such as the tac promoter. deBoer et al., *Proc. Natl. Acad. Sci. USA*, 80:21–25 (1983). Promoters for use in bacterial systems also will contain a Shine-Dalgarno (S. D.) sequence operably linked to the DNA encoding the GBP-4 polypeptide.

Examples of suitable promoting sequences for use with yeast hosts include the promoters for 3-phosphoglycerate kinase (Hitzeman et al., *J. Biol. Chem.*, 255:2073 (1980)) or other glycolytic enzymes (Hess et al., *J. Adv. Enzyme Reg.*, 7:149 (1968); Holland, Biochemistry, 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phos-phate dehydrogenase, and enzymes responsible for maltose and galactose utilization. Suitable vectors and promoters for use in yeast expression are further described in EP 73,657.

GBP-4 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus, and Simian Virus 40 (SV40); from heterologous mammalian promoters, e.g., the actin promoter or an immunoglobulin promoter; and from heat-shock promoters, provided such promoters are compatible with the host cell systems.

Transcription of a DNA encoding a GBP-4 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the GBP-4 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the GBP-4.

Still other methods, vectors, and host cells suitable for adaptation to the synthesis of GBP-4 polypeptides in recombinant vertebrate cell culture are described in Gething et al., *Nature*, 293:620–625 (1981); Mantei et al., *Nature*, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201–5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native-sequence GBP-4 polypeptide or against a synthetic peptide based on the DNA sequences provided herein or against exogenous sequence fused to GBP-4-encoding DNA and encoding a specific antibody epitope.

5. Purification of Polypeptide

Forms of GBP-4 may be recovered from culture medium or from host cell lysates. If membrane-bound, it can be released from the membrane using a.suitable detergent solution (e.g., Triton-X 100) or by enzymatic cleavage. Cells employed in expression of GBP-4 polypeptides can be disrupted by various physical or chemical means, such as freeze-thaw cycling, sonication, mechanical disruption, or cell lysing agents.

It may be desired to purify GBP-4 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75; protein A SEPHAROSE™ columns to remove contaminants such as IgG; and metal chelating columns to bind epitope-tagged forms of the GBP-4 polypeptide. Various methods of protein purification may be employed, and such methods are known in the art and described, for example, in Deutscher, *Methods in Enzymology*, 182 (1990) and Scopes, *Protein Purification:Principles and Practice* (Springer-Verlag: New York, 1982). The purification step(s) selected will depend, for example, on the nature of the production process used and the particular GBP-4 polypeptide produced.

E. Uses for GBP-4 and its Nucleic Acid

Nucleotide sequences (or their complement) encoding GBP-4 polypeptides have various applications in the art of molecular biology, including uses as hybridization probes, in chromosome and gene mapping, and in the generation of anti-sense RNA and DNA. GBP-4-encoding nucleic acid will also be useful for the preparation of GBP-4 polypeptides by the recombinant techniques described herein.

The full-length nucleotide sequence for human GBP-4 (SEQ ID NO:1), or portions thereof, may be used as a hybridization probe for a cDNA library to isolate or detect still other genes (for instance, those encoding naturally occurring variants of GBP-4, other GBP family members, or GBP-4 from other species) which have a desired sequence identity to the GBP-4 sequence disclosed in FIG. 1. For example, such procedures as in situ hybridization, Northern and Southern blotting, and PCR analysis may be used to determine whether DNA and/or RNA encoding a different GBP is present in the cell type(s) being evaluated. Optionally, the length of the probes will be about 20 to about 50 bases. For example, the hybridization probes may be derived from genomic sequences including promoters, enhancer elements, and introns of native-sequence GBP-4- encoding DNA. By way of example, a screening method will comprise isolating the coding region of the GBP-4 gene using the known DNA sequence to synthesize a selected probe of about 40 bases. Hybridization probes may be labeled by a variety of labels, including radionucleotides such as $^{32}$p or $^{35}$S, or enzymatic labels such as alkaline phosphatase coupled to the probe via avidin/biotin coupling systems. Labeled probes having a sequence complementary to that of any of the GBP-4 genes of the present invention can be used to screen libraries of human cDNA, genomic DNA, or mRNA to determine to which members of such libraries the probe hybridizes. Hybridization techniques are described in further detail in the Examples below.

The probes may also be employed in PCR techniques to generate a pool of sequences for identification of closely related GBP-4 sequences.

Nucleotide sequences encoding a GBP-4 polypeptide can also be used to construct hybridization probes for mapping the gene which encodes that GBP-4 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acid encoding GBP-4 may be used as a diagnostic to determine the extent and rate of the expression of the GBP-4 in the cells of a patient. To accomplish such an assay, a sample of a patient's cells is treated, via in situ hybridization, or by other suitable means, and analyzed to determine whether the sample contains mRNA molecules capable of hybridizing with the nucleic acid molecule.

Nucleic acids which encode GBP-4 polypeptides or any of their modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding a GBP-4 polypeptide can be used to clone genomic DNA encoding the GBP-4 polypeptide in accordance with established techniques and the genomic sequences used to generate transgenic animals that contain cells which express DNA encoding the GBP-4 polypeptide.

Methods for generating transgenic animals, particularly animals such as mice or rats, have become conventional in the art and are described, for example, in U.S. Pat. Nos. 4,736,866 and 4,870,009 and WO 97/38086. Typically, particular cells would be targeted for GBP-4 transgene incorporation with tissue-specific enhancers, which could result in cellular transformation with or without concommitant immune activation, or responsiveness to growth inhibition, depending on the cell type or organ in which the transgene is expressed. When the KATO III cell line, which may express low to undetectable levels of GBP-4 and is from a gastric carcinoma, is treated with IFN-γ, there is no anti-proliferative response. The other cell lines which expressed GBP-4 showed responsiveness to IFN-γ-induced growth inhibition. Transgenic animals that include a copy of a transgene encoding GBP-4 introduced into the germ line of the animal at an embryonic stage can be used to examine the effect of increased expression of DNA encoding GBP-4. Such animals can be used as tester animals for reagents thought to confer protection from, for example, cancer or immune disorders. In accordance with this facet of the invention, an animal is treated with the reagent and a reduced incidence of the disease, compared to untreated animals bearing the transgene, would indicate a potential therapeutic intervention for the disease.

Alternatively, non-human homologues of GBP-4 polypeptides can be used to construct a GBP-4 polypeptide "knock out" animal which has a defective or altered gene encoding a GBP-4 polypeptide as a result of homologous recombination between the endogenous gene encdding the GBP-4 polypeptide and altered genomic DNA encoding the GBP-4 polypeptide introduced into an embryonic cell of the animal. For example, cDNA encoding the GBP-4 polypeptide can be used to clone genomic DNA encoding the GBP-4 polypeptide in accordance with established techniques. A portion of the genomic DNA encoding the GBP-4 polypeptide can be deleted or replaced with another gene, such as a gene encoding a selectable marker which can be used to monitor integration. Typically, several kilobases of unaltered flanking DNA (both at the 5' and 3' ends) are included in the vector. See e.g., Thomas and Capecchi, *Cell*, 51:503 (1987) for a description of homologous recombination vectors. The vector is introduced into an embryonic stem cell line (e.g., by electroporation) and cells in which the introduced DNA has homologously recombined with the endogenous DNA are selected. See e.g., Li et al., *Cell*, 69:915 (1992). The selected cells are then injected into a blastocyst of an animal (e.g., a mouse or rat) to form aggregation chimeras. See e.g., Bradley, in *Teratocarcinomas and Embryonic Stem Cells: A Practical Approach*, E. J. Robertson, ed. (IRL, Oxford, 1987), pp. 113–152. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously. recombined DNA. Knockout animals can be characterized for instance, for their ability to defend against certain pathological conditions and for their development of pathological conditions due to absence of the GBP-4 polypeptide.

GBP-4 polypeptides are useful in radioimmunoassays to measure guanine nucleotides such as GMP or GTP. Such a radioimmunoassay would be conducted as described in the literature using the naturally purified or recombinant GBP-4 as the GBP-4 element.

In addition, GBP-4 is useful for screening for compounds that bind to them as defined above. Preferably, these compounds are small molecules such as organic or peptide molecules that exhibit one or more of the desired activities. Screening assays of this kind are conventional in the art, and any such screening procedure may be employed, whereby the test sample is contacted with the GBP-4 herein and the extent of binding and biological activity of the bound molecule are determined.

GBP-4 is additionally useful in affinity purification of a guanine nucleotide that binds to GBP-4 (such as, for example, GTP and GMP) and in purifying antibodies thereto. The GBP-4 is typically coupled to an immobilized resin such as Affi-Gel 10™ (Bio-Rad, Richmond, Calif.) or other such resins (support matrices) by means well known in the art. The resin is equilibrated in a buffer (such as one containing 150 mM NaCl, 20 mM HEPES, pH 7.4 supplemented to contain 20% glycerol and 0.5% NP-40) and the preparation to be purified is placed in contact with the resin, whereby the molecules are selectively adsorbed to the GBP-4 on the resin.

The resin is then sequentially washed with suitable buffers to remove non-adsorbed material, including unwanted contaminants, from the mixture to be purified, using, e.g., 150 mM NaCl, 20 mM HEPES, pH 7.4, containing 0.5% NP-40; 150 mM NaCl, 20 mM HEPES pH 7.4 containing 0.5 M NaCl and 0.1% NP-40; 150 mM NaCl, 20 mM HEPES, pH 7.4 containing 0.1% deoxycholate; 150 mM NaCl, 20 mM HEPES, pH 7.4 containing 0.1% NP-40; and a solution of 0.1% NP-40, 20% glycerol and 50 mM glycine, pH 3. The resin is then treated so as to elute the guanine nucleotide using a buffer that will break the bond between the guanine nucleotide and GBP-4 (using, e.g., 50 mM glycine, pH 3, 0.1% NP-40, 20% glycerol, and 100 mM NaCl).

The GBP-4 molecules of the present invention may also be used to induce the formation of anti-GBP-4 antibodies, which are identified by routine screening as detailed below.

In addition to their uses above, the GBP-4 of the present invention is useful as the basis for assays of guanine nucleotide activity. Importantly, since such an assay measures a physiologically significant binding event, i.e., that of a guanine nucleotide to its GBP-4, triggering a detectable change {such as phosphorylation, cleavage, chemical modification, etc.), it is likely to be both more sensitive and more accurate than immunoassays, which detect the physiologically non-significant binding of a guanine nucleotide to anti-GBP-4 antibody.

Although more sensitive and accurate than antibodies, the GBP-4 molecules of the invention can be used to assay guanylate levels in a sample in the same ways in which antibodies are used.

For diagnostic purposes, the GBP-4 can be used in accordance with immunoassay technology. Examples of immunoassays are provided by Wide at pages 199–206 of *Radioimmune Assay Method*, Kirkham and Huner, ed., E & S. Livingstone, Edinburgh, 1970.

Thus, in one embodiment, GBP-4 molecules can be detectably labeled and incubated with a test sample containing guanine nucleotide molecules (such as biological fluids, e.g., serum, sputum, urine, etc.), and the amount of GBP-4 molecule bound to the sample ascertained.

Immobilization of reagents is required for certain assay methods. Immobilization entails separating the GBP-4 from any analyte that remains free in solution. This conventionally is accomplished by either insolubilizing the GBP-4 before the assay procedure, as by adsorption to a water-insoluble matrix or surface (Bennich et al., U.S. Pat. No. 3,720,760), by covalent coupling (for example, using glutaraldehyde cross-linking), or by insolubilizing the molecule afterward, e.g., by immunoprecipitation.

The foregoing are merely exemplary diagnostic assays for guanine nucleotides. Other methods now or hereafter developed for the determination of these analytes are included within the scope hereof.

Therapeutically, GBP-4 is useful in combating a variety of immunological and inflammatory responses, as well as many other pathological conditions such as multiple sclerosis and lung and intestinal-related disorders. GBP-4 is also used for counteracting or blocking an excess amount of a substance binding to it such as a guanine nucleotide. Without being limited to any one theory, it. may be useful as a mediator of any interferon-gamma-induced responses in macrophages and fibroblasts and may also function in other immune cell populations. In addition, GBP-4 is useful in treating myelodysplastic disorders, myeloproliferative syndromes, acute myeloid leukemia, and certain other types of cancer such as gastric, lung, or colon cancer or melanoma. The GBP-4 may be localized to the endoplasmic reticulum and may be involved in protein processing or trafficking.

Therapeutic formulations of the GBP-4 are prepared for storage by mixing the GBP-4 having the desired degree of purity with optional physiologically acceptable carriers, excipients, or stabilizers (*Remington's Pharmaceutical Sciences*, 16th edition, Osol, A. Ed. (1980)) in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or polyethylene glycol (PEG). The GBP-4 to be used for in vivo administration must be sterile. This is readily accomplished by filtration through sterile filtration membranes, prior to or following lyophilization and reconstitution. The GBP-4 ordinarily will be stored in lyophilized form or in solution.

Therapeutic GBP-4 compositions generally are placed into a container having a sterile access port, for example, an intravenous solution bag or vial having a stopper pierceable by a hypodermic injection needle.

The route of GBP-4 administration is in accord with known methods, e.g., injection or infusion by intraperitoneal, subcutaneous, intravenous, intraperitoneal, intracerebral, intramuscular, intraocular, intraarterial, or intralesional routes, or by sustained release systems as noted below. GBP-4 is administered continuously by infusion or by bolus injection.

Suitable examples of sustained-release preparations include semipermeable matrices of solid hydrophobic polymers containing the GBP-4, which matrices are in the form of shaped articles, e.g., films, or microcapsules. Examples of sustained-release matrices include polyesters, hydrogels (e.g., poly(2-hydroxyethyl-methacrylate) as described by Langer et al., *J. Biomed. Mater. Res.*, 15: 167–277 (1981) and Langer, *Chem. Tech.*, 12: 98–105 (1982) or poly (vinylalcohol)), polylactides (U.S. Pat. No. 3,773,919, EP 58,481), copolymers of L-glutamic acid and gamma ethyl-L-glutamate (Sidman et al., *Biopolymers*, 22: 547–556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133, 988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Microcapsules may be prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in *Remington's Pharmaceutical Sciences*, supra.

Sustained-release GBP-4 compositions also include liposomally entrapped GBP-4. Liposomes containing GBP-4 are prepared by methods known per se: DE 3,218,121; Epstein et al., *Proc. Natl. Acad. Sci. USA*, 82: 3688–3692 (1985); Hwang et al., *Proc. Natl. Acad. Sci. USA*, 77: 4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200–800 Angstroms) unilamellar type in which the lipid content is greater than about 30 mol. % cholesterol, the selected proportion being adjusted for the preferred GBP-4 therapy.

An effective amount of GBP-4 to be employed therapeutically for prevention or treatment of a disease or disorder will depend, for example, upon the therapeutic objectives, the route of administration, the severity and course of the disorder and its type, whether the GBP-4 is administered for preventative or therapeutic purposes, previous therapy, the patient's clinical history and response to the GBP-4, the condition of the patient, and the discretion of the attending physician. The polypeptide is suitably administered to the patient at one time or over a series of treatments.

Depending on the type and severity of the disease, about 1 μg/kg to 15 mg/kg (e.g., 0.1–20 mg/kg) of polypeptide is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of symptoms of the disorder occurs. However, other dosage regimens may be useful. The progress of this therapy is easily monitored by conventional techniques and assays.

Other therapeutic regimens may be combined with the administration of the GBP-4 polypeptides of the instant invention. For example, the patient to be treated with the polypeptides disclosed herein may also receive radiation therapy if the disorder is cancer. Alternatively, or in addition, a chemotherapeutic agent may be administered to the patient with cancer. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry (Williams & Wilkins: Baltimore, Md., 1992). The chemotherapeutic agent may precede or follow administration of the polypeptide or may be given simultaneously therewith. The polypeptide may be combined with an anti-oestrogen compound such as tamoxifen or an anti-progesterone such as onapristone (see, EP 616812) in dosages known for such molecules.

It may be desirable also to co-administer with the GBP-4 to the cancer patient antibodies against other tumor-associated antigens, such as antibodies which bind to HER-2, EGFR, ErbB2, ErbB3, ErbB4, or vascular endothelial factor (VEGF). Alternatively, or in addition, two or more anti-ErbB2 antibodies may be co-administered to the patient with the GBP-4. Sometimes, it may be beneficial also to administer one or more cytokines to the patient.

In a preferred embodiment, the polypeptide is co-administered with a growth-inhibitory agent to the cancer patient. For example, the growth-inhibitory agent may be administered first, followed by the polypeptide. However, simultaneous administration or administration of the polypeptide first is also contemplated. Suitable dosages for the growth-inhibitory agent are those presently used and may be lowered due to the combined action (synergy) of the growth-inhibitory agent and polypeptide. The antibodies, cytotoxic agents, cytokines, or growth-inhibitory agents are suitably present in combination in amounts that are effective for the purpose intended.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example, the container may be an intravenous solution bag or a vial having a stopper pierceable by a hypodermic injection needle). The active agent in the composition is the polypeptide. The label on, or associated with, the container indicates that the composition is used for treating the condition or disorder of choice. The article of manufacture may further comprise a second container comprising a pharmaceutically acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

F. Anti-GBP-4 Antibodies

The present invention further provides anti-GBP-4 polypeptide antibodies. Exemplary antibodies include polyclonal, monoclonal, humanized, bispecific, and heteroconjugate antibodies. The most preferred anti-GBP-4 antibodies (and antigen-binding fragments thereof) are those capable of preventing or inhibiting the binding of a guanine nucleotide to its GBP-4.

1. Polyclonal Antibodies

The anti-GBP-4 antibodies of the present invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the GBP-4 polypeptide or a fusion protein thereof. It may be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-GBP-4 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the GBP-4 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as PEG, to form a hybridoma cell. Goding, *Monoclonal Antibodies: Principles and Practice* (Academic Press: New York, 1986) pp. 59–103. Immortalized cell lines are usually transformed mammalian cells, particularly myeloma cells of rodent, bovine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high-level expression of antibody by the selected antibody-producing cells, and are sensitive to a medium such as HAT medium. More preferred immortalized cell lines are murine myeloma lines, which can be obtained for instance, from the Salk Institute Cell Distribution Center, San Diego, Calif., and the American Type Culture Collection, Manassas, Va. Human myeloma and mouse-human heteromyeloma cell lines also have been described for the production of human monoclonal antibodies. Kozbor, *J. Immunol*., 133:3001 (1984); Brodeur et al., *Monoclonal Antibody Production Techniques and Applications* (Marcel Dekker, Inc.: New York, 1987) pp. 51–63. Human myeloma and mouse-human heteromyeloma cell lines also have been described for the production of human monoclonal antibodies. Kozbor, *J. Immunol*., 133:3001 (1984); Brodeur et al., *Monoclonal Antibody Production Techniques and Applications* (Marcel Dekker, Inc.: New York, 1987) pp. 51–63.

The culture medium in which the hybridoma cells are cultured can then be assayed for the presence of monoclonal antibodies directed against a GBP-4 polypeptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem*., 107:220 (1980).

After the desired hybridoma cells are identified, the clones may be subcloned by limiting dilution procedures and grown by standard methods. Goding, supra. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, CHO cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567; Morrison et al., *Proc. Natl. Acad. Sci. USA*, 81: 6851–6855 (1984)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using routine techniques known in the art.

3. Humanized Antibodies

The anti-GBP-4 antibodies of the invention may further comprise humanized antibodies or human antibodies. Humanized forms of non-human (e.g., murine) antibodies are chimeric immunoglobulins, immunoglobulin chains, or fragments thereof (such as Fv, Fab, Fab', $F(ab')_2$, or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin, and all or substantially all of the FR regions are those of a human immunoglobulin consensus sequence. The humanized antibody preferably also will comprise at least a portion of an immunoglobulin constant region (Fc), typically that of a human immunoglobulin. Jones et al., *Nature*, 321:522–525 (1986); Riechmann et al., *Nature*, 332:323–329 (1988); and Presta, *Curr. Op. Struct. Biol.*, 2:593–596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 32:323–327 (1988); Verhoeyen et al., *Science*, 239:1534–1536 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage-display libraries. Hoogenboom and Winter, *J. Mol. Biol.*, 227:381 (1991); Marks et al., *J. Mol. Biol.*, 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.*, 147(1):86–95 (1991).

4. Bispecific Antibodies

Bispecific antibodies are monoclonal, preferably human or humanized, antibodies that have binding specificities for at least two different antigens. In the present case, one of the binding specificities is for a GBP-4 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities. Milstein and Cuello, *Nature*, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies may be prepared in vitro using known methods in synthetic protein chemistry, including those involving cross-linking agents. For example, immunotoxins may be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

G. Uses for anti-GBP-4 Antibodies

The antibodies of the invention may be used as affinity purification agents. In this process, the antibodies are immobilized on a solid phase such a SEPHADEX™ resin or filter paper, using methods well known in the art. The immobilized antibody is contacted with a sample containing the GBP-4 polypeptide (or fragment thereof) to be purified, and thereafter the support is washed with a suitable solvent that will remove substantially all the material in the sample except the GBP-4 protein, which is bound to the immobilized antibody. Finally, the support is washed with another suitable solvent, such as glycine buffer, pH 5.0, that will release the GBP-4 polypeptide from the antibody.

Anti-GBP-4 antibodies may also be useful in diagnostic assays for GBP-4 polypeptide, e.g., detecting its expression in specific cells, tissues, or serum. Thus, the antibodies may be used in the diagnosis of human malignancies (see, for example, U.S. Pat. No. 5,183,884).

For diagnostic applications, the antibody typically will be labeled with a detectable moiety. Numerous labels are available which can be preferably grouped into the following categories:

(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. (Wiley-Interscience: New York, 1991), for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin, and Texas Red are available. The fluorescent labels can be conjugated to the antibody using the techniques disclosed in *Current Protocols in Immunoloay*, supra, Coligen, ed., for example. Fluorescence can be quantified using a fluorimeter.

(c) Various enzyme-substrate labels are available and U.S. Pat. No. 4,275,149 provides a review of some of these. The enzyme preferably catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym*., Vol. 73, Langone and Van Vunakis, eds. (Academic Press: New York, 1981), pp. 147–166.

Examples of enzyme-substrate combinations include:

(I) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (4-methylumbelliferyl-β-D-galactosidase).

Numerous other enzyme-substrate combinations are available to those skilled in the art. For a general review of these, see, for example, U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-GBP-4 antibody need not be labeled, and the presence thereof can be detected using a labeled antibody which binds to the anti-GBP-4 antibody.

The antibodies of the present invention may be employed in any known assay method, such as competitive binding assays, direct and indirect sandwich assays, and immunoprecipitation assays. Zola, *Monoclonal Antibodies: A Manual of Techniques* (New York: CRC Press, Inc., 1987), pp.147–158.

Competitive binding.assays rely on the ability of a labeled standard to compete with the test sample analyte for binding with a limited amount of antibody. The amount of GBP-4 protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Preferably, the antibody is labeled with a radionuclide (such as $^{111}$In, $^{99}$Tc, $^{14}$C, $^{131}$I, 125I, $^{3}$H, $^{32}$p or $^{35}$S) so that the tumor can be localized using immunoscintiography.

Additionally, anti-GBP-4 antibodies may be useful as antagonists to GBP-4 functions where, for example, GBP-4 is upregulated in cancer cells or stimulates their proliferation or is upregulated in inflammatory tissue or immune functions. Hence, for example, the anti-GBP-4 antibodies may by themselves, or in combination with a chemotherapeutic agent, growth inhibitory agent, radiation, or other cancer treatment or drug such as anti-HER-2 or erbB antibodies, be effective in treating certain forms of cancer such as gastric cancer, colon- cancer, lung cancer, and melanoma. Combination treatment is further described above under uses of GBP-4. Further uses for the antibodies include inhibiting immunological, inflammatory, or structural disorders or the binding of GBP-4 to a guanine nucleotide. For therapeutic use, the antibodies can be used in the formulations, schedules, routes, and doses indicated above under uses for the GBP-4 polypeptides. In addition, GBP-4 antibody may be administered into the lymph as well as the blood stream.

As a matter of convenience, the anti-GBP-4 antibody of the present invention can be provided in a kit format, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer), and the like. The relative amounts of the various reagents may be varied widely to provide for concentrations in solution of the reagents which substantially maximize the sensitivity of the assay. Particularly, the reagents may be provided as dry powders, usually lyophilized, including excipients which on dissolution will provide a reagent solution having the appropriate concentration.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example I

Cloning of Human GBP-4

1. Materials and Methods

Cells and Reagents

The following cell lines were obtained from the American Type Culture Collection (Manassas, Va.) and grown as recommended: 293, human embryonic kidney cells, HeLa, human epitheloid carcinoma of the cervix (ATCC, CCL-2), A431, human epidermoid carcinoma (ATCC, CRL-1555), RF-1, derived from a human primary gastric adenocarcinoma (ATCC, CRL-1864), RF-48, derived from a human gastric adenocarcinoma metastatic to peritoneal fluid (ATCC, CRL-1863), AGS, derived from a human primary gastric adenocarcinoma (ATCC, CRL-1739), KATO III, a human gastric carcinoma metastatic to pleural fluid (ATCC, HTB-103), and Hs746T, derived from a human stomach carcinoma metastatic to the left leg (ATCC, HBT-135). Purified recombinant human IFN-γ was obtained from Genentech, Inc. The rHuIFN-γ and rHuIFN-α used in this example displayed specific anti-viral activities of $2\times10^7$ and $5\times10^6$ IU/mg, respectively (1.0 IU of IFN-α per ml=30 fM of IFN-α; 1.0 IU of IFN-γ per ml=2.9 μm of IFN-γ). L-($^{35}$S)methionine (1000Ci/mmol) and (α-$^{32}$P)CTP (3000 Ci/mmol) were purchased from Amersham. Mouse monoclonal $^{RGS}$His antibody specific for the amino acid sequence Arg-Gly-Ser-$(His)_4$ (SEQ ID NO:33) was purchased from Qiagen. Human stomach tissue was obtained within five minutes of removal of the pathological specimen. Sections were taken in the same specimen from gastric adenocarcinoma and from grossly normal appearing gastric antrum. Tissue was immediately frozen in liquid nitrogen and stored at −70° C.

Suppression Subtractive Hybridization

Human GBP-4 was isolated independently by differential screening using suppression subtractive hybridization (SSH), as described by Diatchenko et al., *Proc. Natl. Acad. Sci. USA*, 93: 6025–6030 (1996). SSH was carried out using the PCR-SELECT® cDNA Subtraction Kit (Clontech Laboratories, Inc.) according to the manufacturer's protocol. Tester double-stranded (ds) cDNA was synthesized from 2 μg of poly A+RNA isolated from the stomach tumor surgical tissue. Driver ds cDNA was synthesized from 2 μg of poly A+RNA isolated from normal stomach tissue from the same specimen.

PCR was performed using the Clontech kit, including the cDNA synthesis primer (SEQ ID NO:19), adaptors 1 and 2 (SEQ ID NOS:20 and 21, respectively) and complementary sequences for the adaptors (SEQ ID NOS:22 and 23, respectively), PCR primer 1 (SEQ ID NO:24), PCR primer 2 (SEQ ID NO:25), nested PCR primer 1 (SEQ ID NO:26), nested PCR primer 2 (SEQ ID NO:27), control primer G3PDH5' primer (SEQ ID NO:28), and control primer G3PDH3' primer (SEQ ID NO:29), shown in FIG. 5.

Figure 6:
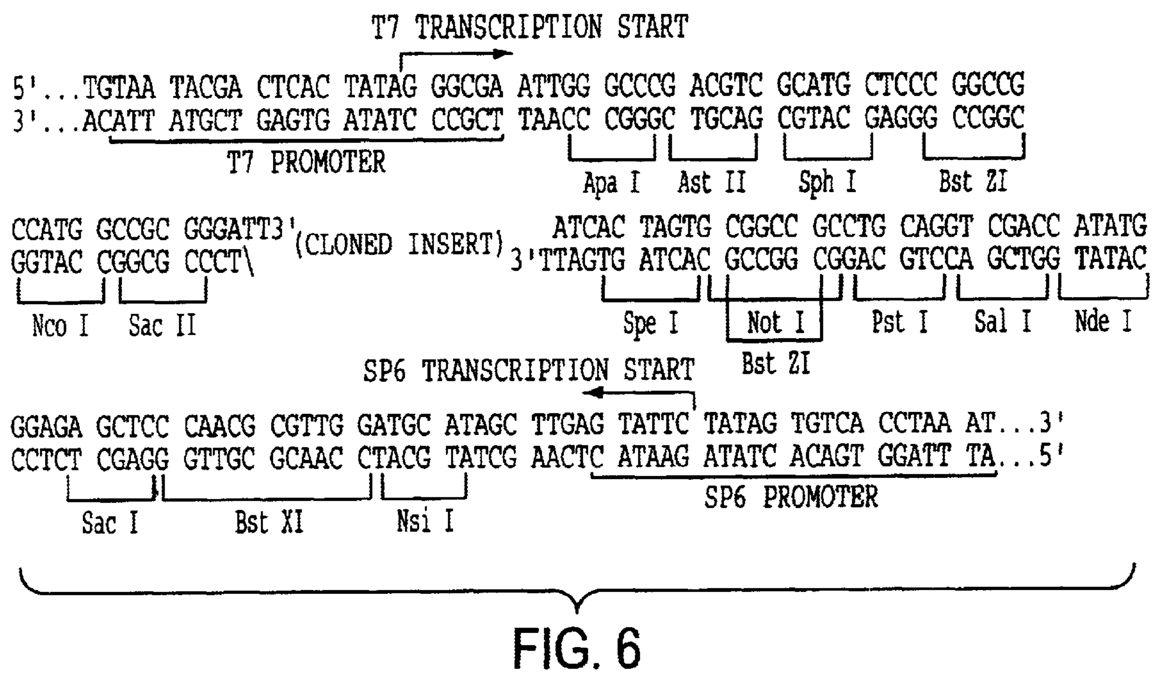
FIG. 6 shows the cloning site region of the plasmid pGEM-T used to clone the GBP-4 sequence herein (SEQ ID NOS:30 and 31 for 5' and 3' sequences, respectively).

Products generated from the secondary PCR reaction were inserted into the cloning site region of pGEM-T vector (Promega), shown in FIG. 6 (SEQ ID NOS:30 and 31 for 5' and 3' sequences, respectively). Plasmid DNAs were prepared using the Wizard Miniprep Kit™ (Promega). DNA sequencing of the subcloned PCR fragments was performed manually by the chain termination reaction (SEQUENASE™ 2.0 Kit, Pharmacia). Nucleic acid homology searches were performed using the BLAST program noted above.

Certain clones were sequenced out of those found. Out of these, a certain number of templates were prepared. A program was used to trim the vector off, and a different program used to cluster the clones into two or more identical clones or with an overlap of 50 bases the same. Then a BLAST was performed of a representative clone from the cluster. Primers were designed for RT-PCR to see if the clones were differentially expressed.

Semi-quantitative RT-PCR

Cell lines were treated with 10,000 units/ml IFN-α and varying doses of recombinant IFN-γ for varying time periods as indicated. Total RNA was extracted using Stat-60™ (Tel-Test B™) per manufacturer's instructions. First strand cDNA was prepared from 0.1 μg–3 μg of total RNA with the Superscript RT™ kit (Gibco, BRL) PCR amplification of 5 μl of first strand cDNA was performed in a 50 μl PCR reaction. Primers corresponding to nucleotide positions 380–403 (sense) and 506–529 (anti-sense) of the human GBP-4 cDNA, positions 1440–1463 (sense) and 1808–1831 (anti-sense) of the human GBP-1 cDNA, and positions 632–655 (sense) and 874–897(anti-sense) of the human GBP-2 cDNA were used to amplify first strand cDNA. As controls, primers corresponding to nucleotide positions 450–471 (sense)and 642–663 (anti-sense) of human glyceraldehyde-3-phosphate dehydrogenase (GAPDH) or 707–729 (sense; 5'-GTGGCCCATGCTCTGGCAGAGGG (SEQ ID NO:34)) and 1048–1071 (anti-sense; 5'-GCACCACCCCACAAGGAAGCCATCC (SEQ ID NO:35)) of human triosephosphate isomerase (huTPI) (Maquat et al., *J. Biol. Chem.*, 260: 3748–3753 (1985); Brown et al., *Mol. Cell. Biol.*, 5: 1694–1706 (1985)) were used to amplify first strand cDNA.

Briefly, 4 μCi (α-$^{32}$P)CTP (3000Ci/mmol) was added to each reaction with 2.5U of TaKaRa Ex Taq™ (Panvera, Madison, Wis.) and 0.2 μm of each dNTP. The reactions were amplified in a 480 PCR thermocycler™ (Perkin Elmer) using the following conditions: 94° C. for 1 min., 59° C. for 30 sec., 72° C. for 1 min., for 18 cycles. 5 μl of PCR products were electrophoresed on a 6% polyacrylamide gel. The gel was exposed to an imaging plate and scanned with an image analyzer (BAS 2000™, Fuji). Densitometry measurements were obtained using MacBAS™ ver2.1 software (Fuji) to quantitate the GAPDH or TPI and gene-specific products.

Northern Blot Analysis

Adult multiple-tissue Northern blots (Clontech) and the Northern blot of normal stomach and stomach tumor poly A+RNA (2 μg/lane) were hybridized with a 127-bp human GBP-4 probe (amino acids 128 through 169). The membranes were washed in 0.1×SSC at 55° C.–65° C. and exposed for autoradiography. Blots were rehybridized with a 75-bp synthetic probe from the human β-actin gene. See Godowski et al., *Proc. Natl. Acad. Sci. USA*, 86: 8083–8087 (1989) for a method for making a probe with overlapping oligos, which is how the actin probe was prepared.

cDNA Library Screening

In order to isolate a full-length clone for ts52, several cDNA libraries (λgt10 and λDR2) were screened by PCR using primers from the original partial ts52 sequence isolated by the PCR-Select® protocol, as follows: hu.GBP4.top1 (5'-CCGGACACGGCAAAGTAACATCCT; SEQ ID NO:36), ts52sp6.pcr.top1 (5'-GTACAATACTGTGAACAAAATTG; SEQ ID NO:37), ts52sp6.top2 (5'-GGGTGCTATCGACCTACTGCAC; SEQ ID NO:38), ts52sp6.pcr.bot1 (5'-GAGTCAGCAGGATCTTCAACCCTG; SEQ ID NO:39), huGBP4.top3 (5'-GTGCAGCTGCCCATGGAAACCCTC; SEQ ID NO:40), huGBP4.bot4 (5'-CTGCTGAGAGCCACAAGATCTTGC; SEQ ID NO:41), and huGBP4.bot3 (5'-

CCCAGACTTTCTGGCTCCAGACTC; SEQ ID NO:42). Of those examined, three libraries, a human fetal liver, an adult human heart, and an adult human spleen (Clontech), contained the expected size fragment and were screened for full-length clones. The inserts of several of these clones were subcloned into pBluescript IISK+™ and the DNA sequences of six independent subclones determined by dideoxy DNA sequencing on both strands.

For mammalian cell expression, a cytomegalovirus-based expression vector called pRK5, described in Gorman et al., *DNA and Protein Engineering Techniques*, 2: 1 (1990) and in EP 307,247 published Mar. 15, 1989, was employed as the expression vector in which the GBP-4 cDNA (from clone ts52.1b from the λgt10 heart cDNA library) was inserted. The vector was made using standard ligation methodology as described in Sections 5.10 to 5.11 of Sambrook et al., supra. The resulting vector codes for a fusion protein between the oligopeptide Met-Arg-Glu-Ser-$(His)_6$-Gly-Ser (SEQ ID NO:43) and human GBP-4 from amino acid residue 2 to 591. This plasmid, designated pRK5-based plasmid pRK5.hu.GBP4.histag.71, is deposited with the American Type Culture Collection as ATCC No. 209,456.

GBP Chromosomal Localization

To perform radiation hybrid mapping of the human GBP genes, the medium resolution Stanford G3™ panel of 83 clones of the whole human genome was obtained from Research Genetics, Inc. Oligonucleotide primers and conditions were developed for specifically amplifying a portion of the GBP genes from genomic DNA by PCR. The top primer of human GBP-4 corresponded to nucleotide positions 147–170 and the bottom primer was complementary to positions 657–680. A 3016-bp product was observed on agarose gel electrophoresis when human DNA but not hamster DNA was used as template. The top primers for GBP-1 and GBP-2 corresponded to nucleotide positions 1440–1463 and 632–655, respectively, and the bottom primers were complementary to positions 1808–1831 and 874–897, respectively. A 2028-bp product was observed for GBP-1 and a 593-bp product seen for GBP-2. Scoring was then carried out for the presence or absence of the PCR products in 83 radiation hybrid DNA samples. PCR reactions were performed for 35 cycles (94° C. for 1 min, 59° C. for 30 sec, 72° C. for 2.5 min) in a total reaction volume of 25 μl with 82.5 ng of each primer, 62.5 ng of DNA from each of the 83 clones, and 5.0 units of TaKaRa Ex Taq™ polymerase. To confirm that the product obtained corresponded to the GBP gene of interest, a Southern blot was performed on the gel, using probing with a primer that was located internal to the primers used for the PCR. The LOD score is the total relative probability, expressed on a logarithmic scale, that a linkage relationship exists between the gene of interest and the indicated loci. All markers within a 1000:1 bin are ordered at greater than 1000:1 odds with respect to all markers outside the bin. The probability that a marker resides at the indicated position within a particular bin is 75%.

Binding of human GBP-4 to Nucleotide-Coupled Agarose Beads

In vitro synthesis of GBP-4 was performed using the TNT® Coupled Reticulocyte Lysate System (Promega) according to the manufacturer's instructions, to synthesize $(^{35}S)$methionine-labeled GBP-4 from 1–2 μg of pRK5.huGBP-4.his plasmid. Nucleotide agarose binding assays were performed as described by Cheng et al., (1991), supra. Briefly, 2 μl of reticulocyte lysate containing in vitro synthesized GBP-4 were mixed in 70 μl of binding buffer (20 mM Tris-HCl, pH 7.5, 150 mM NaCl, 5 mM $MgCl_{21}$ 0.1% Triton X-100) and incubated with 30 μl of packed nucleotide-coupled agarose beads (Sigma) equilibrated with binding buffer. The bead mixture was incubated on ice for 30 minutes with occasional mixing, and washed three times with 1 ml of cold binding buffer. Bound protein was eluted by heating for 3 min to 100° C. in 30 μl of 2×SDS sample buffer. A total of 25 μl of the heated sample was electrophoresed on a 4–20% polyacrylamide gel (Novex). The gel was fixed, soaked in Amplify™ (Amersham), dried, and exposed to film. The binding experiments were performed at least four times with similar results.

Immunoelectron Microscopy

Human embryonic kidney 293 cells (Graham et al., *J. Gen. Virol.*, 36: 59 (1977), subclone 293TSA transfected with the temperature-sensitive large T-antigen gene) were transiently transfected with 1–2 μg of pRK5.hu.GBP-4.his. Briefly, the 293 cells were grown to 70% confluence in 6-well plates in a DMEM:F12 (1:1) medium containing 1 mM HEPES buffer, 0.29 g/l glutamine, 2.44 g/l sodium bicarbonate, 0.55 g/l sodium pyruvate, pH 6.95, supplemented with 10% whole fetal calf serum. The day before the transfection the cells were counted, the medium was aspirated off, and the cells were trypsinized and resuspended in a lipofectamine medium. Then the suspension was adjusted to 266,000 cells/ml, seeded at 3 ml per well of a six-well plate (800,000 cells/well), and incubated until the day of the transfection.

A total of 5 μg of the plasmid DNA (pRK5.hu.GBP4-histag.71) was dissolved in 150 μl of 1 mM Tris-HCl, 0.1 mM EDTA, 0.227 M $CaCl_2$. Added to this (dropwise while vortexing) was 150 μl of 50 mM HEPES buffer (pH 7.35), 280 mM NaCl, 1.5 mM $NaPO_4$, and the precipitate was allowed to form for ten minutes at 25° C. The suspended precipitate was then added to the cells in the 60-mm tissue culture plate and allowed to settle overnight in the incubator. The medium was then aspirated off and replaced with DMEM:F12 (1:1)-based serum-free medium, PS-04, containing insulin, transferrin, trace elements, and lipids. U.S. Pat. No. 5,122,469. The cells were then analyzed by standard—detection techniques for positive expression with the $^{RGS}$His Antibody (Qiagen Inc.), which is a purified mouse monoclonal antibody specific for the amino acid sequence Arg-Gly-Ser-His-His-His-His (SEQ ID NO:33). GBP-4 expression was detected.

The transfected cells were grown in 35-mm Petri dishes for 24–48 hr., washed in serum-free medium, and processed as described in McLean and Nakane, *J Histochem Cytochem*, 22: 1077–1083 (1974). Briefly, the cells were fixed in 2% formaldehyde/lysine/phosphate buffer, permeabilized with 0.5% saponin-PBS, immunolabeled with anti-his mouse monoclonal antibody and then with peroxidase-conjugated anti-mouse IgG (Boehringer Mannheim Co.) in the presence of 0.5% saponin. The samples were incubated with hydrogen peroxide and diaminobenzidine (DAB) at room temperature for 1 hr, fixed in 1% reduced osmium, dehydrated through graded ethanols and propylene oxide, and embedded in eponate-12-epoxy monomer resin. Ultrathin sections were cut and mounted on 200-mesh thin bar hexagonal copper grids, counterstained with ethanolic uranyl acetate and lead citrate and examined in a Philip CM12™ transmission electron microscope.

Antiproliferation Assay

KATO III and AGS cells were plated in duplicate in 96-well plates (5000 cells/well) with varying concentrations of IFN-γ as indicated. The plates were incubated for 24–96 hours. At the end of the incubation, living cells were determined using the CellTiter 96 Proliferation Assay Kit™

(Promega) according to the manufacturer's instructions. The absorbance at 595 nm was recorded using an ELISA plate reader (Molecular Devices).

In situ Hybridization ($^{33}$P)-labeled sense and antisense riboprobes were transcribed from PCR products obtained from plasmids containing cDNA inserts for human GBP-4. The PCR products were designed to carry T3 (antisense) and T7 (sense) RNA polymerase promoters at either end. Riboprobes were transcribed from an 805-bp PCR product corresponding to nucleotides 1195–1945 of human GBP-4. All human tissues were formalin fixed and paraffin embedded. Samples included tissue from the original gastric carcinoma and adjacent uninvolved gastric mucosa, normal liver, hepatocellular carcinoma, ductal carcinoma of the breast, poorly differentiated keratinizing squamous carcinoma of the lung, and transverse thoracic and abdominal sections from a fetus (approximate gestational age 16 weeks). For in situ hybridization, sections were deparaffinized and then digested with 20 μg/ml proteinase K at 37° C. for 15 minutes prior to applying the probe. Following overnight hybridization, sections were treated with 20 μg/ml RNase A, followed by a high stringency wash in 0.1×SSC at 55° C. Sections were dehydrated, dipped in NTB-2 emulsion, and exposed for 3 weeks.

2. Results

Identification of ts52 by Suppression Subtractive Hybridization

A recent PCR-based selection strategy, SSH (Diatchenko et al., supra), was employed to identify genes selectively expressed in a gastric adenocarcinoma. This technique combines a high subtraction efficiency with an equalized representation of differentially expressed sequences. The advantage of SSH over other methods is that it combines normalization and subtraction in a single procedure and has been shown to enrich over 1000-fold for rare sequences in one round of subtractive hybridization. This method is based on specific PCR reactions that permit exponential amplification of cDNAs which differ in abundance, whereas amplification of sequences of identical abundance in two population is suppressed.

The SSH technique was employed to isolate genes expressed in a gastric adenocarcinoma whose expression is reduced or absent in normal stomach tissue. Poly A+RNA extracted from a freshly isolated human gastric cancer was used to synthesize tester cDNA, and polyA+RNA made from normal stomach tissue from the same surgical specimen was used to synthesize driver cDNA. The degree of subtraction efficiency was monitored by Southern blot analysis of unsubtracted and subtracted PCR products using a β-actin probe. No β-actin mRNA was apparent in the subtracted PCR products, confirming the efficiency of the subtraction. The subtracted cDNA library was subcloned into the pGEM-T vector (FIG. 6) for further analysis. A random sample of 127 clones was sequenced from the transformed colonies obtained. Eighty-seven of the sequences obtained matched known genes, and the remainder were either matches with expressed sequence tags (ESTs) or had no match with any sequences in the databases. In order to determine whether the clones obtained were differentially expressed, PCR primers were designed for selected clones and semi-quantitative RT-PCR and Northern analysis were performed using stomach tumor mRNA and normal stomach mRNA.

One clone, ts52, was of particular interest and pursued further because it fulfilled the criteria for differential expression. No expression of ts52 was detected in the normal stomach tissue mRNA either by RT-PCR or Northern blot. In contrast, prominent expression of ts52 mRNA was observed in the stomach tumor mRNA by both RT-PCR and Northern analysis. Multiple ts52 mRNA species were identified on the Northern blot in the tumor RNA sample with two major transcripts of 2.8 and 5.0 kb.

ts52 is Homologous to Interferon-induced Guanylate Binding Proteins

The cDNA sequence of clone ts52 was 951 bp in length and contained a single open reading frame. See FIG. 1. Significant homology was seen at the DNA and protein level with several interferon-induced mammalian guanylate binding proteins. At the amino acid level, the open reading frame of this clone was 73% identical to amino acids 129–316 of human GBP-1 and 68% identical to the corresponding region of human GBP-2. See FIG. 2. The high sequence homology indicated that this was a potential new GBP family member. Partial sequence for a gene with high homology to both GBP-1 and GBP-2 has been identified and named humanr GBP-3. Strehlow et al., *Gene*, 144: 295–299 (1994). The GBP-3 sequence encodes 64 amino acids that share 86% amino acid sequence homology with the carboxyl terminal region of GBP-1 (FIG. 2). The open reading frame of the ts52 cDNA is not identical to the partial sequence reported for GBP-3 (27% homology). Therefore, the newest member of this family is designated human GBP-4.

Isolation of the Full-length Human GBP-4 cDNA

Clones encoding human GBP-4 were isolated by screening several cDNA libraries (λgt10 and λDR2) by PCR. The DNA sequence of the insert of clone ts.52.1b from the λgt10 heart cDNA library was 2024 bp in length and contained an open reading frame encoding a protein of 591 amino acids (FIG. 1) with a predicted relative molecular mass of 67,049 ($M_r$67k). The encoded protein sequence contains three potential N-linked glycosylation sites. GBP-4 lacks a hydrophobic N-terminal sequence indicative of a secretion signal and lacks transmembrane domains, which suggests that it is an intracellular protein. The other five clones contained partial overlapping sequence with ts.52.1b. The amino acid sequence encoded by the full-length ts.52.1b cDNA is 67% identical to human GBP-1 and 64% identical to human GBP-2 (FIG. 2). The C-terminal 63 amino acids of GBP-4 diverge from both GBP-1 and GBP-2, whereas only the C-terminal 28 amino acids of GBP-1 and GBP-2 differ significantly.

A comparison of the amino acid sequence of GBP-4 with five mammalian homologs and a recently described GBP from chickens indicates a high degree of homology (37–67%)(FIGS. 3A–3B and 4). The individual family members are also highly related across species.

GBP-4 contains the tripartite GTP-binding motifs, GXXXXGK(S/T) (SEQ ID NOS: 7 and 8, respectively), DXXG (SEQ ID NO:9), and (N/T)KXD (SEQ ID NOS:10 and 11, respectively) in the amino-terminal region of the protein (FIGS. 1 and 2). Unlike all other mammalian GBPs and chicken GBP which contain no (N/T) KXD motif (SEQ ID NOS:10 and 11, respectively), GBP-4 contains two (N/T)KXD sequences (SEQ ID NOS:10 and 11, respectively) at positions 109–112 and 132–135 that conform to the third motif of the GTP binding consensus domain. There are seven di-leucine motifs in the protein that may serve as intracellular protein sorting signals (FIGS. 1 and 2).

GBP-4 has a unique C-terminal region. GBP-1 and GBP-2 contain a C-terminal CXXX box (SEQ ID NO:12) which is a cysteine residue followed by two aliphatic amino acids and another amino acid. Mutation studies on Ras proteins have identified these four C-terminal amino acids as essential for isoprenoid modification and define the cysteine as the site of isoprenoid attachment. The serine at the last position of this box is a signal for the farnesyl transferase. GBP-1, which has a TIS sequence after the cysteine (FIG. 2) has been shown to be prenylated by farnesyl transferase. GBP-4 contains a FIS sequence after the cysteine at amino acid positiond 555–557 which, together with the Cys at position 554, may be a prenylation site.

GBP-4, but not GBP-1 or GBP-2, is Differentially Expressed in a Gastric Tumor

In order to determine whether GBP-1 and GBP-2 were also differentially expressed in the stomach tissue, the expression of GBP-1, GBP-2, and GBP-4 was compared by semi-quantitative RT-PCR. GBP-4 was expressed only in the tumor tissue, whereas GBP-1 and GBP-2 were expressed in both the normal stomach and the gastric adenocarcinoma.

GBP-4 mRNA is Highly Expressed in Immune Tissues

A GBP-4 PCR fragment was used as a probe to evaluate the size of GBP-4 mRNA and its expression in different human tissues by Northern blot analysis. Two strongly hybridizing MRNA species of approximately 2.8 and 5.0 kb and three weaker hybridizing bands of 3.9, 6.8, and 8.3 kb were detected with the human GBP-4 probe after washing the blots at high stringency. The highest expression for all five mRNA species was seen in peripheral blood leukocytes and adult spleen. The 2.8-kb band on the Northern blots is slightly larger than the size of the consensus sequence (2.3 kb) from two clones ts.52.1b and ts52.1c. Since these clones did not include 3' sequences containing a poly A+tail, the length of the 3' region of human GBP-4 is not known and could account for this difference. Without being limited to any one theory, the different-sized transcripts may contain additional untranslated sequences not present in the GBP-4 clones described herein, represent alternatively spliced transcripts, or may encode GBP-4-related proteins. The mRNA expression pattern indicates that GBP-4 is highly expressed in immune tissues.

Chromosomal Localization of the Genes for GBP-1, GBP-2, and GBP-4

The gene for human GBP-1 had been previously localized to chromosome 1, but no cytogenetic location had been determined.

Strehlow et al., *Gene*, 144: 295–299 (1994). The chromosomal location of the genes for GBP-1, GBP-2, and GBP-4 was determined by radiation hybrid mapping using the Stanford G3 Radiation Hybrid Panel™. Listed in Table I are the LOD scores obtained for the Stanford Human Genome Center (SHGC) framework markers which link with each GBP gene with a LOD score of 6.0 or greater. Eleven of the nineteen SHGC markers in bin 37 of the Chromosome 1 radiation hybrid (RH) map are listed as a Genome Database (GDB) locus in the order they appear in the RH map. The corresponding Genethon marker, and cytogenetic location for the markers that have been mapped, are also shown. In italics are the markers which link with the human GBP-1, GBP-2, and GBP-4 genes.

Like the gene for GBP-1, the genes for GBP-2 and GBP-4 also localize to chromosome 1. All three genes reside near the meiotid markers D1S3150 and D1S1575, which lie between D1S2865 and D1S435 on the Genethon genetic map (Table I). This places the GBP genes in band 1p31-1p32. Thus, there appears to be a close physical linkage between these three members of the interferon-induced GBP gene family in the human genome.

TABLE I

Chromosome Localization of Human GBP-1, GBP-2, and GBP-4

| 1000:1 | GDB | Génethon | LOD Score | | | Cyto-ge-netic Loca- |
|---|---|---|---|---|---|---|
| Bin | Locus | Marker | GBP-1 | GBP-2 | GBP-4 | tion |
| 37 | D1S208 | AFM120xa5 | | | | 1p32-1p33 |
| 37 | D1S2774 | AFMb335xb5 | | | | |
| 37 | D1S488 | AFM299ze9 | | | | 1p31-p32 |
| 37 | D1S401 | | | | | |
| 37 | D1S3544 | | | | | |
| 37 | D1S3283 | | 6.086 | | | |
| 37 | D1S2865 | AFMa050ta5 | 6.032 | | | |
| 37 | D1S3261 | | 9.153 | 6.466 | | |
| 37 | D1S3150 | | 10.555 | 12.523 | 10.818 | |
| 37 | D1S1575 | | 8.432 | 9.932 | 10.818 | |
| 37 | D1S435 | AFM217zb2 | | 6.516 | | |

GBP-4 is an Intracellular Membrane-associated Protein

Examination of the predicted amino acid sequence revealed the absence of a conventional signal sequence, which suggested that GBP-4 is an intracellular protein. To determine its subcellular location, 293 or A431 cells were transfected with an expression vector for an epitope-tagged GBP-4 and processed for transmission electron microscopy as described in Materials and Methods above. The DAB reaction product, which indicates the presence of GBP-4, was observed in membrane-bound vesicles that morphologically correspond to endolysosomes, which are endosomes located at the periphery or close to the perinuclear region of transfected A431 cells. At higher magnification, the reaction product (GBP-4 DAB diffusion product) was associated with the inner face of the limiting endosomal membrane, which suggests that GBP-4 is associated with the membrane and projects into the lumen of the endosomes. Multivesicular bodies and lysosomes with a heterogeneous content that include vesicles, membrane whorls, and multilamellar structures were also labeled. Other morphologically distinct early endocytotic carriers such as coated vesicles were not immunolabeled. GBP-4 was not detected in control untransfected cells.

GBP-4 Binds to ADP, CDP, and UDP in Addition to Guanine Nucleotides

The initial characterization of the GBPs describes their ability to bind agarose-immobilized guanine nucleotides. Cheng et al., (1991), supra. GBP-1 demonstrates high specificity for GTP, GDP, and GMP but not adenine, uracil, or cytosine nucleotides. The specificity of binding of in vitro-synthesized GBP-4 to a panel of agarose-coupled nucleotides was determined. Under the binding and washing conditions used, GBP-4 bound most efficiently to GDP, GTP. and ADP agarose beads, and was also recovered by CDP, UDP, and to a lesser extent, GMP agarose (FIG. 7). Thus, unlike GBP-1 which shows strict guanine nucleotide binding affinity, GBP-4 is less specific.

GBP-4 is Induced by Interferon-γ

Interferon-induced GBPs have been identified as abundant proteins synthesized after interferon treatment of cells. Cheng et al., *J. Interferon Res*, 6: 417–427 (1986). IFN-γ is the most potent inducer of GBP-1, but IFN-α can also induce GBP-1 expression. Briken et al., *Mol Cell Biol*, 15: 975–982 (1995). In order to determine if GBP-4 is induced following interferon treatment, HeLa cells were treated with IFN-α or IFN-γ and the induction of GBP-4 mRNA was compared with that of GBP-1 and GBP-2 by a semi-quantitative RT-PCR assay. In untreated cells, no mRNA was seen for GBP-1, GBP-2, or GBP-4. In cells treated with 10,000 units/ml IFN-α for 5 hr, GBP-1 was induced, but no expression of GBP-2 or GBP-4 was detected. IFN-γ treatment (100 ng/ml) for 18 hr induced the mRNA for all three GBPs. Very strong induction was seen for GBP-1, while weaker induction was detected for GBP-2 and GBP-4. These findings demonstrate that, in HeLa cells, IFN-γ but not IFN-α induces GBP-4 mRNA.

GBP-4 Expression in Gastric Cancer Cell Lines

Since GBP-4 was observed to be differentially expressed in gastric adenocarcinoma, the regulation of GBP-4 by IFN-γ in gastric tumors was examined. As additional clinical material was not available, GBP expression in response to IFN-γ was analyzed in all of the available gastric cancer cell lines from the ATCC: Hs746T, RF-1, RF-48, AGS, and KATO III. Cell lines were grown in media alone or were treated with IFN-γ (100 ng/ml) for 5 or 24 hours, total RNA was isolated, and GBP expression was analyzed by semi-quantitative RT-PCR. No endogenous expression of GBP-1, GBP-2, or GBP-4 was detected in any of the untreated cell lines.

After IFN-γ treatment for 5 hours, GBP-4 mRNA was detected in RF-1 and RF-48 cells. After 24 hours of interferon treatment, GBP-4 expression was detectable in all cell lines except in the KATO III cells, which showed little if any expression of GBP-4. The expression pattern of GBP-1 and GBP-2 differed from that of GBP-4. GBP-1 was induced at 5 and 24 hours of IFN-γ treatment in Hs746T cells, AGS, and KATO III, but not in RF-1 or RF-48 cells. GBP-2 mRNA was detectable at 5 and 24 hours in all cell lines except AGS tumor cells. The pattern of GBP expression differed in these gastric cancer cell lines, which suggests that the GBPs are not coordinately regulated by IFN-γ.

Proliferation Effect of IFN-γ on Gastric Cancer Cell Lines

Figure 7A:
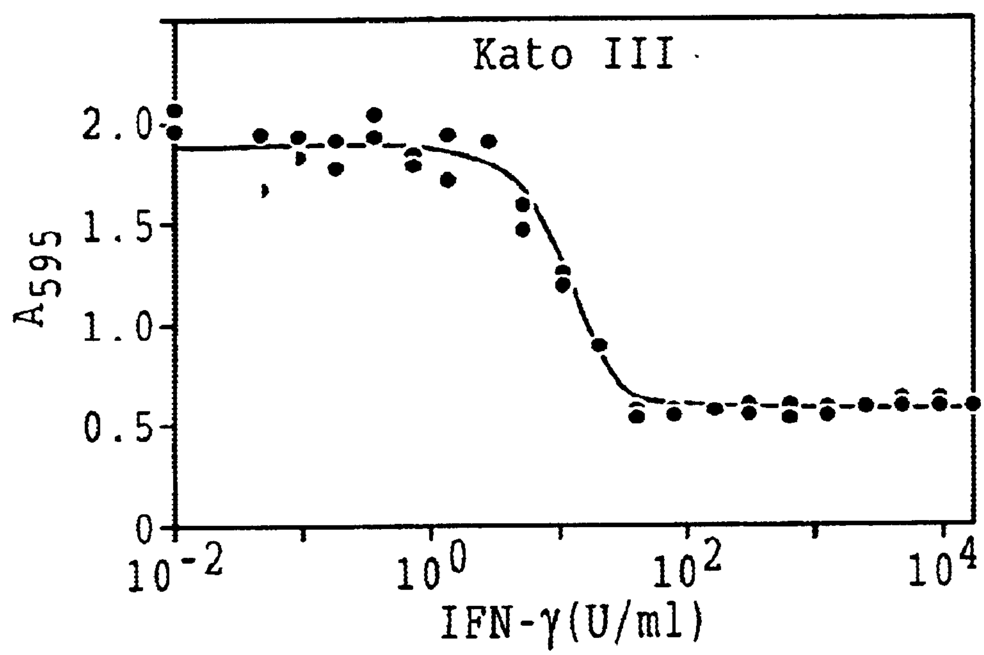
FIGS. 7A and 7B show the antiproliferative effect of IFN-γ on KATO III and AGS cells, respectively. Cells were seeded in duplicate in 96-well plates at a density of 5000 cells/well in the presence or absence of the indicated concentrations of IFN-γ. After 48 hours, the viable cells were determined using the CellTiter 96 Proliferation Assay™ (Promega) and measuring the absorbance at 595 nm.
Figure 7B:
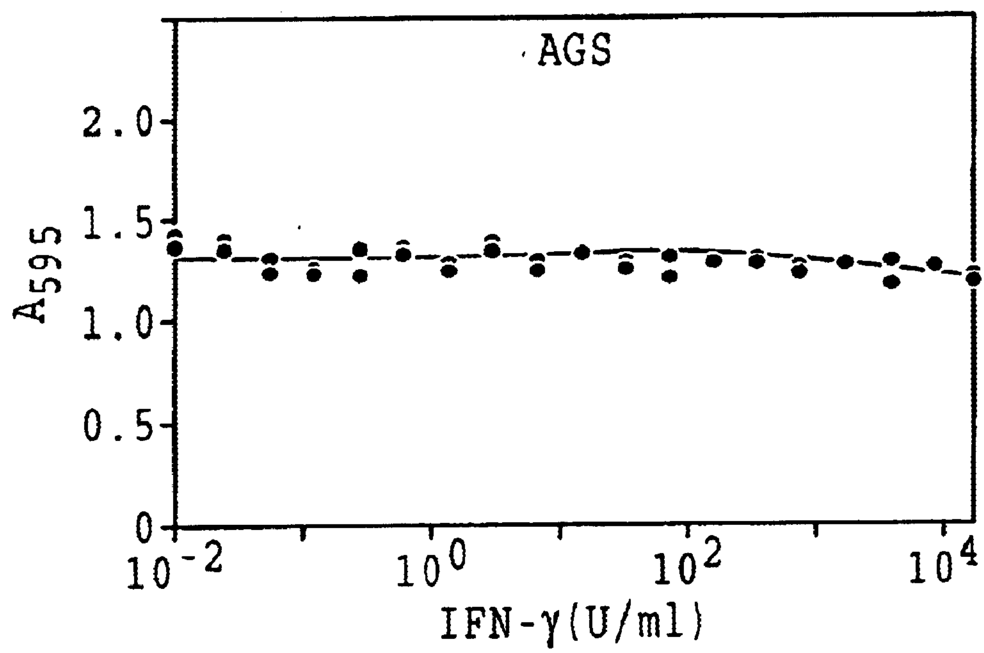

To determine if there were any functional differences between the gastric cell lines that expressed GBP-4 and the KATO III cells that did not express GBP-4, the ability of varying doses of IFN-γ to induce an antiproliferative response was analyzed. Cells were plated and treated with varying doses of IFN-γ for 24 to 96 hours. KATO III cells showed an inhibition of growth when exposed to as little as 10 units per ml of IFN-γ for 48 hours (FIG. 7A). The antiproliferative effect of IFN-γ was first seen at 24 hours and was more prominent by 72 to 96 hours. In contrast, the AGS cell line was resistant to the growth-inhibitory effects of IFN-γ (FIG. 7B) and showed no decrease in growth after as long as 96 hours of treatment. The other cell lines which expressed GBP-4—Hs746T, RF-1, and RF-48—were also resistant to IFN-γ-induced growth inhibition. These results demonstrate an interesting association between GBP-4 induction by IFN-γ treatment and resistance to the growth-inhibitory effects of IFN-γ.

In Situ Hybridization Demonstrates that GBP-4 is Expressed in Tumor Cells

All solid tumors are composed of a mixture of neoplastic and non-neoplastic cells. The latter consists predominantly of fibrovascular and inflammatory elements, which can constitute 10 to 90 percent of the total number of cells in a tumor. Vogelstein, *N Engl J Med*, 3: 525–532 (1988). Normal human gastric mucosa is virtually devoid of lymphoid tissue. The gastric adenocarcinoma sample used herein was characterized histologically as containing sheets of poorly differentiated malignant cells without a prominent lymphocytic infiltrate. This study was done to determine whether the malignant gastric cells in the original tumor were the source of the GBP-4 or infiltrating lymphocytes were the site of expression. To answer this question, in situ hybridization was performed on tissue from the original gastric carcinoma and adjacent uninvolved gastric mucosa. A strong GBP-4 hybridization signal was seen with the antisense probe over the infiltrating, poorly differentiated gastric carcinoma. No signal was observed with the sense control probe, or in the normal stomach. The only other adult tissue that showed positivity was the presence of a focal signal over malignant cells in the infiltrating squamous carcinoma of the lung. Fetal stomach, adrenal, liver, spleen, lungs, heart, skeletal muscle, ribs, and spinal cord were all negative. These results demonstrate that the malignant gastric cells and not infiltrating leukocytes are the site of GBP-4 expression.

3. Discussion

A new member of the human interferon-induced GBP family of proteins has been isolated and characterized. GBP-4 shares 60% overall sequence homology with two other members of the family, GBP-1 and GBP-2. The gene for GBP-4 has been localized to chromosome 1 at 1p31-1p32, in close physical linkage to GBP-1 and GBP-2. Translocations and deletions of this chromosomal region have been reported in human malignancies. Nagai et al., *Cancer Res*, 55: 1752–1757 (1995); Iolascon et al., *Leukemia*, 11: 359–63 (1997). The linkage between the GBP genes suggested that they are derived from duplication of a common ancestral gene and that their expression may be under the control of the same regulatory elements. Briken et al., *Mol Cell Biol*, 15: 975–982 (1995); Nicolet and Paulnock, *J Immunol*, 152: 153–162 (1994).

The amino acid sequence of GBP-4 predicts a protein of 67 kDa which contains the consensus tripartite GTP-binding motifs, GXXXXGK(S/T) (SEQ ID NOS: 7 and 8, respectively), DXXG (SEQ ID NO:9), and (N/T)KXD (SEQ ID NOS: 10 and 11, respectively) in the amino terminal region of the protein. If present in a protein sequence in an ordered fashion and with a consensus spacing requirement of 40–80 amino acids between the first and second, and between the second and third sequence elements, these motifs are associated with guanine nucleotide-binding activity. Dever et al., *Proc Natl Acad Sci USA* 84: 1814–1818 (1987).

Unlike the mammalian and chicken interferon-induced GBPs, which lack an (N/T)KXD consensus sequence (SEQ ID NOS: 10 and 11, respectively), human GBP-4 is unique in that it contains two (N/T)KXD sequences (SEQ ID NOS: 10 and 11, respectively): one at amino acid positions 109–112, and one at positions 132–135. The NKXD sequence (SEQ ID NO:10) in GBP-4 at positions 132–135, with a spacing of 31 amino acids from the second element, DXXG (SEQ ID NO:9), is closer to the usual distance observed than the NKXD sequence (SEQ ID NO:10) in GBP-4 at positions 109–112, which is only eight amino acids from the DXXG sequence (SEQ ID NO:9). This suggests that the NKXD sequence (SEQ ID NO:10) at positions 132–135 may be a site for guanine nucleotide binding.

GTP binding proteins that contain the (N/T)KXD motif (SEQ ID NOS: 10 and 11, respectively) can be divided into two groups, those which have threonine as the first residue, like the Mx proteins, and those which have an asparagine, like H-Ras. In the Ras oncoprotein, the first two consensus motifs constitute the phosphoryl-binding sequences, whereas the third element represents the guanine-specificity region. Dever et al., *Proc Natl Acad Sci USA*, 84: 1814–1818 (1987);Dever and Merrick, The GTP-binding domain revisited, In L. Bosch, B. Kraal, and A. Parmegianni (ed.), The guanine-nucleotide binding proteins: common structural and functional properties (Plenum Press: New York, 1995), p. 35–48; Jurnak, *Science*, 230: 32–36 (1985). Both (N/T)KXD sequences (SEQ ID NOS:10 and 11, respectively) of GBP-4 are like Ras and contain asparagine as the first residue. The presence of the third motif in determining guanine specificity is not absolute; however, GBP-1 does not possess a (N/T)KXD motif (SEQ ID NOS:10 and 11, respectively, yet only binds GTP, GDP, and GMP (Cheng et al.,(1991), supra), while GBP-4 contains two motifs and binds ADP, CDP, and CMP in addition to GDP, GTP, and GMP. Guanine nucleotide binding is necessary for activation of the GTPase activity of GBPs to hydrolyze GTP to GDP. GBP-1 can degrade a significant fraction of GTP to GMP (Cheng et al., (1991), supra), while GBP-2 hydrolyzes GTP mainly to GDP. Neun et al., *FEBS Lett* 390: 69–72 (1996).

The carboxyl-terminal region of many GTP binding proteins contains a CXXX (SEQ ID NO:12) isoprenylation signal which is a cysteine residue followed by two aliphatic amino acids and another amino acid. An isoprenoid addition of either a farnesyl or geranylgeranyl moiety to the cysteine residue occurs after synthesis and remains linked for the life span of the protein. Zhang and Casey, *Annu Rev Biochem*, 65: 241–269 (1996). These isoprenoid modifications affect protein function as has been reported for the oncoprotein Ras, which is farnesylated at its CXXX (SEQ ID NO:12) box. Hancock et al., *Cell*, 63: 133–139 (1990). This modification is required for oncogenic forms of Ras to transform cells. Farnesyl transferase inhibitors have been recently developed to block this reaction and thus render Ras and similar proteins inactive. Gibbs et al., *Cell*, 77: 175–178 (1994). Studies with Ras have shown that the serine residue in the last position of the CXXX (SEQ ID NO:12) box is a signal for farnesyl transferase. GBP-1 has a serine containing CXXX (SEQ ID NO:12) box and undergoes farnesylation. Nantais et al., *J Leukoc Biol*, 60: 423–31 (1996). It is unknown how this modification affects the function of GBP-1. Within the carboxyl-terminal region of GBP-4, a CXXG-box (SEQ ID-NO:12) sequence is found at positions 554–557. It remains to be determined whether GBP-4 undergoes any lipid post-translational modifications at this site which may affect its activation state or alter its cellular localization.

GBP-4 appears to be associated with intracellular endosomal membranes. Endosomes carry out several processes associated with endocytosis, including sorting and transport of internalized molecules and receptors to specific intracellular destinations. Gruenberg and Maxfield, *Curr Opin Cell Biol*, 7: 552–563 (1995). Upon arrival at the trans-Golgi network from the endoplasmic reticulum, endosomal membrane proteins are either directly transported to the endosomes or are first transported to the cell membrane from which they are rapidly internalized into the endocytotic pathway for delivery to the endosomes. The sorting to the endosomes via the plasma membrane has been shown to be specified by tyrosine- and leucine-based sorting motifs in the cytoplasmic tails of proteins. Marks et al., *J Cell Biol*, 135: 341–354 (1996). As the plasma membrane does not appear to be immunolabeled for GBP-4, without being limited to any one theory, it is believed that the protein is sorted out from the trans-Golgi network and directly routed to the endosomal pathway. GBP-4 does contain seven di-leucine motifs and five LX motifs (where X is one of the hydrophobic amino acids A, C or I) that could act as potential trans-Golgi network sorting signals. Marks et al., supra.

Northern blot analysis showed that GBP-4 was expressed in the freshly isolated gastric tumor but was not present in normal stomach tissue. In situ hybridization confirmed that GBP-4 expression was associated with the malignant epithelial cells of the gastric adenocarcinoma. No signal was observed in the epithelium of the adjacent normal stomach. The only other tissue with positive signal was a squamous carcinoma of the lung; here the signal was focal and appeared related to keratinization of the tumor cells. No signal was observed in any of the normal adult or any of the fetal tissues examined. The expression of GBP-4 in the gastric carcinoma cells, but not in the dividing cells in gastric crypts or in infiltrating lymphocytes, suggests that GBP-4 is not related to normal cell proliferation but may be associated with malignant transformation. Alternatively, GBP-4 expression may be a result of IFN-γ produced by tumor-associated cells.

Synthesis of the large (>65 kDa) GBPs has been shown to be tightly regulated by interferons. Human and mouse Gbp genes are induced by IFN-α but are more strongly induced by IFN-γ. Briken et al., supra. IFN-γ is produced by activated T cells and NK cells. GBP-4 expression is high in tissues with high lymphocyte content such as the spleen, lymph nodes, peripheral blood leukocytes, and the small intestine. These are sites where IFN-γ production by activated lymphocytes might be expected to induce GBP-4 expression. In HeLa and A431 cells, it was shown that GBP-4 expression is induced after 18 hours of IFN-γ treatment but not induced by IFN-α. No endogenous GBP-4 expression was observed in five gastric cell lines, but four of the five lines expressed GBP-4 in response to IFN-γ induction. The lack of endogenous GBP-4 expression may be a consequence of the establishment of the cell lines in long-term culture.

IFN-γ has potent immunomodulatory and anti-proliferative actions. The one cell line, KATO III, that did not show GBP-4 expression after exposure to IFN-γ, was also the only cell line that retained responsiveness to the anti-proliferative effects of IFN-γ. Cell lines which expressed GBP-4 after IFN-γ induction were resistant to the growth-inhibiting effects of IFN-γ. This suggests an interesting association between GBP-4 expression after IFN-γ treatment and resistance to the growth-inhibitory effects of IFN-γ. It has been shown that IFN-γ is an inducer of GBP-4 in cell lines, but it is unknown if IFN-γ is the responsible inducer of GBP-4 in tumor tissue. Without being limited to any one theory, it is possible that GBP-4 expression is a result of an IFN-γ-mediated immune response to the tumor. Alternatively, other cytokines or mediators within the tumor may be responsible for GBP-4 expression. TNF-α and vascular endothelial growth factor in human endothelial cells, thromboprotein in CMK cells, and IL-4 in 9D cells are unable to induce GBP-4 expression.

This example has also demonstrated that gastric cell lines derived from tumors express IFN-γ receptors, but respond differently to IFN-γ induction, as shown by the different patterns of GBP expression. This may be a result of different regulatory pathways for GBP induction by IFN-γ. IFN-γ binds with high affinity to cell-surface receptors which activate the receptor-associated protein tyrosine kinases, JAK1 and JAK2. These kinases phosphorylate the latent cytoplasmic transcription factor Stat1 which translocates to the nucleus, where it binds to GAS elements of IFN-γ-responsive promoters. Darnell et al., *Science*, 264: 1415–1421 (1994); Shuai, *Curr Opin Cell Biol*, 6: 253–259 (1994). GBP genes are immediate early genes induced by IFN-γ whose promoters were first shown to contain GAS elements. Decker et al., *EMBO J*, 8: 2009–2014 (1989). The induction of the human GBP-1 gene by IFN-γ in fibroblasts has been shown to be mediated by Stat1. Lew et al., *Mol Cell Biol*, 11: 182–191 (1991). The mouse GBP-1 (mGBP-1) gene, in contrast, responds poorly to IFN-γ, and mGBP-1 induction by IFN-γ has been shown to be dependent on IRF-1. Briken et al., supra. mGBP-1 genes can be activated by the expression of cDNA's for IRF-1 independently of IFN-γ and in IRF-1 −/− embryonic fibroblasts; no GBP gene expression is seen after IFN-γ treatment. IRF-1 is an IFN-γ regulated tumor suppressor gene whose gene product acts like p53 in mediating radiation-induced cellular growth arrest via p21 transcriptional activation. Tanaka et al., *Nature*, 382: 816–818 (1996). IRF-1 may be a factor involved in cancer tumorigenesis (Tamura et al., *Cancer Res*, 56: 612–615 (1996)) and human haematopoietic neoplasms (Willman et al., *Science*, 259: 968–971 (1993)) and may be involved in the regulation of GBP-4 expression in gastric cancer.

Example II

*E. coli* Expression of cDNA Encoding Human GBP-4

Figure 8:
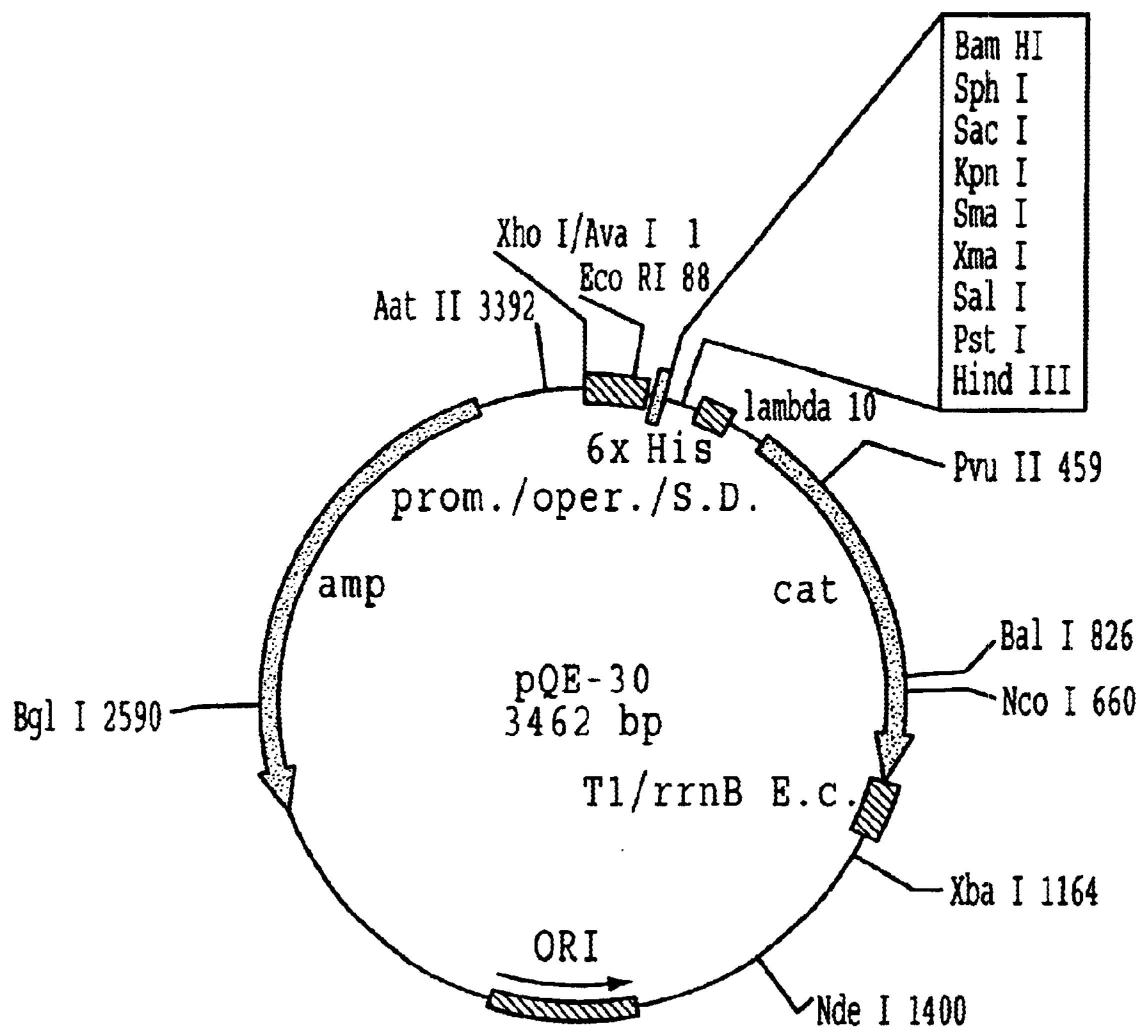
FIG. 8 depicts a restriction map of pQE-30, an expression vector used for expressing GBP-4 DNA in *E. coli* cells.

An expression vector from Qiagen Inc. called pQE-30 was used for this example. A restriction map of pQE-30 is shown in FIG. 8. The plasmid for GBP-4 of Example I was digested with BamHI and SalI. The resulting DNA fragment was ligated into pQE-30 previously cut with BamHI and SalI to accommodate the DNA fragment using standard ligation methodology as described in Sections 5.10 to 5.11 of Sambrook et al., supra. The resulting vector is called pQE30.hu.GBP4.

Competent *E. coli* 27C7 cells were transformed with pQE30.hu.GBP4 by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

One transformed colony was used to inoculate sterile LB broth containing 20 mg/L tetracycline. The flask culture was incubated at 35–39° C. until the optical density at 550 nm reached approximately 1.0. Sterile glycerol was added to the culture to give a final concentration of glycerol of 10% (v/v).

Example III

Mammalian Expression of cDNA Encoding Human GBP-4

Transient transfection of 293 cells with the expression plasmid for GBP-4 is described in Example I.

Large-scale expression of GBP-4 could be performed by transiently introducing by the dextran sulfate method (Sompayrac and Danna, *Proc. Natl. Acad. Sci. USA*, 12: 7575 (1981)) 700 μg of pRK-5.his.GBP-4 into the human embryonal kidney 293 cell line grown to maximal density (1.5 liters) in a 3-liter Belco microcarrier spinner flask. The cells are first concentrated from the spinner flask by centrifugation, and washed with PBS, and the DNA-dextran precipitate is incubated on the cell pellet for four hours. The cells are treated with 20% glycerol for 90 seconds, washed with a medium such as 50:50 DMEM:F-12 medium, and re-introduced into a 3-liter spinner flask containing 1.5 liter of the above medium plus 5 μg/ml bovine insulin and 0.1 μg/ml bovine transferrin.

In a different expression protocol, pRK-5.his.GBP4 can be transfected into COS cells using the same conditions as for the 293 cells described above.

While the above examples illustrate human GBP-4, the specification and claims are not limited thereto, and other GBP-4s can be isolated and their DNA cloned and expressed using the procedure detailed herein.

Example IV

Preparation of Antibodies that Bind GBP-4

1. Polyclonal Antibodies

Polyclonal antisera are generated in female New Zealand White rabbits against human GBP-4. The antigens used can be proteins fused with histidine and proteins fused with the Fc portion of IgG. The protein is homogenized with Freund's complete adjuvant for the primary injection and with Freund's incomplete adjuvant for all subsequent boosts. For the primary immunization and the first boost, 3.3 μg per kg body weight is injected directly into the popliteal lymph nodes as described in Bennett et al., *J. Biol. Chem.*, 266: 23060–23067 (1991) and "Production of Antibodies by Inoculation into Lymph Nodes" by Morton Sigel et al. in *Methods in Enzymology*, Vol. 93 (New York: Academic Press, 1983). For all subsequent boosts, 3.3 μg per kg body weight is injected into subcutaneous and intramuscular sites. Injections are done every 3 weeks with bleeds taken on the following two weeks.

2. Monoclonal Antibodies

Techniques for producing monoclonal antibodies that can specifically bind a GBP-4 polypeptide are known in the art and are described, for instance, in Goding, supra. Immunogens that may be employed include purified GBP-4, fusion proteins containing GBP-4, and cells expressing recombinant GBP-4 on the cell surface. Selection of the immunogen can be made by the skilled artisan without undue experimentation.

Mice, such as Balb/c, are immunized with the GBP-4 immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect GBP-4 antibodies. After a suitable antibody titer has been detected, the animals "positive" for antibodies can be injected with a final intravenous injection of a GBP-4 polypeptide. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96-well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against a GBP-4 polypeptide. Determination of "positive" hybridoma cells secreting the desired monoclonal antibodies against a GBP-4 polypeptide is within the skill in the art.

The positive hybridoma cells can be injected intraperitoneally into syngeneic Balb/c mice to produce ascites containing the anti-GBP-4 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example V

Use of Antibodies that Bind GBP-4

1. Cell Lines

The established human breast tumor cells BT474 and MDA-MB-231 (which are available from ATCC) are grown in minimum essential medium (Gibco, Grand Island, N.Y.) supplemented with 10% heat-inactivated fetal bovine serum (FBS) (HyClone, Logan, Utah), sodium pyruvate, L-glutamine (2 mM), non-essential amino acids and 2×vitamin solution and maintained at 37° C. in 5% $CO_2$. Zhang et al., *Invas. & Metas.*, 11:204–215 (1991); Price et al., *Cancer Res.*, 50:717–721 (1990).

2. Antibodies

Anti-GBP-4 monoclonal antibodies that may be prepared as described above are harvested with phosphate-buffered saline (PBS) containing 25 mM EDTA and used to immunize BALB/c mice. The mice are given injections i.p. of $10^7$ cells in 0.5 ml PBS on weeks 0, 2, 5 and 7. The mice with antisera that immunoprecipitate $^{32}$P-labeled GBP-4 are given i.p. injections of a wheat germ agglutinin-Sepharose (WGA) purified GBP-4 membrane extract on weeks 9 and 13. This is followed by an i.v. injection of 0.1 ml of the −1 preparation and the splenocytes are fused with mouse myeloma line X63-Ag8.653. Hybridoma supernatants are screened for GBP-4 binding by ELISA and radioimmunoprecipitation. MOPC-21 (IgG1), (Cappell, Durham, N.C.), is used as an isotype-matched control.

Additionally, the anti-ErbB2 $IgG_1K$ murine monoclonal antibodies 4D5 (ATCC CRL 10463 deposited May 24, 1990) and 7C2, specific for the extracellular domain of ErbB2, may be used with the above antibodies. They are produced as described in Fendly et al., *Cancer Research*, 50:1550–1558 (1990) and W089/06692.

3. Analysis of Cell Cycle Status and Viability

Cells are simultaneously examined for viability and cell cycle status by flow cytometry on a FACSTAR PLUS™ (Becton Dickinson Immunocytometry Systems USA, San Jose, Calif.). Tumor cells are harvested by washing the monolayer with PBS, incubating cells in 0.05% trypsin and 0.53 mM EDTA (Gibco), and resuspending them in culture medium. The cells are washed twice with PBS containing 1% FBS and the pellet is incubated for 30 minutes on ice with 50 μl of 400 μm 7-aminoactinomycin D (7AAD) (Molecular Probes, Eugene, Oreg.), a vital dye which stains all permeable cells. Cells are then fixed with 1.0 ml of 0.5% paraformaldehyde in PBS and simultaneously permeabilized and stained for 16 hours at 4° C. with 220 μl of 10 μg/ml HOECHST 33342™ dye (also a DNA binding dye) containing 5% TWEEN 20™.

The data from $1\times10_4$ cells are collected and stored using LYSYS II™ software and analyzed using PAINT-A-GATE™ software (Becton Dickinson). Darzynkiewica et al., *Cytometry*, 13:795–808 (1992) and Picker et al., *J. Immunol.*, 150:1105–1121 (1993). The viability and percentage of cells in each stage of the cell cycle are determined on gated single cells using 7AAD and Hoechst staining, respectively. (Cell doublets are excluded by pulse analysis of width vs. area of the Hoechst signal.) Cell numbers are determined using a hemocytometer.

4. DNA Synthesis

This thymidine proliferation assay takes place over four days. On the first day, the cells are trypsinized from a fresh non-confluent plate in regular medium late in the day. Then the cells are plated at the desired concentration, for example, 3T3 cells in 96-well, flat-bottom plates at 5000 cells/well, and 3T3 cells in 48-well plates at 100,000 cells/well. The plates are allowed to incubate at 37° C. overnight.

The next day 200 μl of 0.2% FBS medium is added, then aspirated, then another 200 μl is added and the plates are incubated overnight for 24 hours.

On the third day the 0.2% FBS medium is aspirated and replaced with at least 150 μl of 0.2% FBS medium containing anti-GBP-4 antibodies. For a positive control, 15 ng/ml of basic fibroblast growth factor (bFGF) or cells with original serum containing 10% fetal bovine serum (FBS) can be used, and for a negative control, 0.2% FBS medium can be used as the continuing medium. The resulting medium is incubated 18–20 hours at 37° C.

On the fourth day 5 μCi/ml of $^3$H-thymidine (Amersham, Arlington, Va.) is added to the cells. For 96-well plates 20 μl of a diluted thymidine 1:20 in starvation medium is added. Then the cells are incubated for four hours at 37° C. After incubation the cells are harvested and counted. For the 96-well automated format, the harvesting is done by aspirating the medium for appropriate disposal. For this purpose 100 μl 2×trypsin is added to each well. The cells are harvested onto GF/C filters using the Packard™ harvester. Then the cells are rinsed with ethanol and allowed to dry completely. After the cells are dried, 40 μl of Microscint-20™ counting fluid is added, and the cells are heat sealed and then counted. Those induced by the anti-GBP-4 antibodies are compared to those induced with the control.

5. Affinity of Binding to Putative Receptor

Radioiodinated anti-GBP-4 antibodies are prepared by the Iodogen™ method. Fracker et al., *Biochem. Biophys. Res. Comm.*, 80:849–857 (1978). Binding assays are performed using appropriate receptor-expressing cells cultured in 96-well tissue culture plates (Falcon, Becton Dickinson Labware, Lincoln Park, N.J.). The cells are trypsinized and seeded in wells of 96-well plates at a density of $10^4$ cells/well and allowed to adhere overnight. The monolayers are washed with cold culture medium supplemented with 0.1% sodium azide and then incubated in triplicate with 100 μl of serial dilutions of $^{125}$I-anti-GBP-4 antibodies in cold culture medium with 0.1% azide for 4 hours on ice. Non-specific binding is estimated by the preincubation of each sample with a 100-fold molar excess of nonradioactive antibodies in a total volume of 100 μl. Unbound radioactivity is removed by two washes with cold medium with 0.1% sodium azide. The cell-associated radioactivity is detected in a gamma counter after solubilization of the cells with 150 μl of 0.1 M NaOH/well. The GBP-4 binding constant ($K_d$) and anti-GBP-4 antibody binding affinity are determined by Scatchard analysis. It is expected that the antibodies against GBP-4 will affect the growth of these cells.

Deposit of Material

The following material has been deposited with the American Type Culture Collection, 10801 University Blvd., Manassas, Va., USA (ATCC):

| Material | ATCC Dep. No. | Deposit Date |
|---|---|---|
| pRK5-based plasmid pRK5.hu.GBP4-histag.71 | 209.456 | Nov. 12, 1997 |

This deposit was made under the provisions of the Budapest Treaty on the International Recognition of the Deposit of Microorganisms for the Purpose of Patent Procedure and the Regulations thereunder (Budapest Treaty). This assures maintenance of viable cultures of the deposits for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the material on deposit should die or be lost or destroyed when cultivated under suitable conditions, the material will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated nucleic acid comprising DNA encoding a guanylate binding protein-4 ("GBP-4") polypeptide comprising the sequence of amino acids 1 to 591 of FIG. 1 (SEQ ID NO:3).

2. The nucleic acid of claim 1 wherein said DNA encodes a GBP-4 polypeptide consisting of amino acids 1 to 591 of FIG. 1 (SEQ ID NO:3).

3. A vector comprising the nucleic acid of claim 1.

4. A host cell comprising the vector of claim 3.

5. The host cell of claim 4 which is selected from the group consisting of a human cell, yeast cell, CHO cell, and *E. coli*.

6. A process for producing a GBP-4 polypeptide comprising culturing the host cell of claim 4 under conditions suitable for expression of the GBP-4 polypeptide and recovering the GBP-4 polypeptide from the cell culture.

7. An isolated nucleic acid comprising DNA encoding the same polypeptide encoded by the GBP-4 polypeptide cDNA in ATCC deposit no. 209,456.

8. A vector comprising the nucleic acid of claim 7.

9. A host cell comprising the vector of claim 8.

10. The host cell of claim 9 which is selected from the group consisting of a human cell, yeast cell, CHO cell, and *E. coli*.

11. A process for producing a GBP-4 polypeptide comprising culturing the host cell of claim 9 under conditions suitable for expression of the GBP-4 polypeptide and recovering the GBP-4 polypeptide from the cell culture.

12. An isolated nucleic acid comprising DNA which (a) hybridizes under stringent conditions with DNA encoding GBP-4 polypeptide comprising amino acids 1 to 591 of FIG. 1 (SEQ ID NO: 3), (b) encodes a GBP-4 polypeptide that binds to at least one guanine nucleotide, and (c) encodes a GBP-4 polypeptide comprising a Asp-Thr-Glu-Gly (amino acid residues 97–100 of SEQ ID NO: 3) GTP-binding consensus motif, wherein the stringent conditions are 0.015 M sodium chloride/0.0015 M sodium citrate/0.1% sodium dodecyl sulfate at 50° C.

13. The nucleic acid of claim 12 wherein the encoded GBP-4 polypeptide of (b) binds to GTP or GMP.

14. A vector comprising the nucleic acid of claim 12.

15. A host cell comprising the vector of claim 14.

16. The host cell of claim 15 which is selected from the group consisting of a human cell, yeast cell, CHO cell, and *E. coli*.

17. A process for producing a GBP-4 polypeptide comprising culturing the host cell of claim 15 under conditions suitable for expression of the GBP-4 polypeptide and recovering the GBP-4 polypeptide from the cell culture.

18. An isolated nucleic acid comprising DNA (a) having at least 95% sequence identity to a DNA encoding a guanylate binding protein-4 ("GBP-4") polypeptide comprising the sequence of amino acids 1 to 591 of FIG. 1 (SEQ ID NO:3) and (b) encoding a GBP-4 polypeptide that binds to at least one guanine nucleotide.

19. The nucleic acid of claim 18 wherein the encoded GBP-4 polypeptide of (b) binds to GTP or GMP.

20. The nucleic acid of claim 18 wherein the DNA has at least 99% sequence identity to a DNA encoding a GBP-4 polypeptide comprising the sequence of amino acids 1 to 591 of FIG. 1 (SEQ ID NO:3).

21. The nucleic acid of claim 18 wherein the GBP-4 is expressed in stomach cancer cells or tissue but not in normal, non-cancerous stomach cells or tissue.

22. A vector comprising the nucleic acid of claim 18.

23. A host cell comprising the vector of claim 22.

24. The host cell of claim 23 which is selected from the group consisting of a human cell, yeast cell, CHO cell, and *E. coli*.

25. A process for producing a GBP-4 polypeptide comprising culturing the host cell of claim 23 under conditions suitable for expression of the GBP-4 polypeptide and recovering the GBP-4 polypeptide from the cell culture.

26. An isolated nucleic acid comprising DNA which (a) hybridizes under stringent conditions with DNA encoding GBP-4 polypeptide comprising amino acids 1 to 591 of FIG. 1 (SEQ ID NO: 3), (b) encodes a GBP-4 polypeptide that binds to at least one guanine nucleotide; and (c) encodes a GBP-4 polypeptide comprising:

(i) a Asp-Thr-Glu-Gly (amino acid residues 97–100 of SEQ ID NO: 3) GTP-binding consensus motif;

(ii) a Thr-Leu-Arg-Asp (amino acid residues 179–182 of SEQ ID NO: 3) potential casein kinase II phosphorylation site;

(iii) a Ser-Gly-Lys-Glu (amio acid residues 568–571 of SEQ ID NO: 3) potential casein kinase II phosphorylation site;

(iv) a Thr-Leu-Arg (amino acid residues 179–181 of SEQ ID NO: 3) potential protein kinase C phosphorylation site;

(v) a Thr-Met-Arg (amino acid residues 562–564 of SEQ ID NO: 3) potential protein kinase C phosphorylation site;

(vi) a Ser-Gly-Lys (amino acid residues 568–570 of SEQ ID NO: 3) potential protein kinase C phosphorylaton site;

(vii) a Ser-Gln-Lys (amino acid residues 586–588 of SEQ ID NO: 3) potential protein kinase C phosphorylaton site;

(viii) a Gly-Ile-Met-Val-Asn-Gly (amino acid residues 283–288 of SEQ ID NO: 3) potential N-myristoylation site;

(ix) a Gly-Ser-Gln-Gln-Gly-Val (amino acid residues 579–584 of SEQ ID NO: 3) potential N-myristoylation site; or (x) a Cys-Phe-Ile-Ser (amino acid residues 554–557 of SEQ ID NO: 3) potential prenylation site, wherein the stringent conditions are 0.015 M sodium chloride/0.0015 M sodium citrate/0.1% sodium dodecyl sulfate at 50° C.

27. The nucleic acid of claim 26, wherein the DNA encodes a GBP-4 polypeptide comprising a Cys-Phe-Ile-Ser (amino acid redidues 554–557 of SEQ ID NO: 3) potential prenylation site.

28. The nucleic acid of claim 26, wherein the DNA encodes a GBP-4 polypeptide comprising a Thr-Leu-Arg- Asp (amino acid redidues 179–182 of SEQ ID NO: 3) potential casein kinase II phosporylation site.

29. The nucleic acid of claim 26, wherein the DNA encodes a GBP-4 polypeptide comprising a Ser-Gly-Lys-Glu (amino acid redidues 568–571 of SEQ ID NO: 3) potential casein kinase II phosporylation site.

30. The nucleic acid of claim 26, wherein the DNA encodes a GBP-4 polypeptide comprising a Thr-Leu-Arg (amino acid redidues 179–181 of SEQ ID NO: 3) potential protein kinase C phosphorylation site.

31. The nucleic acid of claim 26, wherein the DNA encodes a GBP-4 polypeptide comprising a Thr-Met-Arg (amino acid redidues 562–564 of SEQ ID NO: 3) potential protein kinase C phosphorylation site.

32. The nucleic acid of claim 26, wherein the DNA encodes a GBP-4 polypeptide comprising a Ser-Gly-Lys (amino acid redidues 568–570 of SEQ ID NO: 3) potential protein kinase C phosphorylation site.

33. The nucleic acid of claim 26, wherein the DNA encodes a GBP-4 polypeptide comprising a Ser-Gln-Lys (amino acid redidues 586–588 of SEQ ID NO: 3) potential protein kinase C phosphorylation site.

34. The nucleic acid of claim 26, wherein the DNA encodes a GBP-4 polypeptide comprising a Gly-Ile-Met-Val-Asn-Gly (amino acid redidues 283–288 of SEQ ID NO: 3) potential N-myristoylation site.

35. The nucleic acid of claim 26, wherein the DNA encodes a GBP-4 polypeptide comprising a Gly-Ser-Gln-Gln-Gly-Val (amino acid redidues 579–584 of SEQ ID NO: 3) potential N-myristoylation site.

* * * * *